US008642051B2

(12) United States Patent
Stillman

(10) Patent No.: US 8,642,051 B2
(45) Date of Patent: Feb. 4, 2014

(54) METHOD OF HYDRATION; INFUSION PACKET SYSTEM(S), SUPPORT MEMBER(S), DELIVERY SYSTEM(S), AND METHOD(S); WITH BUSINESS MODEL(S) AND METHOD(S)

(76) Inventor: Suzanne Jaffe Stillman, Los Angeles, CA (US)

( * ) Notice: Subject to any disclaimer, the term of this patent is extended or adjusted under 35 U.S.C. 154(b) by 0 days.

(21) Appl. No.: 09/963,209

(22) Filed: Sep. 26, 2001

(65) Prior Publication Data
US 2002/0012689 A1    Jan. 31, 2002

Related U.S. Application Data

(63) Continuation-in-part of application No. PCT/US01/09171, filed on Mar. 21, 2001.

(60) Provisional application No. 60/192,243, filed on Mar. 21, 2000.

(51) Int. Cl.
*A61K 9/00* (2006.01)
*A61K 47/00* (2006.01)
*A23L 2/00* (2006.01)
*A23L 2/38* (2006.01)

(52) U.S. Cl.
USPC .......................... 424/400; 424/439; 426/590

(58) Field of Classification Search
USPC .................. 424/439, 484, 489, 725; 435/174
See application file for complete search history.

(56) References Cited

U.S. PATENT DOCUMENTS

| | | | |
|---|---|---|---|
| 2,199,406 A | 5/1940 | Jablon | |
| 2,311,923 A * | 2/1943 | Lautmann | 424/440 |
| 2,370,931 A | 3/1945 | Bogin | |
| 2,819,167 A * | 1/1958 | Irmscher | 426/83 |
| 3,607,299 A | 9/1971 | Bolt | |
| 3,796,813 A * | 3/1974 | Kurland | 426/86 |
| 4,076,846 A * | 2/1978 | Nakatsuka et al. | 426/62 |
| 4,271,142 A * | 6/1981 | Puglia et al. | 424/440 |
| 4,315,513 A | 2/1982 | Nawash et al. | 128/348 |
| 4,393,873 A | 7/1983 | Nawash et al. | 604/151 |
| 4,529,569 A * | 7/1985 | Palau | 264/321 |
| 4,551,329 A * | 11/1985 | Harris et al. | 424/440 |
| 4,563,161 A * | 1/1986 | Zimmerman | 446/156 |
| 4,605,123 A * | 8/1986 | Goodrum et al. | 206/0.5 |
| 4,609,556 A | 9/1986 | Goedert | 426/394 |
| 4,671,953 A * | 6/1987 | Stanley et al. | 424/440 |
| 4,711,784 A | 12/1987 | Yang | 426/5 |
| 4,749,575 A | 6/1988 | Rotman | 424/441 |
| 4,804,542 A | 2/1989 | Fischer et al. | 424/456 |
| 4,841,712 A | 6/1989 | Roou | 53/412 |
| 4,842,157 A * | 6/1989 | Stone-Parker et al. | 220/719 |
| 4,851,252 A | 7/1989 | Greither et al. | 426/599 |
| 4,851,339 A | 7/1989 | Hills | 435/67 |
| 4,853,235 A | 8/1989 | Tomomatsu | 426/93 |
| 4,863,737 A * | 9/1989 | Stanley et al. | 424/440 |
| 4,881,915 A * | 11/1989 | Liaw | 446/153 |
| 4,959,947 A | 10/1990 | Reif | 53/502 |
| 4,988,019 A * | 1/1991 | Dawes | 99/287 |
| 5,009,518 A | 4/1991 | Faltynek | 383/106 |
| 5,009,819 A | 4/1991 | Popescu et al. | 263/4.1 |
| 5,019,405 A | 5/1991 | Sapers | 426/250 |
| 5,024,824 A | 6/1991 | Henk | 423/213.5 |
| 5,024,842 A | 6/1991 | Edgren et al. | 424/473 |
| 5,035,515 A | 7/1991 | Crossman et al. | 383/38 |
| 5,051,261 A | 9/1991 | McGinity et al. | 424/464 |
| 5,051,269 A | 9/1991 | Noreille et al. | 426/453 |
| 5,085,634 A * | 2/1992 | Lackney | 604/77 |
| 5,089,307 A | 2/1992 | Ninomiya et al. | |
| 5,119,940 A | 6/1992 | Grindrod | 206/45.31 |
| 5,127,743 A | 7/1992 | Miller et al. | 383/109 |
| 5,284,667 A | 2/1994 | Zimmermann et al. | 426/420 |
| 5,294,458 A | 3/1994 | Fujimori | 426/635 |
| 5,366,741 A | 11/1994 | Van Der Zon | 426/79 |
| 5,447,730 A | 9/1995 | Greenleaf | 424/680 |
| 5,542,570 A | 8/1996 | Nottingham et al. | 221/192 |
| 5,543,164 A | 8/1996 | Krochta et al. | 426/302 |
| 5,549,757 A | 8/1996 | Morano | 127/42 |

(Continued)

FOREIGN PATENT DOCUMENTS

| | | |
|---|---|---|
| CA | 2182907 A | 2/1998 |
| CH | 272 538 A | 3/1951 |

(Continued)

OTHER PUBLICATIONS

"Problem: thirst, drinking, behavior, and involuntary dehydration," John E. Greenleaf (Medicine and Science in Sports and Exercise, 24:645-656 (1992).

(Continued)

*Primary Examiner* — Debbie K Ware
(74) *Attorney, Agent, or Firm* — Woodcock Washburn LLP

(57) ABSTRACT

Liquid activated infusion packet(s)/system, promoting hydration, containing active and/or inactive ingredients and/or a support member(s). Infusion Packet(s)/System is one or more individual compartments, and/or group(s), whereby the enveloping material(s) may be totally or partially dissolvable, edible, transparent, opaque, decorated, etc. Further, including of one or more: color(s), flavor(s), aroma(s), pharmaceutical(s), nutraceutical(s), dietary supplement(s), enzyme(s), pre/pro-biotic(s), amino-acid(s), soluble-fiber(s), diagnostic agent(s) etc. regardless of form, +/−effervescence, +/−uniform/controlled-release encapsulations into liquid for humans and/or animals. Enveloping material may be in whole and/or in combination; non-synthetic/porous, and/or synthetic porous/non-porous with deliberate perforations. Infusion Packet(s)/System+/−tag, support member for assistance, consumer compliance: promotion, advertising: education, entertainment, (toy/game), etc. Manual and/or power operated parts, lights, noise, etc. Additionally incorporated; unique business modalities with test market opportunities and/or the ability to provide income and/or esteem for the health challenged.

22 Claims, 13 Drawing Sheets

(56) References Cited

U.S. PATENT DOCUMENTS

| | | | | |
|---|---|---|---|---|
| 5,550,113 | A | 8/1996 | Mann | 514/54 |
| 5,554,400 | A * | 9/1996 | Stipp | 426/78 |
| 5,567,424 | A * | 10/1996 | Hastings | 424/195.17 |
| 5,578,304 | A | 11/1996 | Sipos | 424/94.1 |
| 5,578,336 | A | 11/1996 | Monte | 426/72 |
| 5,580,408 | A | 12/1996 | Vernon et al. | 156/176 |
| 5,601,716 | A | 2/1997 | Heinrich et al. | 210/490 |
| 5,613,601 | A * | 3/1997 | Boulanger et al. | 200/0.5 |
| 5,616,355 | A | 4/1997 | Haast et al. | 426/384 |
| 5,620,724 | A * | 4/1997 | Adler | 426/77 |
| 5,626,896 | A | 5/1997 | Moore et al. | 426/103 |
| 5,633,027 | A | 5/1997 | Cherukuri et al. | 426/96 |
| 5,653,996 | A | 8/1997 | Hsu | 424/450 |
| 5,657,712 | A * | 8/1997 | Romagnoli | 112/475.08 |
| 5,674,544 | A | 10/1997 | Shakspeare | 426/80 |
| 5,676,988 | A | 10/1997 | Coleman et al. | 426/134 |
| 5,683,997 | A | 11/1997 | Buhlmayer et al. | |
| 5,690,535 | A | 11/1997 | Coleman et al. | 446/236 |
| 5,716,688 | A * | 2/1998 | Burke et al. | 428/43 |
| 5,716,976 | A | 2/1998 | Bernstein | 514/386 |
| 5,721,345 | A | 2/1998 | Roberfroid | 536/4.1 |
| 5,728,681 | A * | 3/1998 | Kido et al. | 514/23 |
| 5,741,491 | A | 4/1998 | Jones | 424/195.1 |
| 5,768,142 | A | 6/1998 | Jacobs | |
| 5,772,017 | A | 6/1998 | Kang | 206/222 |
| 5,776,524 | A | 7/1998 | Reinhart | 426/2 |
| 5,792,754 | A | 8/1998 | Green | |
| 5,820,437 | A | 10/1998 | Coleman et al. | 446/196 |
| 5,820,867 | A | 10/1998 | Bewicke | 424/195.1 |
| 5,849,324 | A | 12/1998 | Dohnalek et al. | 424/440 |
| 5,851,578 | A * | 12/1998 | Gandhi | 426/590 |
| 5,852,917 | A | 12/1998 | Romagnoli | 53/479 |
| 5,862,997 | A | 1/1999 | Reinke | 239/728 |
| 5,866,188 | A | 2/1999 | Battist et al. | 426/549 |
| 5,869,059 | A | 2/1999 | Garza | |
| 5,885,640 | A | 3/1999 | Andersson | 426/316 |
| 5,888,514 | A | 3/1999 | Weisman | 424/195.1 |
| 5,891,465 | A | 4/1999 | Keller et al. | 424/450 |
| 5,897,022 | A | 4/1999 | Mann | 221/24 |
| 5,910,247 | A | 6/1999 | Outterside | 210/487 |
| 5,921,955 | A | 7/1999 | Mazer | |
| 5,922,350 | A | 7/1999 | Janoff et al. | 424/450 |
| 5,927,052 | A | 7/1999 | Nippes et al. | 54/445 |
| 5,928,664 | A | 7/1999 | Yang et al. | 424/440 |
| 5,951,452 | A | 9/1999 | Stevenson | 493/193 |
| 5,965,162 | A | 10/1999 | Fuisz et al. | 424/464 |
| 5,965,185 | A | 10/1999 | Bianco | |
| 5,968,569 | A | 10/1999 | Cavadini et al. | 426/61 |
| 5,972,415 | A * | 10/1999 | Brassart et al. | 426/634 |
| 5,981,498 | A | 11/1999 | Fukuda et al. | 514/25 |
| 5,989,602 | A | 11/1999 | Drury et al. | 426/79 |
| 5,993,880 | A | 11/1999 | Frost et al. | 426/540 |
| 6,007,838 | A | 12/1999 | Alving et al. | 424/450 |
| 6,008,252 | A | 12/1999 | Beale | 514/562 |
| 6,008,253 | A | 12/1999 | Meglasson | 514/565 |
| 6,022,576 | A | 2/2000 | Cirigliano et al. | 426/597 |
| 6,025,363 | A | 2/2000 | Giles, Jr. | 514/263 |
| 6,039,952 | A | 3/2000 | Sunvold et al. | 424/195.1 |
| 6,071,539 | A | 6/2000 | Robinson et al. | 424/466 |
| 6,083,582 | A * | 7/2000 | Chen et al. | 428/34.8 |
| 6,102,224 | A | 8/2000 | Sun et al. | 215/252 |
| 6,123,221 | A * | 9/2000 | Simpson | 221/33 |
| 6,129,265 | A * | 10/2000 | Perryman et al. | 229/103.1 |
| 6,133,323 | A | 10/2000 | Hayek | 514/725 |
| 6,165,495 | A * | 12/2000 | Blankenship | 424/440 |
| 6,168,795 | B1 | 1/2001 | Djang | 424/195.1 |
| 6,174,554 | B1 | 1/2001 | So | 426/98 |
| 6,180,099 | B1 | 1/2001 | Paul | 424/93.4 |
| 6,180,131 | B1 | 1/2001 | Sunvold et al. | 424/442 |
| 6,182,861 | B1 | 2/2001 | Kovens | |
| 6,190,591 | B1 | 2/2001 | van Lengerich | 264/141 |
| 6,191,161 | B1 | 2/2001 | Ka'nai et al. | |
| 6,204,291 | B1 | 3/2001 | Sunvold et al. | 514/556 |
| 6,207,638 | B1 | 3/2001 | Portman | 514/2 |
| 6,212,959 | B1 | 4/2001 | Perkins | 73/861.77 |
| 6,214,390 | B1 | 4/2001 | Weinstein et al. | 426/74 |
| 6,214,788 | B1 | 4/2001 | Velazco et al. | 512/19 |
| 6,217,931 | B1 | 4/2001 | Meister | 426/594 |
| 6,221,832 | B1 | 4/2001 | Casteel et al. | 516/446 |
| 6,224,873 | B1 | 5/2001 | Jones | 424/195.1 |
| 6,224,922 | B1 | 5/2001 | Fonte | 426/115 |
| 6,225,341 | B1 | 5/2001 | Bischofberger et al. | |
| 6,235,323 | B1 | 5/2001 | Carns et al. | 426/78 |
| 6,248,375 | B1 * | 6/2001 | Gilles et al. | 426/72 |
| 6,248,390 | B1 * | 6/2001 | Stillman | 426/590 |
| 6,251,450 | B1 | 6/2001 | Giacoman | 426/106 |
| 6,255,341 | B1 | 7/2001 | DeMichele et al. | 514/474 |
| 6,258,870 | B1 | 7/2001 | Hubbell et al. | 522/26 |
| 6,261,589 | B1 | 7/2001 | Pearson et al. | 424/439 |
| 6,261,610 | B1 | 7/2001 | Sher et al. | 426/74 |
| 6,263,923 | B1 | 7/2001 | Castillo | 141/100 |
| 6,264,997 | B1 | 7/2001 | Yamakoshi et al. | 424/766 |
| 6,265,450 | B1 | 7/2001 | Asami et al. | 514/691 |
| 6,268,011 | B1 | 7/2001 | Hoie | 426/634 |
| 6,279,505 | B1 | 8/2001 | Plester et al. | 118/723 |
| 6,280,075 | B1 | 8/2001 | Cadeo | 366/132 |
| 6,495,190 | B1 | 12/2002 | Yaginuma et al. | |
| 6,503,582 | B1 * | 1/2003 | Nardoza et al. | 428/15 |
| 6,733,804 | B1 | 5/2004 | Lohrey et al. | |
| 2001/0012525 | A1 * | 8/2001 | Mann | 424/727 |
| 2005/0095951 | A1 * | 5/2005 | Kempton | 446/327 |

FOREIGN PATENT DOCUMENTS

| CN | 2055129 U | | 3/1990 |
| DE | 10 45 314 B | | 11/1958 |
| DE | 40 01 500 A | | 7/1991 |
| DE | 296 16 646 U1 | | 1/1997 |
| DE | 198 42 526 A1 | | 3/2000 |
| EP | 0 448 325 A1 | | 9/1991 |
| FR | 2 671 332 A1 | | 7/1992 |
| FR | 2 786 303 A1 | | 5/2000 |
| JP | 58-130968 | | 8/1983 |
| JP | 06-075325 | | 3/1994 |
| JP | 7152952 A | | 6/1995 |
| JP | 10-314034 | | 12/1998 |
| WO | WO94/25011 | * | 11/1994 |
| WO | WO 99/35190 A1 | | 7/1999 |

OTHER PUBLICATIONS

Chandalia, M. et al., "Beneficial effects of high dietary fiber intake in patients with type 2 diabetes mellitus," The New England Journal of Medicine May 11, 2000, 342(19), 1392-1398.

Landin, K. et al., "Guar gum improves insulin sensitivity, blood lipids and blood pressure," American Journal of Clinical Nutrition, Dec. 1992, 56(6), 1061-1065.

Water: An Essential but overlooked nurient, Journal of American Dietetic Assoc (ADA): vol. 99, No. 2, Feb. 1999.

Reuters (London) Jun. 26, 2001 News Report: "High fiber diet can cut cancer risk of colorectal cancer by 40%" A Study.

"Liquid Candy How Soft Drinks are Harming American's Health," by Dr. Michael E. Jacobson of the Center for Science in the Public Interest (CSPI) Jun. 2005.

* cited by examiner

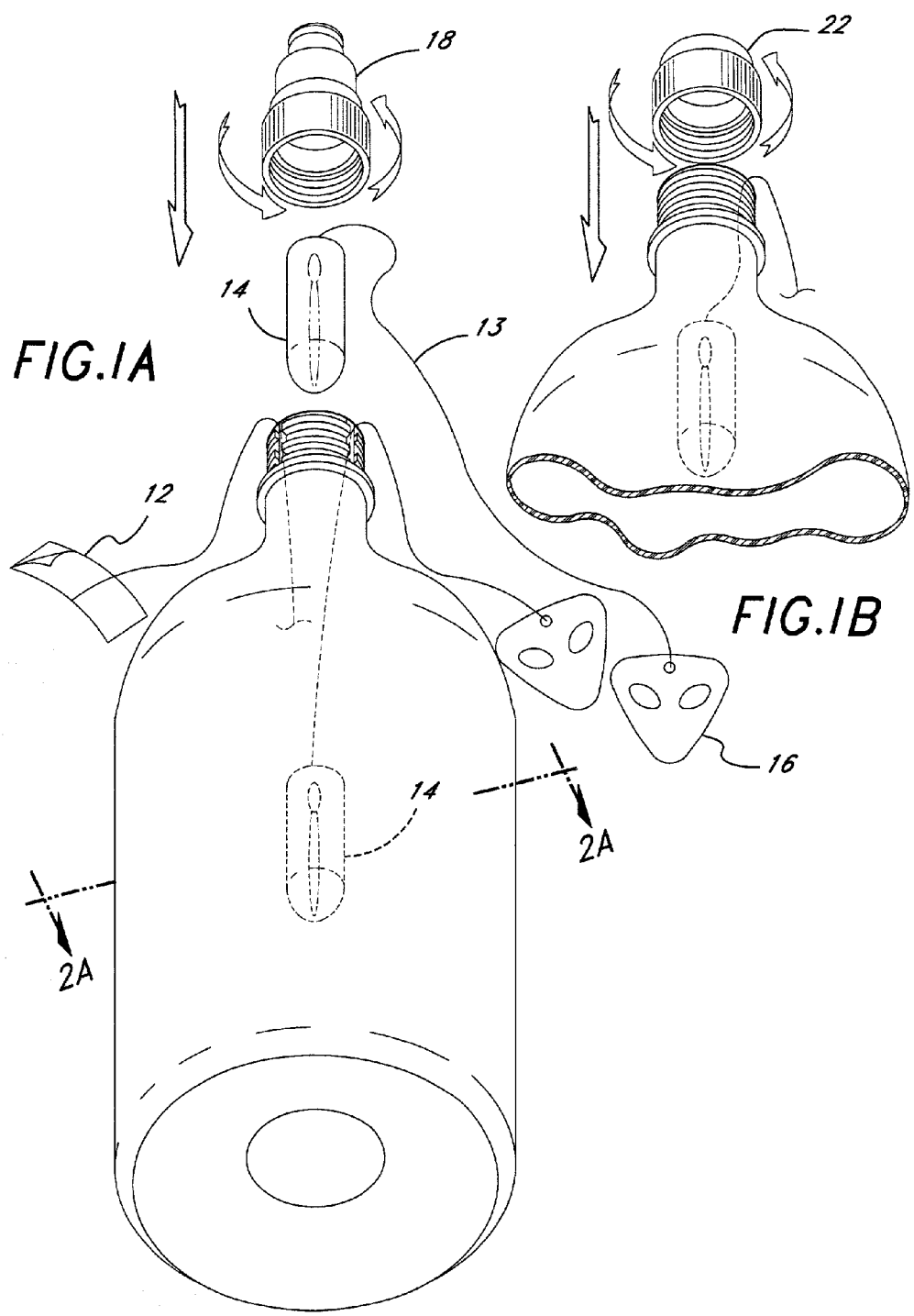

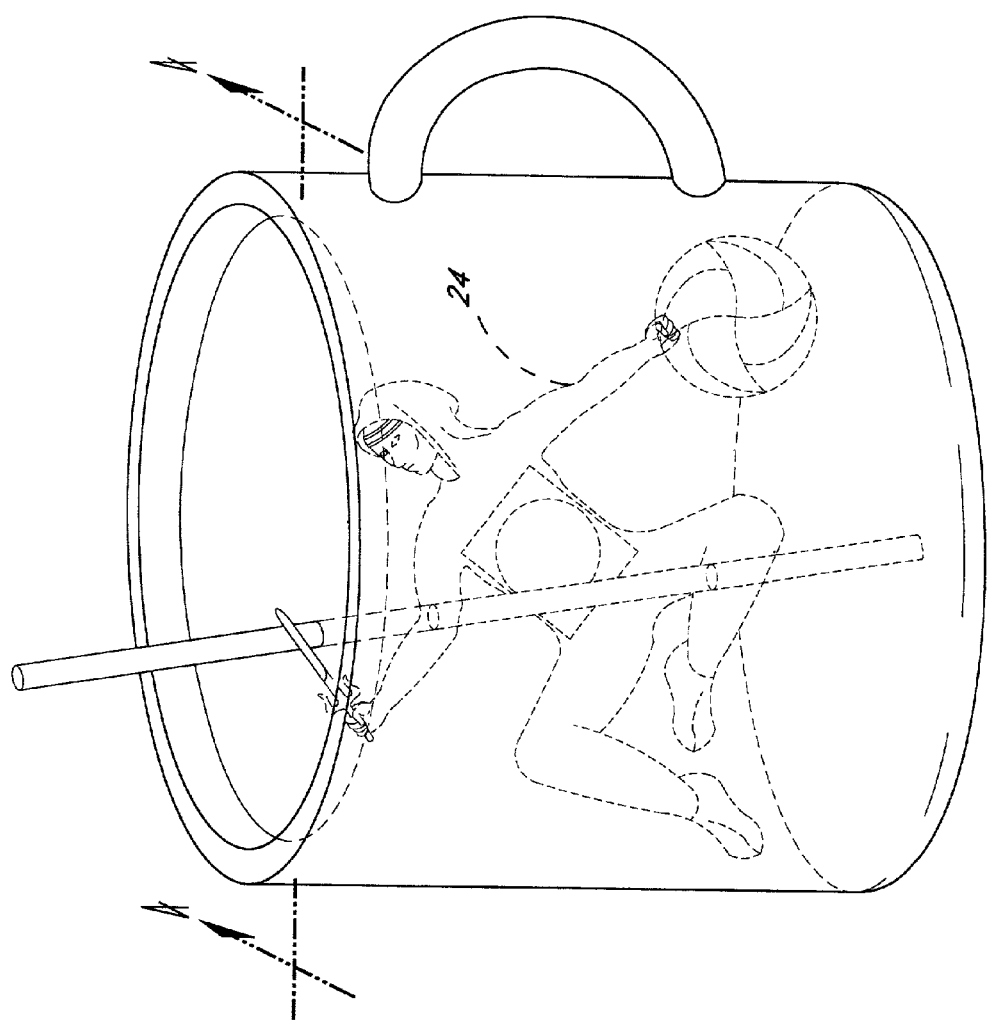

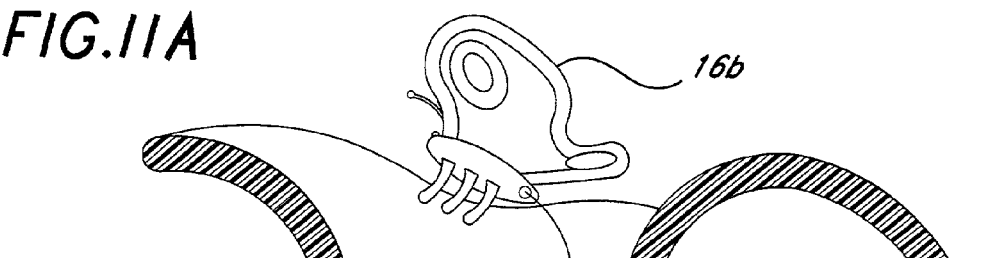
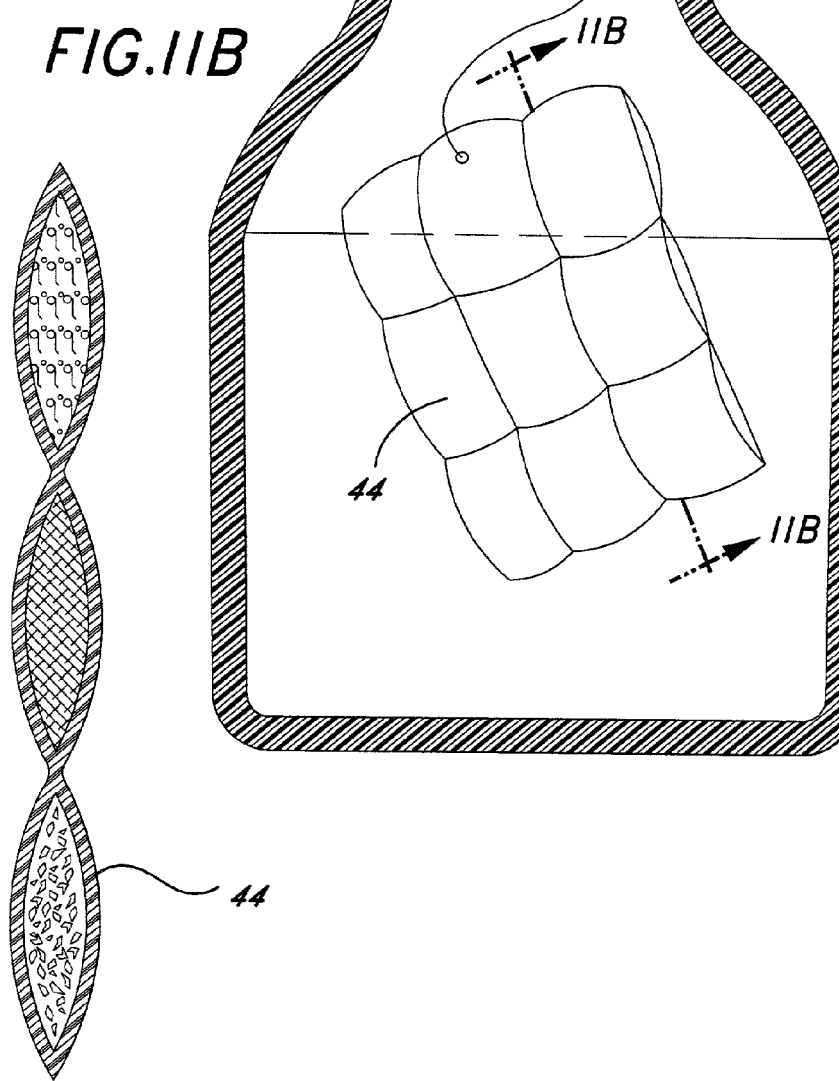

METHOD OF HYDRATION; INFUSION PACKET SYSTEM(S), SUPPORT MEMBER(S), DELIVERY SYSTEM(S), AND METHOD(S); WITH BUSINESS MODEL(S) AND METHOD(S)

The present application is a continuation-in-part of and claims priority from PCT/US01/09171 designating the United States and filed on Mar. 21, 2001 which claimed priority from U.S. Application 60/192,243 filed Mar. 21, 2000; all of these applications are incorporated herein by reference.

BACKGROUND OF THE INVENTION

The present invention relates to providing hydration opportunities for humans and animals.

The present invention relates to a manner in which active and non-active ingredients are delivered orally and/or via enteric hyper-alimentation through a nasal-gastric and/or gastrostomy tube for humans and animals.

More particularly, the present invention relates to a delivery form for beneficial and/or diagnostic agents with or without a support member(s), structure(s), material(s) and/or the like with, the intent and/or designed specifically for permitting such administration with or without functional and/or decorative elements.

Additionally, this invention covers the ability to customize product to better address individual needs, desires, etc. Further incorporating, as specified, various methodologies along with ingredient delivery technologies including but not limited to ones ranging from those that are flash delivered to, and/or those that are governed by controlled release technologies, for humans and/or animals.

Another part of the invention is directed towards diagnostic agents through drinking where by it is possible to present with or without a health-enhancing component, with or without a support member.

Animals, mostly domestic pets, are often forgotten when it comes to supplying, as an example, healthier alternatives. This is not always intentional especially with tight budgets and time restrictive schedules of "working" owners or in the case of large families, etc. The ability to bring to market products just for human consumption alone is most difficult, lei alone for pets and/or other animals.

Further covered is the ability to bring forth the invention with one or more value added and/or value perceived components such as: entertainment, education, advertising, promotions, and the like. An extension of the just aforesaid would be to incorporate active, reactive, and/or interactive abilities through toys, games, contests, which may have manual and/or power operating capabilities which provide movement, light, noise, and the like.

The goal of the invention extends beyond the delivery of ingredients into liquid for the ultimate goal of consumption by humans and/or animals.

The goal of the invention includes business method(s), model(s) and/or opportunities to open new avenues and/or venues of the distribution of product for sale and/or "give for free" product while, alone and/or simultaneously, providing a research and/or test market forum and/or the like.

The inventor calls attention to a line from one of the songs from Fiddler on the Roof, whereby much of the invention is embodied:

"A bird and a fish can fall in love but where are they going to live".

In broad language, this invention represents thirty years of devotion to finding new; novel, creative, ways of bringing health-enhancing scientifically proven and ethical ingredients to the consumer through drinking; and then further expanding the thought as to how to bring the aforesaid to the general public.

While acknowledging the famous bell shaped curve the inventor is desirous of addressing individual needs, and wants, and is further desirous of deviating from the "one-size fits all" approach which, on a one to one basis, this is not that difficult or even impractical. It does however become quite difficult, perhaps even impossible, to take such a concept forward to the general public so that the public as a whole can benefit.

In our society, especially today, it is not realistic, possible, and/or practical to fabricate, mainly a ready to drink (RTD) beverage, to meet a multiplicity of the aforementioned individual needs and/or preferences of any type.

Even if the above were to be accomplished the United States alone is so large without even considering the rest of the world, that specialized production facilities (bottling plants), shipping (size, weight), and stocking in limited valuable venues, an enormous number of special RTD beverages is just short of impossible yet alone practical.

The beverage business is enormous; and so are its subdivisions, such as; wine, beer, soft drinks, sports-drinks, tea, coffee, water, and now new-age categories, etc. In total and/or in part it has an infrastructure of its own which doesn't always allow much room for creativity without a tour de force, a handsome price tag, yet alone the introduction/production/distribution of what the inventor most commonly calls "better health through drinking" concept/principle: make it healthy and make it clean/safe. It is also vital in today's world to make it convenient.

Ergo the following invention: Method of hydration, infusion system(s), support member(s), delivery system(s), and method(s): with business models, methods and opportunities.

Considering that there are many interwoven and overlapping aspects of this invention, the inventor believes that certain background information while maybe not essential will be most relevant for a better understanding of some of the main aspects of the invention. The inventor chooses to present:

1. INFUSION PACKETS: Infusion packets in general, for the foundational understanding;

2. HYDRATION: The importance of hydration, as liquid (mainly water) is a necessary constituent to render the activity of the infusion packet(s) and ultimately the liquid for consumption.

3. SOLUBLE FIBER: It is well known, and accepted in the general health professional community, that fiber is absolutely essential for optimal health. Further dietary fiber, mainly soluble fiber, has been stressed by several health organizations of the Federal Government. The Dietary Guidelines for Americans published jointly by the U.S. Government Department of Agriculture and Health and Human Services, and the National Cancer Institute recommend that all American's increase their daily intake of fiber. Health care professionals conclude that the American diet provides only about half of the suggested daily requirement of 25-35 grams.

4. TOO MUCH SUGAR: The overwhelming need to reduce the amount of sugar, which is so prevalent in today's beverages, is a goal of this invention;

5. COATINGS and ENCAPSULATIONS: A coating may be defined as a layer that covers a surface. Coatings have existed since the ninth century with the introduction of silver and gold coatings of pills in medicine. A fine powdered talcum, called pearl coating was popular at one time, Gelatin introduced in 1838, sugar in France in 1842 and twelve years later in the U.S. And about 1890 enteric-coated pills were introduced. This invention covers any and/or all enrobements, which provide a function even if that function is only decorative. Encapsulation technologies, including but not limited to liposomes, may better serve this invention but coated, enteric coated, encapsulated, and/or any enrobing technology may be used simultaneously and/or individually by design and/or intent. Encapsulations, are important not only for protecting sensitive ingredients, but also for masking certain aromas and negative tasting agents. Further, the inventor believes that the high sugar content of so many of the beverages can be reduced by employing any and/or all of the just aforementioned.

6. INGREDIENT INFORMATION: Information, ergo knowledge, as related to some valuable scientifically proven agents, other than soluble fiber, demonstrating to the reader the importance/need of new delivery vehicles as well as new business methods.

In relation to infusion packets, the background presented is particularly related to tea along with the enveloping material commonly known as the tea bag. The discovery of tea and the subsequent invention/development of the tea bag are perceived to be foundational for a comprehensive understanding of the invention set forthwith.

It is further essential to fully incorporate, and to fully understand, the importance of hydration mainly through the adequate consumption of safe pure water.

Not only are we a dehydrated society but we are a society of overly refined foods presenting very little if any in the way of fiber. While there is both insoluble and soluble fiber, the later is what is addressed here. The importance of water and soluble fiber is detailed in U.S. Pat. No. 6,248,390 to same inventor, Stillman, titled Fiber-Water: Water containing soluble fiber which patent is incorporated herein by reference.

This invention in total and/or in part has been fabricated for use in liquid; more specifically water, and hopefully, when possible, Fiber-Water™. Regardless of the liquid used, and with the existence of Fiber-Water (test marketed under Fiber-Water™ PerformanceWater™ by FiberWater International during the past year and a half) the invention may be so modified as to include, when desired, one or more additional soluble fibers thus adding and enriching the invention Fiber-Water (Performance-Water) and/or water, and/or any opaque and/or clear liquid (mainly water) but also milk regardless of source (cow, goat, soy, whey, etc.), soups, bullion, consommé, broth, stock and/or the like.

1. Infusion Packets

Infusion packets, water permeable coverings containing dried plant materials (e.g., a tea bag), have long been used to prepare infusions of various botanical origins. Tea is probably the most common constituent found in infusion packets.

Of historical note, tea is nearly 5,000 years old and was discovered, as legend has it, in 2737 B.C. by the Chinese emperor, Shen Nong, who was both a skilled ruler and a creative scientist, required all drinking water to be boiled for hygienic precaution. One day as he stopped to rest and the servants began to boil water; dried leaves from a nearby bush fell into the boiling water whereby the brown color was extracted from the leaves and permeated the water. Even the curious scientist the emperor was interested and drank the resulting liquid. He found it remarkably refreshing and so tea was born.

In the 1600s, tea became popular throughout Europe and the American colonies. In 1904, iced tea was created at the worlds fair in St. Louis.

Legend has it that, as tea was an accidental discovery, so was the tea bag. Tea traders, who began selling tea, in silk bags, invented the tea bag. Some customers dispensed with the step of opening the bags to obtain the tea within and simply dipped the entire bag into boiling water to prepare tea. Thomas Sullivan, a New York businessman, actually invented the modern tea bag in 1908. He started shipping samples of his teas in small silk bags for customer's approval. He noted that many customers actually preferred the samples because the tea bags were easier to use than loose tealeaves. The practice of putting tea into tea bags has given rise to one of the world's most creative packaging ideas.

The general notion of the tea bag is that an aliquot of herbal material is placed within a permeable package and dunked into a liquid—mostly commonly hot water. The hot water, and/or a hot liquid, thus allows the various constituents to transfer more easily from the permeable package into the liquid. This is in addition to the egg-shaped, perforated, usually metal and/or ceramic containers for tealeaves to be submerged into cups and/or teapots for the preparation of tea. Further, there exist filtering inserts (usually funnel-shaped members) that are positioned, clamped into a holder and ready to receive the tealeaves.

Tea breaks down into three basic types: black, green, and Oolong, which is popular in China and is partly oxidized. In the U.S., over 90% of the tea consumed is black tea, which has been fully oxidized or fermented. Green tea skips the oxidizing step. Green tea is a staple in the Orient; now gaining popularity in the U.S. and other parts of the world due in part to recent scientific studies linking green tea drinking with reduced cancer risks. U.S. Pat. No. 6,168,795 to Djang (Sante International Inc.) discloses a method for anticancer therapy using an herbal extract composition including green tea.

While flavored teas evolve from these three basic teas, herbal teas, more often than not, contain no true tealeaves. Herbal and medicinal teas are usually created from the flowers, berries, peels, seeds, leaves, and roots of many different plants. The herbal materials placed within an infusion packet are usually selected to impart active ingredients, interesting color, aroma, and flavor to the infused liquid. To this end, flavorful or fragrant materials such as citrus peels, flowers, and/or herbal materials such as mint, and jasmine are frequently used.

However, infusion packets are also known to provide sources of "functional" or medically active ingredients as exemplified by a leading herbal tea company, Traditional Medicinals is a company which produces over thirty different herbal teas to meet a wide variety of health needs. Their product line includes Think-O2 with Ginkgo biloba, an herb proven safe for mental alertness and memory; Echinacea Plus tea for when a cold or the flu starts; Throat Coat contains Pau d'Arco to coat the throat and "a double bang of American Ginseng for an extra big kick".

From the first used tea bag going forward the tea bag has undergone many improvements both in materials to exotic crimping methods for closing the seams without adhesive or sewing. Literature is replete with various methods, designs, fabrications etc. designated to address better infusion. U.S. Pat. No. 5,674,544 to Shakespeare, (Tidy Tea Limited GB), discloses a compressible infusion package using a drawstring method to address better delivery/infusion. Another drawstring method is reflected in U.S. Pat. No. 5,951,452 to Stevenson, (Tetley GB Limited). Another to U.S. Pat. No. 5,989,602 to Drury and Dante, (Lipton) uses a drawstring whereby allowing the tag card to be detached to draw out further portions of the drawstring to contract the packet and squeeze out excess moisture after infusion. It has been noted that most all basically commercially sold tea bags and/or infusion packets are relatively the same shape while sizes may vary. The usual shape is square or slightly rectangle. Recently some round shapes are on the market looking like a filled pancake. U.S. Pat. No. 5,910,247 to Outterside reflects a two element filter bag which includes a cylindrical outer element a generally tubular inner element. Other shapes of noteworthiness are in the flow through category. These are functional having been designed for better infusion and no relation to creative appeal. U.S. Pat. No. 5,366,741 to Van Der Zon (Thomas J. Lipton Co. NJ), teaches a V-fold thus creating a duel compartment tea bag. Another U.S. Pat. No. 5,852,917 to Romagnoli (I.M.A. Industria Machine Automatiche S.p.A. (Bologna IT), titled Method of manufacturing double-chambered infusion bags by folding.

Later came the advent of different materials for the construction of the tea bag. U.S. Pat. No. 5,601,716 to Heinrich and Roland, (Papcel of Gernsbach, Del.), discloses a filter material a composed of both natural and synthetic plastic fibers.

Infusion packets, for the purpose of this invention, might contain tea and/or one or more of the properties of tea but not exclusively whether in the same and/or segregated compartment(s), with or without one or more support members.

2. Hydration and the Importance of Water

The inventor cannot stress enough the importance of hydration. Perhaps best stated by medical description: water is the media for biochemical reactions, is required for expiration, moistens air for breathing, protects and cushions vital organs, helps the body absorb nutrients, removes wastes, cushions joints, carries oxygen and nutrients to all cells in the body and provides an efficient cooling effect. Further, the human body contains between 55-75% water depending on the ratio of body fat to muscle. The human brain is 75% water; blood 92% water, muscles are 75% water, bones 22% water. When dehydration occurs the following symptoms may present: vagueness, discomfort, increased pulse, nausea, dizziness, headache, labored breathing, walking difficulties, twitching, and ultimately when ½ to 2 liters of fluid are lost it can be life threatening. When organs are 5% dehydrated, negative changes begin to occur. A 2% reduction in hydration equals a 7% reduction in endurance. Dr. John Greenleaf, NASA, in U.S. Pat. No. 5,447,730 and additional authored literature addresses the importance of hydration. Dr. Greenleaf further notes that when organs are 5% dehydrated negative reactions begin to occur. The readers attention is drawn to "Problem: thirst, drinking, behavior, and involuntary dehydration" by John E. Greenleaf (Medicine and Science in Sports and Exercise, 24:645 (1992).

A survey of 3,003 Americans, released on May 11, 1998 by the Nutrition Information Center at The New York Hospital-Cornell Medical Center the International Bottled Water Association, found that "most Americans are probably only getting about a third of the valuable hydration benefits they need" says Barbara Levin, R. D., Ph.D., of the center. "The vast majority isn't drinking enough water to begin with, and, to make matters worse, many don't realize that beverages containing alcohol and caffeine actually rob the body of water."

According to the March 1994 issue of the Canadian Medical Journal, studies have shown that an increase in water intake can actually reduce fat deposits. Drinking enough water is the best treatment for water retention. Since water is the key to fat metabolism, it follows that the overweight person needs to drink more water. Although as stated, on the average, a person should drink 8 (eight), 8 oz. (240 ml.), glasses every day the overweight person needs one extra glass for every 25 pounds of excess weight.

According to the Journal of the American Dietetic Association (ADA): Vol. 99, No. 2, February 1999, in the article titled: "Water: An Essential but Overlooked Nutrient": new research indicates that fluid consumption in general, and water consumption in particular, can have an effect on the risk of urinary stone disease; cancers of the breast, colon, and urinary tract; childhood and adolescent obesity; mitral valve prolapse; salivary gland function; and overall health in the elderly."

Further, recent literature brings forth the fact that heartburn may be a cause of dehydration in the upper gastrointestinal tract. Additional literature points to the fact that rheumatoid joint pain/arthritis may be a signal of water shortage in the painful joint. Low back pain and ankylosing arthritis of the spine may be signs of water shortage in the spinal column and discs, the spinal cushions that support the weight of the body. Angina can be a sign of water shortage in the heart/lung axis. Migraine headaches may be a sign that the brain and the eyes need more water. Colitis may also result from a water shortage in the large gut. Asthma, which also affects 12,000,000 children and kills several thousands of them every-year, may be due to a complication of dehydration of the body. High blood pressure, hypertension, is a state of adaptation of the body to generalized drought, when there is not enough water to fill all the blood vessels that diffuse water into vital cells. Both diabetes and elevated cholesterol levels have thought to represent an adaptation to insufficient water in the body. Additional conditions that may be caused by prolonged chronic dehydration are Depression, Loss of libido, Chronic Fatigue Syndrome (CFS) Lupus, Multiple Sclerosis (MS), Muscular Dystrophy (MD), and more.

Dieticians, health care professionals, caregivers, (especially parents) should encourage through education and various activities the desire to design and implement a fluid intake plan.

Thus far, this invention has paid much attention to the general population, much attention to the younger population but not as much focus to our seniors who, at the other extreme, begin to act like children. The inventor is concerned with dehydration amongst this group as a growing population as well and, often times, their lack of desire for hot liquids especially in the summer time. Older people are less likely to drink sufficient water, and hence, are more likely to suffer from dehydration. Once dehydration begins, the thirst response becomes even less effective as one ages, according to Dr. John E. Greenleaf, of NASA, (Medicine and Science in Sports and Exercise, 24:645 {1992}). The reason for this change is not known.

Because the inventor is desirous of providing a vehicle geared towards ensuring proper hydration and the known fact that the invented infusion system must have a liquid, mainly water, to render active, much in the way of a health enhancing liquid can now be produced for the consumer.

U.S. Pat. No. 6,212,959 to Perkins also stresses the importance of hydration noting the following: each person under normal conditions should drink at least 8, (eight), 8 oz. (240 ml) glasses of water a day. This is because fluids are continually lost from the body at varying rates throughout the day, the rate of loss increasing during exertion. Serious consequences result if this water is not replaced in the proper amount and at the proper time. These consequences include fatigue, nausea, loss of consciousness, and, potentially, death.

3. Soluble Fiber

Unquestionably as a society, we are suffering from a deplorable lack of dietary fiber. We are constantly warned by the medical profession, and other experts, that this lack of fiber can, and does, kill. Our diets are replete with "empty"

calories—refined foods loaded with fats and sugars—and contain few whole foods. When it comes to fiber, many believe that a daily bowl of cereal is adequate. Our supermarkets and pantries are stuffed with brightly packaged, overly refined, and prepared foods that are usually fiber-free or very low in fiber. The presence or absence of dietary fiber greatly influences one's ability to expel solid wastes. It has been estimated that about one in 19 individuals in our society has a health condition that requires special attention. In many cases, this makes the need for adequate fiber and water, even more important to these individuals. Due to modern medicine's success in combating contagious disease, and with a better understanding of aging and our ability to address medically the aging process, we are living longer. Nevertheless, can we live healthier?

Fiber or "roughage" is a component of food that remains undigested as it passes through the gastrointestinal system. The vast majority of dietary fiber consists of polysaccharides of plant origin. The most obvious fiber is the cellulosic wall that surrounds plant cells. Many of these cells are actually called "fibers", hence the name "fiber" for this dietary component. However, there are actually two forms of fiber: insoluble fiber—the classic cellulosic material, and soluble fiber—water soluble polysaccharides that are not digested by human or carnivore digestive systems. Both types of fiber bind considerable water and thus, have a softening effect on the stool. However, soluble fiber may, depending on the precise polysaccharides involved, be metabolized or partially metabolized directly by bacteria in the colon. Both types of fibers tend to increase motility within the gastrointestinal tract thus speeding transit time of wastes and lowering the risk of acute and chronic medical problems. Like water, fiber is essential for human health and is not metabolized by humans.

It has been discovered that dietary fiber appears to moderate the rate at which sugars and fats are absorbed from the intestine. The exact reason for this effect is not completely understood. In the case of simple sugars, slowed absorption translates to a more gradual rise in blood sugar following eating. This is important in the managing of diabetes and may also help prevent adult onset diabetes. In the case of fats, the fiber seems to help prevent damaging levels of cholesterol in the blood. This seems to be due to a binding of bile salts and cholesterol to the fiber so that these materials are excreted with the feces rather than being absorbed or reabsorbed. Studies show adequate fiber clearly lowers the risk of heart disease and tends to bind toxins, including toxic metals, allowing them to exit safely from the digestive system.

Soluble fiber is now known to address various forms of cancer such as prostate, rectal, and colon cancer. Reuters (London) Jun. 26, 2001 News report stated: High fiber diet can cut cancer risk of colorectal cancer by 40% according to Dr. Sheila Bingham of the Dunn Human Nutrition Unit at Cambridge, London. Noting the complete study will be published late fall 2001.

Further soluble fiber has been shown to stabilize blood sugar by moderating the rate of carbohydrate absorption from the digestive tract and thereby ameliorate swings in blood sugar. This can also translate to mood swings. Additionally this slowing the rate of digestion (transit time through the colon) serves to curb appetite, prevent weight gain, and prevent obesity.

Soluble fiber is known to retard the absorption of lipids and lower serum cholesterol and triglycerides, thus reducing the risk of heart disease.

Soluble fiber supports the good gut micro-flora and supports regularity thus minimizing the absorption of potentially dangerous toxins (e.g., carcinogens and heavy metals); also, soluble fiber binds to bile salts and help decrease the risk of gallbladder disease, while also serving to support and promote bowel regularity.

Additionally arabinogalactan, a non-starch polysaccharide (NSP), has been classified as a dietary fiber by the Food and Drug Administration (FDA) since it resists digestion by enzymes of the saliva and the small intestine. It enters the large bowel intact, where it is fermented by resident microflora. It is similar to gum Arabic because it is highly branched. Arabinoglactan is produced from Western Larch trees by LAREX™ (St. Paul. MN). Experimental research indicates that it stimulates natural killer cell cytotoxicity. It may be cytotoxic to tumor cells and virus-infected cells, and therefore potentially therapeutic for a variety of diseases. It has already been shown to have properties capable of stimulating the immune system.

Of specific importance to diabetics high soluble fiber intake improves glycemic control, as evidences by decreases in the mean daily postprandial rise in glucose. (The New England Journal of Medicine, May 11, 2000, p. 1392-1398.) Conclusions: A high intake of dietary fiber, particularly of the soluble type, above the level recommended by the American Diabetic Association (ADA), improves glycemic control, decreases hyper-insulinemia, and lowers plasma lipid concentrations in patients with type 2 diabetes.

Soluble fiber comes from a wide range of plant sources. Water-soluble plant pectins and pectic materials, galactomannans, arabanogalactans and water-soluble hermicelulose can act as soluble fiber. Many plant "mucilages," gums, and soluble polysaccharides found in grains, seeds, or stems such as psyllium, guar, oat (beta glucans), astragalus (gum traganth), gum ghatti, gum karaya (Sterculia gum), and gum acacia are also soluble fiber. Algal polysaccharides such as agar or carrageenan also behave as soluble fiber as do other indigestible carbohydrates, such as maltodextrins or dextrins, produced by chemical or enzymatic digestion (e.g., partial hydrolysis) of starch, gums and other carbohydrate polymers. Soluble cellulosic ethers and other derivatives such as carboxymethyl cellulose behave as soluble fiber as do indigestible carbohydrate polymers artificially prepared using bacterial enzymes. Non-digestible storage carbohydrates, such as inulin are also important soluble fibers. A number of companies are now providing an entire range of "soluble fiber" materials. For example TIC Gums of Belcamp, Md., Novartis Nutrition of Minneapolis, Minn. and Imperial Sensus of Sugar Land, Tex. provide soluble fiber compounds of food grade.

Soluble "fiber" is known to provide a novel opportunity for improving the characteristics of fiber-poor refined foods. Fiber was removed from food products because in many cases it made the foods coarse, unpalatable or difficult to process. Adding insoluble bran or other similar fiber to foods may provide more roughage but can also degrade the favorable properties of the foods. For example, cakes or pastries made from flours high in insoluble fiber may have inferior taste and texture. Excess insoluble fiber may upset the digestion and lead to a number of digestive problems.

On the other hand, soluble fiber is generally well tolerated, often improves the texture, and/or other physical characteristics of the food product and is generally innocuous. Consequently, there are a growing number of food products, ranging from baked goods to "shake-like" beverages, contain added fiber in the form of soluble fiber.

Can we not only restore the benefits of fiber, herein soluble fiber, to our highly refined diet but also significantly affect the final product totally and/or in part by the texture and/or the viscosity, and/or the mouth feel of the liquid. This can also be beneficial to the absorption rate and/or flow rate both by mouth and or tube feedings.

These benefits are well known for humans but are also available to animals that have digestive systems substantially similar to humans (e.g., dogs, cats and some other domestic animals). Therefore, the current invention is useful for these animals as well as for humans.

While the invention does not specifically state that soluble fiber, from one or more sources must be present, it is to be considered "a good idea".

The present inventor has realized that a properly formulated infusion packet is the ideal vehicle for administering nutritional supplements such as soluble fiber either independently, and/or with color, and/or with flavor and/or in consort with other pharmaceutical and/or nutritional additives.

4. The Need to Reduce Sugar in Beverages

America is drowning in sugar. The Center for Science in the Public Interest (CSPI) and dozens of leading health experts and organizations have petitioned the Food and Drug Administration (FDA) to require that food labels declare how much sugar is added to soft drinks, ice cream, and other foods.

Most prevalent in beverages today, other than those which are artificially sweetened is sugar and lots of it. Sugar is not on the "good for you" list in our health conscious society today yet the big companies with their tremendous advertising budgets use signage, popular movie, television, and recording personalities to help sell their products especially to a population which is impressionable, doesn't read and/or are uneducated or not responsible.

Further, many of the older population, senior citizens, do not understand this. Many popular beverages avidly consumed by seniors are high in sugar. For the most part, they have grown up with many of them.

5. Coatings and Encapsulations

For further reference on coatings the inventor notes; U.S. Pat. No. 5,024,824 to Edgren, et al. (Alza Corporation Palo Alto Calif.) titled Annealed coats dosage form is disclosed comprising a coat that surrounds a drug. The coat comprises a sub-coat and an overcoat thermally annealed to provide a single unit coat around the drug.

Micro-encapsulation is the process of enveloping certain drugs, enzymes, and the like in polymeric matrices designed to be used in controlled release or delayed release applications.

The International Micro-encapsulation Society, founded in 1995, Glasgow, is dedicated to foster and promote communication and collaboration between amongst science professionals. They define micro-encapsulations as a process that allows liquid or solid substances to be covered by a barrier wall. The wall must be chemically inert to the content of the capsule and possess an adequate stability to mechanical, thermal, or chemical influence. Various barrier wall materials may be utilized during encapsulation, which are dependent upon the application.

Encapsulations, which release their contents within the packet so that the released active is transported across the membrane, may be included. Used this way the shells or the encapsulating material will remain in the packet. A visual might include hatched eggs whereby the little chick goes through the screen/mesh/pores but the shells of the egg remain in the hen house.

Alternatively, the entire encapsulation pass through the membrane intact and release the encapsulated active and/or non-active ingredient(s) into the infused liquid either before or after ingestion of the infused liquid. It is conceivable that there be a combination of the aforesaid and the to be said within one system.

Additionally the encapsulations may be timed released, and even on an individual basis of each encapsulation, so that the ingredient(s) may be released in the mouth, or anywhere along the digestive tract within a specified period, most likely one to three hours after ingestion.

Further the encapsulations, under the aforementioned timed release, may be totally contained within the membrane of the packet and/or partially contained within the membrane in any ratio, size, color, shape, desired relative and/or decorative to the packet and/or to interior ingredients. This would fall under what the inventor calls "best use" of active ingredients. This can also apply to color encapsulations and/or aroma encapsulations as to the formulas just mentioned and to those skilled in the art of.

The Wurster process is a coating technique that is well suited to uniformly coat or encapsulate individual particulate materials. The Wurster process is an internationally recognized coating technique for precision of film coat to particulate such as powders, crystals, or granules.

The coating of pharmaceutical and/or nutraceutical micro-encapsulations helps ensure and/or optimize stability and/or prolong shelf life of active, non-active and/or reactive ingredients.

Capsules may be coated for improved barrier properties. Coating is a most effective way of masking the taste or odor of a particular ingredient, making products more palatable. Enteric coatings can be adjusted most easily to controlled and or timed release for the maximum health benefits.

In the food, industry micro-encapsulations are beneficial especially to encapsulate vitamins, minerals, and functional food ingredients. Additionally noted is that thin or partial coatings are very effective in reducing the caking of certain materials.

For example, Bio Dar was established in 1984 as a United States and Israeli joint venture now under Lyco-Red, Koor Group of Companies. They are specialists in microencapsulated vitamins and minerals for the fortification of food products. Their specialty extends to technologies of how to keep the food additive particle from imparting an undesirable taste to the surrounding ingredients. This technology is most valuable for where the micro-encapsulations are mixed in with the other ingredients. Further, they deal with Carnetine, Amino Acids, Herbal Extracts as well as other nutritional components where the role of micro-encapsulation is to avoid hygroscopicity, and/or minimize interactions and/or eliminate the oxidation of these materials etc. Further, they have the ability to do multiplayer micro-encapsulations for mainly drug delivery. U.S. Pat. No. 4,749,575 to Rotman, (Bio-Dar Ltd. IL), titled Microencapsulated medicament in sweet matrix.

Other patents of reference are U.S. Pat. No. 4,711,784 to Yang (/Warner Lambert; U.S. Pat. No. 5,024,842 to Edgren, Theeuwes (Alza Corp.); U.S. Pat. No. 5,051,261 to Mc Ginity, Chang (FMC Corp); U.S. Pat. No. 5,009,819 to Popescu, Mertz (The Liposome Compar); U.S. Pat. No. 5,653,996 to Hai (Genentech Calif.); U.S. Pat. No. 5,891,465 to Keller (Bio-Zone Laboratories Inc CA); U.S. Pat. No. 6,007,838 to Alving, Owens, Wassef, Nabila (U.S.A. Dept. of the Sec. of the Army, Washington D.C.); U.S. Pat. No. 6,190,591 to van Lengerich (/General Mills Minn.); U.S. Pat. No. 5,922,350 to/Janoff et. al. (The Liposome Company NJ); U.S. Pat. No. 6,174,554 to So (Nestic Vevey, C H) titled encapsulated liquid product; U.S. Pat. No. 6,258,870 to Hubbell et al. (Board of Regents of the University. of Texas Systems, Austin, Tex.) titled Gel for encapsulation of biological materials.

Significant to this invention is that the use of any and/or all types of encapsulations and encapsulation technologies be brought forth to augment infusion systems and/or infusion packets. This technology thus allows the unique combining and vehicle of delivering ingredients solely and/or in combination of hitherto.

As an example, incompatible ingredients so that infusion packets can readily deliver a variety of active agents including stabilized enzymes and similar labile substances. In some cases, the encapsulations can be designed to simply dissolve or burst and release their active contents right into the infused liquid. In other cases, the encapsulations can be designed to leave the packet intact and exist as colloidal particles suspended within the infused liquid. Such suspended capsules can then release their contents at the correct position within the digestive system of the person or animal consuming the infused beverage. Thus, an enzyme or ingredient sensitive to stomach acid would be released in the intestine to do its work in the proper milieu.

6. Ingredient Classifications with Descriptions:

Antioxidants

Antioxidants help to protect the body from the formation of free radicals. Free radicals can cause damage to the cells, impairing the immune system and leading to infections and various degenerative diseases such as heart disease and cancer. Free radical damage is thought by scientists to be the basis for the aging process as well.

The following antioxidants are a consideration of the inventor:

1. Alpha-Lipoic Acid helps to neutralize the effects of free radicals.
2. Bilberry is a strong antioxidant that keeps capillary walls strong and flexible. Supports and strengthens collagen, inhibits growth of bacteria, anti-inflammatory, anti-aging, anti-carcinogenic.
3. Coenzyme Q10 is an immunological stimulant, increases circulation; anti-aging, and beneficial for cardiovascular system.
4. Cysteine (an amino acid) detoxifier of alcohol, tobacco smoke, and environmental pollutants. Anti-aging.
5. Glutathione defends against damage from smoking, exposure to radiation, cancer chemotherapy, and toxins such as alcohol. A detoxifier of heavy metals and drugs, it aids in the treatment of blood and liver disorders.
6. Melatonin is an antioxidant/free radical scavenger
7. Selenium guards the cells of blood, heart, liver, and lungs. It stimulates antibody response to infection.
8. Vitamin C free radical scavenger. It increases the synthesis of interferon (natural antiviral substance produced by the body).
9. Vitamin E prevents the oxidation of lipids.

Other antioxidants include, but are not limited to, Green Tea, Grape Seed Extract, Superoxide Dismutase (SOD), Vitamin A, Beta Carotene, and Zinc. The inventor envisions formulations of one or more antioxidants in combination with any other ingredient to be said or with consideration to all the aforesaid.

Biotics

In addition to the possible inclusion and careful selection as to source and standardization of vitamins, minerals, and herbals, the formulations for the infusion packets will be built around the groups commonly known as fiber, pre-biotics, pro-probiotics, antioxidants, amino acids, and both systemic and digestive enzymes.

Pro-biotics are organisms and/or substances that help to improve the environment of the intestinal tract. Pro-biotics are foods that contain live bacteria and are known to increase milk digestibility, speed recovery from diarrhea, enhance immune function, reduce certain cancers, and lower of blood cholesterol levels.

Pre-biotics are foods or nutrients that are used by specific bacteria and that can be added to the diet to increase the chances of these particular bacteria growing and thriving in the intestine.

The bacteria that live in the intestines make up a very large and very diverse population. The numbers of each kind of bacteria change depending on age, diet, health status, and use of drugs and supplements. The bacteria that do thrive do so because they are able to adhere to the intestinal wall and use the semi-digested food that is passing through the intestines. Because some bacteria have specific nutrient requirements, it has been proposed that adding these particular foods or nutrient to the diet could be a way of increasing the numbers of specific bacteria. This is important not just for humans but for animals as well.

U.S. Pat. No. 6,180,099 to Paul, (Metagenics), titled, "Method Of Using Immunoglobulin And Fiber-Containing Compositions For Human Health" identifies preferred and beneficial human intestinal microorganisms such as *Lactobacillus acidophilus, L. bulgaricus, L. casei, L. fermentum, L. salivaroes, L. brevis, L. leichmannii, L. plantarum, L. cellobiosus, Bifidobacterium adolescentis, B. infantis, B. longum, B. thermophilum,* and *B. bifidum.* More preferably, the beneficial human intestinal microorganism is selected from *L acidophilus* and *B. adolescentis.*

Pro-biotics and pre-biotics are delicate and sensitive and up until recently, have not been able to be handled effectively long-term, without refrigeration. With new encapsulation technologies, especially the new micro-encapsulation technologies available today, we are now able to handle these organisms successfully. Not only are they valuable in human health but animal health as well.

Enzymes

Enzymes sustain life. The late Dr. Edward Howell, a physician and pioneer in enzyme research, called enzymes the "sparks of life". These energized protein molecules play a necessary role in virtually all of the biochemical activities that go on in the body. They are essential for digesting food, for stimulating the brain, for providing cellular energy, and for repairing all tissues, organs, and cells. Life as we know it could not exist without the action of enzymes, even in the presence of sufficient amounts of vitamins, minerals, water, and other nutrients.

Enzymes are often divided into two groups: systemic and/or metabolic enzymes and digestive enzymes.

Digestive Enzymes

Digestive enzymes are secreted along the gastrointestinal tract and break down foods so that the nutrients are more readily absorbed into the bloodstream for use in various bodily functions. There are three main categories of digestive enzymes: amylase, protease, and lipase. Amylase, found in saliva and in the pancreatic and intestinal juices, breaks down carbohydrates. Different types of amylase break down specific types of sugars. For example lactase breaks down milk sugar (lactose), maltase breaks down malt sugar (maltose), and sucrase breaks down cane and beet sugar (sucrose). Protease, found in the stomach juices, and also in the pancreatic and intestinal juices, helps to digest protein. Lipase, found in the stomach and pancreatic juices, also present in fats in foods, aids in fat digestion.

Digestive enzymes are very important on a regular basis. While the body manufactures a supply of enzymes, it can also obtain enzymes from food. Unfortunately, enzymes are extremely sensitive to heat. (Even low to moderate heat (118 degrees F. (48 degrees C.) or above) destroys most enzymes in food, so to obtain enzymes for food one must eat raw foods. Unfortunately, the eating of raw food is not prevalent in out society today. Research has shown that as we grow older, the body's ability to produce enzymes decreases. At the same time, mal-absorption of nutrients, tissue breakdown, and adverse health conditions increase.

The alternative is to take enzyme supplements, which reduce the stress on the body. Today digestive enzymes are available over the counter in tablet, liquid, and capsule form.

It is the object of this invention to provide digestive enzymes, separately and/or in, combination with each other. If they are micro-encapsulated, there is a greater potential for stability and potency. Further, they may be combined with other ingredients to compliment such as peppermint which is know to be good for digestion.

Systemic Enzymes

Many people are familiar with enzymes as digestive aids. In addition it is very important to include the systemic enzymes and systemic enzymes in combinations because many enzymes can also be used to treat a wide variety of conditions through systemic enzyme therapy and/or through the aforesaid use of combinations.

Systemic enzymes can be taken in formulations made with any and/or all sorts of dietary supplements such as phytonutrients, vitamins, minerals, herbs, anti-inflammatory agents nutraceuticals, pharmaceuticals, etc. Again, development and combinations rely on the technologies to best deliver, while ensuring stability and bioavailability to the consumer. From the categories just described and mainly those which are considered "nutritive", (especially phytonutrients those coming from plants), in combination with systemic enzymes form what is called and have been described as Enzyme Absorption System Enhancers (EASE). These combinations are beneficial as they improve the absorption and bioavailability of other nutrients, maximize enzyme activity when combined with these nutrients, reduce the drain of the bodies own digestive enzymes, etc.

In systemic enzyme therapy, the enzymes are distributed throughout the body to help restore the body to health. Some of the conditions which can be treated with systemic enzyme therapy include; arthritis (and other inflammatory conditions), back pain, premature aging, circulatory problems, herpes, injuries, systemic myofacial pain, multiple sclerosis (MS), skin problems, gynecological problems, lupus, erythematosus, and other auto-immune diseases, viruses, and weight problems.

There is much literature on the aforementioned coming from Germany, Japan, and Italy along with the US on the use of enzyme therapy. The inventor calls attention to the fact that in addition to new applications, which are being discovered constantly in systemic enzyme therapy they are being discovered in all categories whereby the delivery system becomes critical. Once again, "If a bird and a fish fall in love where are they going to live"?

Amino Acids

Amino acids are the chemical units of protein. Assuming the reader knows the importance of protein it is not necessary for the inventor to elaborate. It is only relevant from which to go forward. Proteins are amino acids linked together to form peptide bonds. Each individual type of protein is composed of a specific group of amino acids.

In addition to combine to form the body's proteins, some amino acids act as neurotransmitters or as precursors of neurotransmitters. Further, amino acids enable vitamins and minerals to perform their job properly.

For certain effects, and certain disorders, taking supplements of specific amino acids can be very beneficial. When taking a specific amino acid or amino acid combination, it supports the metabolic pathway involved in a particular situation. Vegetarians, especially vegans, should consider taking a formula containing all of the essential amino acids to ensure that their protein requirements are met.

The inventor here forth presents a brief description of some of the amino acids. However, in contemplating the contents of the infusion packet invention one or more may be included. The chemical structure will be the L form. The delivery system used will be the most compatible to ensure potency and stability while realizing that the amino acids are stable at room temperature and decompose when heated to temperatures of 180° C. to 350° C.

With the information presented below it will be obvious to see the possible combinations of fiber, amino acids, antioxidants and the like in multiple formulations.

1. Alanine aids in the metabolism of glucose.
2. Arginine retards the growth of tumors and cancer by enhancing immune function. May benefit those suffering from AIDS and malignant diseases that suppress the immune system. Good for liver disorders, cirrhosis, fatty liver, detoxifying. Useful in treating sterility in men. Important for muscle metabolism. Aids in weight loss because it facilitates an increase in muscle mass and a reduction in body fat. Stimulates the pancreas to release insulin.
3. Asparagine maintains balance in the central nervous system (CNS).
4. Aspartic Acid increases stamina, further it is good for fatigue and plays a vital role in metabolism. Good for athletes. Beneficial for neural and brain disorders.
5. Carnitine is more a substance related to the B vitamins. Main function is to help transport long-chained fatty acids, burned within the cells to provide energy. Major source of energy for muscles. Increases the use of fat as energy.
6. Citrulline promotes energy, stimulates they immune system.
7. Cystein and Cystine help to detoxify and protect the body from radiation damage. Good for rheumatoid arthritis, hardening of the arteries and cancer. They promote healing after surgery and severe burns, chelate heavy metals and promote the burning of fat and the building of muscle.
8. Dimethylglycine. (DMG) helps the body maintain high energy levels and boosts mental acuity. It has been found to enhance the immune system and to reduce elevated blood cholesterol and triglyceride levels. It improves oxygen utilization by the body, helps to normalize blood pressure and blood glucose levels. It may also be useful for controlling epileptic seizures.
9. Gamma-Aminobutyric Acid acts as a neurotransmitter in the central nervous system. It can be taken to calm the body and used in treatment of epilepsy and hypertension. It is good for depressed sex drive and also useful for enlarged prostate, probably because it plays a role in the mechanism regulating the release of sex hormones. GABA is effective in treating attention deficit disorder.
10. Glutamic Acid increases the firing of neurons in the central nervous system. It is important in the metabolism of sugars and fats. It has been known to help to correct personality disorders and is used in the treatment of epilepsy, mental retardation, muscular dystrophy, ulcers, and hypoglycemic coma, a complication of insulin treatment for diabetics.

11. Glutamine promotes mental ability and the maintenance of a healthy digestive tract. It helps to build and maintain muscle; supplemental glutamine is useful for dieters and bodybuilders. It can be helpful in the treatment of arthritis, autoimmune disease, fibrosis, intestinal disorders, peptic ulcers, and connective tissue diseases.
12. Tyrosine is a precursor of the neurotransmitter norepinephrine and dopamine, which regulate mood, among other things. Tyrosine acts as a mood elevator. It suppresses the appetite and helps reduce body fat. It aids in the production of melanin (the pigment responsible for skin and hair color). Supplemental L-Tyrosine has been used for stress reduction. It has been used to help individuals suffering from anxiety, depression, allergies, and headaches as well as persons undergoing withdrawal from drugs.
13. Valine has a stimulating effect, and is also needed for muscle metabolism, tissue repair, and the maintenance of a proper nitrogen balance in the body. Valine is good for correcting the type of severe amino acid deficiencies that can be caused by drug addiction.

Of course, additional amino acids can also be included as needed and/or desired.

In order to appreciate the importance and totality of this invention it valuable not just to acknowledge, as a sample: ingredient discoveries, ingredient matching to specific desires, needs, wants, conditions; production methods/processing; formulations, and or the like whether they be pharmaceuticals, nutraceuticals, dietary supplements and/or the like.

So here we sit with all this material and face the dilemma of how to bring all this to market safely, conveniently, economically etc. so that we cannot only address living longer but also living healthier and more enjoyably.

Hoping not to sound redundant, the inventor once again quotes "If a bird and a fish fall in love where are they going to live"? We need new, novel, and unique delivery systems taking into consideration all set forth by this invention and with a special bent towards being affordable, available, reliable, consistent, and the like especially being conscious of being most desirous of consumer appeal for compliance etc.

Listed below for illustrative purposes of the aforementioned statement, this inventor has selected three scientific, documented issued patents.

14. U.S. Pat. No. 5,849,324 to Dohnalek, et al. (Abbott Laboratories, Abbott Park Ill.) titled Use of indigestible oligosaccharides to reduce the incidence of otis media in humans. Prevention of otitis media (ear infections) in young children is a significant public health problem that has not been solved. The methods that are presently available are limited to practices that; reduce transmission of infectious agents; especially to susceptible individuals. Such methods include provision of clean water (for which this invention supports) hand washing, and good personal hygiene. Additionally, treatment by and large has been with anti-biotics for which we sometimes create another problem, and that is colonizing an individual with anti-resistant bacteria. Note: The development of vaccines has thus far been limited due to the large number pathogens that can cause this disease, and because young children, who are at the greatest risk, often fail to develop effective immunity.
15. U.S. Pat. No. 6,008,253 to Meglasson (The Upjohn Company (Kalamazoo, Mich.), titled Use of 3-guanidinpropionic acid to increase endurance, stamina, and exercise capacity in a mammal. The present invention provides a new food product and use for a known compound. With a careful examination of the Meglasson patent, it should become obvious that by this invention a new delivery system is now possible. The claims include not just what is mentioned in the title but to further treat excess adiposity in a mammal in need thereof; or treat non-insulin dependent diabetes mellitus (NIDDM). Later in the content is mentioned regulating a dosage regimen to the weight of the patient (showing individuality) and sustained release form deliver. The Upjohn Company describes sustained release as a formulation in which the drug becomes biologically available to the patient at a measured rate over a prolonged period. Such compositions being well known to those skilled in the art.
16. U.S. Pat. No. 5,578,304 to Sipos (Digestive Care Inc. Lebanon N.J.), titled, Composition of digestive enzymes and salts of bile acids and process for preparation. Disclosed herein are gastric acid-resistant polymer-coated and buffered digestive enzymes etc. for the treatment digestive disorders, pancreatic enzyme insufficiency, impaired liver function, cystic fibrosis, for dissolving gallstones, regulating dietary cholesterol absorption.

SUMMARY OF THE INVENTION

With advancing knowledge and/or technologies, whether proprietary or not, it is most difficult to get new scientifically proven and efficacious ingredients/formulations, and/or products to the marketplace much less to the consumer.

It is difficult enough with a food yet alone with a beverage whereby the obstacles become even more apparent. Just looking at the size of the United States, yet alone the world, and the fact that RTD beverages must be made in specifically designed facilities (bottling plants) there can, be an enormous cost of shipping or the restricting fact of just local delivery.

Further shelf space is limited and expensive and usually there are stocking fees and many other ancillary costs, which must be factored in. The companies with the infrastructure of owning many strategically placed plants are the only ones that can do so; ergo they then control the industry. This makes it difficult, if not impossible, to enter the industry regardless of how good your product is.

To the aforesaid the inventor is not just addressing how to get the so-called active/beneficial/desirable ingredients in the right form to co-join with the liquid, but how to get the all of this through the "pipe line", the necessary steps, so as to eventually reaching the consumer with great attention to the aforesaid and the to be said. To that the inventor presents and claims business models and methods as part of the invention.

The invention hereafter set forth includes many constituents for which this summary shall provide a brief overview.

17. An infusion packet and/or system designed to promote hydration, by using a liquid, while simultaneously be inclusive of the ability to deliver active and/or non-active agents/ingredients into said liquid for one or more reasons with the possibility of adding non-drinkable/ "spoonable", and/or edible ("swallowable", chewable etc.) and/or non-edible elements. An example of non-drinkable and non-edible would be a support member.
18. Additionally while this invention is mainly designed for the ready to consume market (RTC), meaning the product is mixed/activated and/or the like when the consumer is ready to drink, spoon, and/or the like, it is claimed that an intermediary product can be made.

To produce an intermediary product the liquid may be first enriched, according to the aforementioned, with only a ratio change of product to liquid. It is then possible to make a concentrated liquid, which then may go immediately to dilution, and/or be held whereby the "shelf-life" is governed under the safety guidelines as set forth by the Food and Drug Administration (FDA). It is possible to use, immediately and/or at a predetermined time, such a product to imbibe and/or reconstitute other drinks, beverages, foods, and/or food/like products deemed safe.

Good examples here would be rice, powdered soups, and all the shake and protein drinks etc. that are come in powder form. Gatorade®, as an example; comes in RTD which can be enriched and/or reconstituted when it presents in its powdered format. By this invention, such products as Cool Aid®, and Crystal Lite®, which are not especially known for their health promoting attributes can now become healthier.

19. Using various methodologies, the inventiveness addressed herein is desirous of accomplishing the aforesaid, including but not limited to the use of a support vehicle whether it be named a support member/structure/apparatus/material etc., functional and/or non-functional be it to help facilitate ease of use, add entertainment and/or educational components, and/or the like. There is no denying that what is sometimes referred to as the "bells and whistles" aka added value including but not limited to; entertainment, edutainment (educating element{s}), and or the like serves many purposes. Further provided is the ability to offer advertising and/or promotional advantages in the obvious forms along with active, reactive and/or interactive games, contests, etc. This may be accomplished within the confines of the packet itself, and/or with any and/or all "supports" such as; attachments to the packet, and/or its wrapper, and/or the packaging container, 20. While texture may be part of a design element and may be used, not just for any and/or all commonly known reasons along with and/or without multi-dimensional components it is also to be claimed that texture and texture supporting elements be so designed for the visually impaired.

Braille has become the coined word to describe the written word. Hereafter this inventor expands it to mean any and all distinctions that would allow "feel" to give information especially for the visually impaired be it in word form and/or picture/graphic form and/or the like. This includes the packet itself, tag, wrapper, container, with or without any, and all support members. Often time those with any sensory impairment have heightened sensitivity in one or more of their other senses. Here we would be primarily focusing on sense of taste and touch. A component of this invention is related to promotions, and advertising, etc. it is a perfect venue for companies to market to this population while providing mainly health enhancing properties. The same would be obvious as relating to a toy, game, etc.

It is therefore conceivable to develop products with one and/or more intentions of helping the health challenged, visually impaired etc., while at the same time addressing those that are not are not considered absolutely necessary for comprehension by the visually impaired present.

21. Not just for the visually impaired, but for all of those with health specific needs and/or health challenged conditions may be addressed in a similar fashion, more that just by the design and formulation of ingredients inclusive in the enveloping material(s) and/or by the assemblage of more that one packet, but within the same unit. Considering that one (1) in about every nineteen (19) households have a health challenged individual. This is separate from younger children whose skills are not fully developed and/or a healthy aging individual. It is possible for companies, regardless of size, to factor in those with special needs while at the same time even help them and/or their specific organizations/charities through this invention earn extra monies and/or even a living. While helping themselves they help others. More under business models, and methods.

Diagnostics

A further aspect of the liquid may include diagnostic agents for a multiple of situations including but not limited to those containing radioactive materials. An example of a diagnostic for children would be a beverage that provided needed hydration while at the same time provided a disclosing liquid, safe to ingest whereby the plaque on their teeth turned a different color. To a child this can be fun; for the parent/caregiver informative. Further, this example is very applicable to seniors etc. Additionally, it is possible to add active and/or nutritive components to the just aforementioned for general well-being and/or being condition specific.

Feeding Tubes

Natural catastrophes and emergencies are certainly a source of stress as are medical problems. Numerous and varied medical conditions, both short term and long term, may require feeding an individual through a tube. The two types of tubes used most commonly are the naso-gastric tube and the gastrostomy tube. In either case, nutriment is supplied directly into the stomach. The present inventor is a named inventor on U.S. Pat. Nos. 4,315,513 and 4,393,873 for a percutaneous transport tube with a one-way valve for gastric feeding, and is an expert on the subject of conditions and problems related to tube feeding. From about 1975-1986 the inventor designed and fabricated, on a one to one basis, nutrient enriched liquids for inter-gastric feeding as related to specific medical conditions.

It is important to note that most often feeding tubes are used in a home environment as well as a medical institution.

So while this invention covers all areas of allowing special combinations and mixtures of ingredients for a product to be used in a feeding tube regardless of the base liquid; the inventor pays close attention to the patient. By this, the inventor means the apprehension when the tube is passed in relation to using all aspects of this invention to make it a more acceptable procedure and more stress reducing at the same time.

If in the case of a child, that child might so enjoy watching and/or participating in the mixing of the product to go into his/her tube.

Further, a patient may be encouraged to learn more about his/her condition.

Further, a support member may add joy, delight, even a reward, and/or the like to the experience Further, many tubes on a full time basis and/or are so for a short period of time thus allowing the patient to perhaps take on into life good health habits.

It is certainly understood that what may go into a tube does not have, to be tasted so if there need be a continuation of a specific formulae the product can be re-engineered so that it is acceptable, as example encapsulating some of the not so good tasting agents. (Naturally, encapsulations would always be present if needed for preservation or controlled release of active ingredients).

Every time it is possible to make something more appealing, enjoyable, while considering that it must also be profitable, all avenues should be taken advantage of.

Marketing, Inter-Business Opportunities, Business Models and Methods

Again, the inventor refers to the line from one of the songs from Fiddler on the Roof, "A bird and a fish can fall in love but where are they going to live".

In simple terms we have the bird and we have the fish but where is home? This is akin to how do we get finished product to the consumer in new and novel ways with and/or without many, if not all of the challenges, previously mentioned.

The inventor here has taken on directly the challenge of finding and claiming the aforementioned broadly presented first in summary form as follows:

22. While packaging as related to the below mentioned can be without a reconstitution liquid it can also be assumed that there be packaging with the liquid necessary for reconstitution (mainly bottled water). This can be most advantageous, as you don't have to search for a liquid or have a liquid, and have to search for a packet. In any and/or all instances a support member may, or may not, be included.

The below described, provides for an inter-business opportunity as well as a forum for perhaps selling product in venues not usually known to sell these kinds of things. An example is a toy store where there are elaborate candy toy relationships designed specifically to deliver a candy product. Here presented are beverage toy related possibilities as well. As with the candy, refills can be ordered. Unlike some candy, where just a specific kind and/or company product will work, it is expanded on here that it may function for a platform for more that one developed property and/or company etc. Further, unlike most candy for which an exact shape, size, and/or the like must be uniform for it to function, more operational options are conceived to possibly exist here.

a. This can be in the same wrapper and/or attached by any means known in the art to a single unit of liquid.

b. Further packaging may be in multiple sets as with, example, a 4 pack of water and 4 packets of the same, different but not related and/or different but related (as exampled with a daily supply of RDA vitamins and minerals which might be served/spread over a designated period of time (e.g. 12 to 24 hours).

c. As with a single dose bottle with a ratio of one to one, the volume of the liquid will correspond to the appropriate amount of product. If it is an oversize "family size" bottle, say with 32 oz., it is also possible that there could be just one (1) packet, volume adjusted. As with the volume, this would be considered four (4) eight (8) oz. servings.

d. As with any part of the invention, creativity may play a most important part of consumer acceptability. As an example for children in relation to a "fireman theme": by packing just the packet(s) and/or all the packets and bottles in a fire station, and/or in a fire-truck, and/or in a fire-truck in the fire station as a double incentive.

Certainly, with consideration as to a permanent toy(s) made with the appropriate materials lights, sound etc. can be a part of the creativity, ergo the "inventivness".

Vision; The packet(s) if made with water would make a red colored healthy beverage and perhaps even include information about firemen, and/or the department.

Of note is that if multiple units are packed with the reconstituting liquid, regardless of portion size per bottle, the container for the unit(s) does not have to be metal or plastic. Graphics on a paperboard box, and/or a paperboard box tray, is also envisioned. Further, if it is presented in a tray like form, as opposed to a "closed Carton", it could be with or without a continuation of the concept printed on the plastic covering.

It also provides the opportunity for additional literature, advertising, and/or the like. Literature of all sorts, not just as related to the theme, may be included in any forth, promotion, game, contest and/or the like.

The size may be one serving and/or more based on 8 oz. per serving, and/or perhaps scaled down appropriately, for a child as in relation to age.

In some cases multiple units can be presented without the accompanying liquid, e.g., in lots (number of packets) of 4, 6, 12, 24, etc. They also can be of the same nature (constituents), and/or an assortment of different packets of different natures with, and/or without, the same intent and/or interrelated intent or the like.

23. New and Novel vending machines as well as vehicles for selling product while simultaneously also providing the option for test marketing for the future potential of finding "a winner" to back into a RTD beverage, either made by the same company, and/or licensed, and/or sold to another company, in total and/or in part and/or the like. This is accomplished with the development of a totally new type vending machine, which will dispense a liquid (usually in bottles and primarily water), in conjunction with specially matched infusion packets.

This may involve a new vending machine for dispensing the packets with, and/or without, support member(s) or the reworking of an existing vending machine so that simultaneously, and/or independently, from the same machine dispenses a liquid and a packet (with and/or without a support member) is also envisioned.

Tokens, automatic credits, indicia and/or the like may be used with and/or without the direct delivery of the liquid, (e.g. water bottles) to be fully disclosed and described under details. Basically, it relates to using controlled, cooperative vending machine(s) so that presentation of say a "coded" water bottle will result in the dispensing of an appropriate infusion packet or vice versa. In this way payment can be made at one machine for both products, thus simplifying things for the consumer, as well as the company, and/or the vending machine owners.

24. All eating venues which now serve a cup of hot water and a selection of teas (usually in a basket and/or a compartmentalized box) provide an opportunity for a patron to make an individual selection. Tea bags need hot water for activation, ergo no opportunity is provided for making a beverage for the room temperature and/or cold liquid market; as an example to be used with the ever popular and growing bottled water market (with or without carbonation).

Further, the aforesaid provides the ability to combine more than one packet for delivering, multiple components related to beneficial agents, unique flavor, etc. The inventor believes that while a venue may wish to offer more choices it is not practical to consider this option and offer an extensive amount of choices to a consumer without having to stock RTD bottles and the like.

25. A third large and acknowledged market is the home and office delivery of bottled water and/or equipment to provide safe drinking water. If the invention here is applied, infusion packet(s), and/or system, in part and/or in whole, present an entirely new way of delivering and/or marketing product, and/or for test marketing of new beverage design/concepts is declared.

This leads into a very important concept in today's fiercely competitive marketplace, especially bottled water. In this instance, if the price were the same and a company gave a sample for a drink metered and/or not exactly metered to the water they delivered (assuming some is for cooking), and/or if they deliver individual water bottles and a packet(s) for each bottle, they might generate new business, and/or gain a competitive edge.

The home delivery and/or office delivery people of course, by different arrangement, and/or to the level of being desirous of participation in the now, or future beverage RTD development, can make a company decision.

26. "Doing Right While Doing Good", is a motto of the inventor who has already illustrated by example as related to the visually impaired, how important, it is to not just develop products sensitive by contents and/or packaging, and/or literature, with or without additional support members, but to be considered a part of this invention under a business method providing special money making and character building opportunities through multiple channels.

The inventor under her promotion company, Zen & Wow!, made a best effort to allow general merchandise with unique twists and qualities to be sold by health challenged individuals; sometimes in consort with healthy business savvy people to sell to major corporations promotional items, as well as needed business supplies. This was to be a win-win situation, by which everybody was provided the opportunity of making money and work collectively together. There are large national and international organizations dedicated to specific causes, which could choose to participate, win, also.

It is necessary here to perhaps explain what is obvious but perhaps overlooked. It is the fact that many companies want to help the disabled but don't either know how and/or can provide the opportunity. Yes, they donate funds, but often to organizations with large overheads and thus most of their heartfelt donations do not go to the afflicted individuals who so desperately need it. Then too, donations don't build self-esteem or foster the pride of accomplishment whereby someone has a chance to earn and participate.

The inventor realized that if she did not control her own invention there would be little hope for this to happen according to her vision.

Not only would the invention be made available, but it would be small, light weight, definitely easy to ship if not deliver, and if the product itself was dedicated to healthier drinking for the general public, but most specific designed with a specific need (e.g., diabetes) all the better.

Using any or all of the above options consumers will play a more active approach in the decision making by large companies, and the large companies will have a more through direct interactive response ability to address consumer preferences. This invention also provides new and novel marketing opportunities for good safe ingredients to get to consumers thus creating a win-win situation for everyone.

In summary with consumer acceptance using one and/or a combination of the above new venues, a company has an increased ability to produce/sell and/or test market while simultaneously reducing the failure potentiality of a product(s) for future ready to drink (RTD) products; which may be produced in RTD bottles, cans, boxes, pouches, etc.

Additionally, by supporting any aspects relating to the business method set forth under the above number 5, as pertaining to the health challenged, the large companies have the opportunity of helping far beyond the donation. Additionally they may choose to act as the contractor for the manufacturing by qualifying for the inventor under a licensing arrangement. This also will serve as another valuable test market opportunity for all involved which can then lead to expanding the marketplace for new products with the competitive edge of being out there for sale, or given free, and charting the publics response.

Inclusive of this invention, all aspects of the invention are disclosed in writing and/or in some cases also illustrated with accompanying language that is designed to be comprehensive and/or quite detailed.

In addition, the inventor's position is with the understanding that commonly used words, terms, and/or references there exists a general acceptance. An example would be: if the words "hooked", "clamped", rainbow", "Jack in the Box", "super-hero", Disney" "sound", "light" etc. were used; the inventor is referring to attachments, references, embodiments and like, which are commonly recognized. Additionally; technologies commonly understood, and/or those which may be newly discovered however which are revealed in literature and/or other printed and/or graphically displayed material, included but not limited to the patents referenced, be considered also.

Objects of the Invention

1. It is the object of the invention to provide an infusion packet: and/or infusion packet system comprising of, consisting of and/or consisting essentially of one or more infusion packets whereby each packet may contain one or more compartments of equal or non-equal size and/or shape(s) etc.

2. In particular a system may include a hydration component and/or a support member with the objective intended to impart, in consort with hydration, feelings of well being, improved health, and address quality of life by delivering into liquid, mainly water, ingredients and substances which are needed, liked, desired, etc., and/or the like. A system may or may not also include a diagnostic component.

3. The invention's objectives include but are not limited to: infusion packets with one and/or more than one compartments which may contain individually and/or in combination; aroma, color, pharmaceuticals, nutraceuticals, herbals, pro-biotics, pre-biotics, amino acids, digestive and/or systemic enzymes, anti-inflammatory, diagnostics, soluble fiber(s), and/or any FDA approved dietary supplement(s) by infusing the aforementioned directly into a liquid for immediate use, and/or to prepare a concentration for delayed use by humans and/or animals:

4. The object of this invention is to avoid, whenever possible, the use of pills capsules and/or tablets, and/or provide them when appropriate in the enveloping material itself as a delivery system (or more than one) within a system.

a. Often times they are a reminder of an ill state and/or the like which is not psychologically advantageous.

b. Additionally, often they are swallowed with insufficient liquid, which can cause many additional problems.

c. While some may not like to and/or refuse to swallow, it is of major significance to address those who may have difficulty doing so, (dysphasia). U.S. Pat. No. 6,217,931 to Meister, (Novartis Nutrition Berne, C H), discloses a thickened coffee beverage. It is for those who simply will not consume carriers for active ingredients unless they have a pleasing taste, and/or one or more favorable sensory characteristics.

d. Pills and capsules and the like, unless they have sustained release technologies employed, are considered to be in a bolus dosing category, where as a more constant delivery by sipping and/or drinking over time, may give a more uniform delivery ergo often requiring less of a substance for the same effect. This is most important in cases where there might be agents with known side effects, therefore providing an invention with the purpose to reduce potential unwanted side effects.

e. A compartmentalized packet definitely allows, if needed, and/or desired, the separation of ingredients for which usually a pill and/or a capsule does not. Further, science is finding, and has demonstrated, that many times by compressing, and/or the like, certain ingredients together there is a negative reaction. If provided in the same unit there could be an undesirable example such as with iron, which can rust certain other ingredients. The pill/capsule alternative for this is to just take more pills and capsules, which are packaged and sold separately. This requires a real dedication by the consumer who has to buy all these jars, and keep track of what, and when, etc. Further, certain compression technologies require the need for heat and/or pressure, which is not compatible with the preservation of activity in relation to certain agents and/or formulations, with or without the addition of unwanted materials necessary for the production of the aforesaid.

f. Certainly there is, basically, few or non-existing motivating elements for children to want to consume pills or capsules for health reasons; except if we consider appealing pills such as Flintstone® vitamins, and Bugs Bunny® by Baer, Sesame Street® by J. & J., Rugrats® by Kids Centrum. In fact, the minute kids hear "take your vitamins" they usually run. Children avoid essential wellness enhancing agents especially if they are not feeling well. As has been mentioned but emphasized here, is the fact that there are, at the same time, so many support toys and games promoting the use of candy, such as the game Candyland®, all the mechanical toys formally mentioned and to be later detailed delivering M&M's®.

5. Further, another object of the invention is to present singularly, and/or in consort, one infusion packet and/or more than one packet thus comprising a daily, weekly, or monthly supply dictated by, as example, the recommended daily allowances (RDA) for vitamin and minerals and/or anything that would mirror this concept.

a. This can be broken down by time of day into two or more synergistically designed formulations. It is easy to understand that a consumer may have 2-4-6 or more infusion packets and/or infusion packet system(s) in a daily pack, weekly, monthly etc. with or without a support member. Each can be a separately designed supplement group and travel with the consumer far better than ready mixed bottled drinks. Beyond just the convenience and practicality for the consumer, it allows more products to get into the marketplace and venues to open. Such examples would be airplanes, train stations, ships (cruise etc.), bus depots, truck stops, gas stations, convenience marts, and/or the like.

b. This is presented with and/or without a support member(s), as will be explained below.

c. Additionally, if one wishes to look at a daily regime of proper hydration along with supplementation, it is conceived by the inventor that a daily pack of infusion packets and/or infusion packet system(s) will address this need as well.

6. It is the object of this invention to educate, whereby the consumer may gain a more thorough understanding of his/her condition, increased learning about how to make healthy choices, and the like.

This can be accomplished by pictures, writings and/or the like; any where on and/or within the packet(s), connecting member/support member, wrapper and/or container; additionally and/or acting in consort with inclusive printed material for any and/or all business promoting reasons, (advertising, promotions, etc).

7. Another objective of this invention is to provide a superior product while also taking into consideration all avenues by which to elicit a high degree of consumer acceptance and/or compliance regardless of age and/or health status/challenge and which is affordable in manufacturing and/or purchasing.

It is a given that better taste, in and of itself, creates better acceptability. Aroma enhances product acceptability aim Further, better visual acceptance translates to a greater likelihood of individual compliance ergo consumption. Still further, including an added value component as in, as example, the inclusion of a support member, even as small as the toy in a Crackerjacks box, plays a better violin to the audience.

8. An object of the invention, in itself as an entity and/or in combination with more than one infusion packet and/or system, and/or with the individual infusion system's wrapper, and/or with the packaging container, and/or with any support member, is to optionally include one or more of the following elements: aroma, color, texture, advertising, promotions, games, active reactive and/or interactive entertainment, and/or "edutainment", and/or the like.

9. Additionally many ingredients are more acceptable and better received by the consumer if they are included in the liquid for ease of passage and delivery along the digestive tract into the stomach and below. This may be accomplished with single and/or timed-release delivery.

10. Another object is to provide regulation of concentration. In some instances certain ingredients and/or certain consumers, by nature of their preferences and/or their individual biological systems, need and/or do better if active ingredients are taken with even larger than normal amounts of liquid thus rendering them less concentrated.

11. Another object is to provide a viscosity regulating mechanism. As one example would be the classification of gums with well-researched properties, and/or documented health benefits. An example would be guar gum in relation to the control of diarrhea.

With the technology available, and the careful crafting of product, agents such as gums can present in powder form so as when in contact with liquid, with or without an agitating device, the properties of the liquid change in part and/or in whole as related to viscosity.

12. Another object is related to psychological reasons whereby making something entertaining and/or distracting, especially but not limited to a child and/or a patient in a hospital, is desirous.

Again, this is especially engaging for children who do not, or will not even take their vitamins let alone medicines without a struggle. Parents and/or caregivers often time give in and/or give up when trying to force something upon another. The inventor has many times heard literal fight's echoing from a hospital room over the ingestion of a beneficial agent by a patient.

It is an object of the invention to reduce stress, interpersonal tensions and/or the like by all, involved as related to the just aforesaid.

("When it's in you win, make it fun you won"!)

The inventor has also witnessed and/or found pills and capsules being hidden and/or were hidden under a mattress, in dirty laundry and/or flushed down the toilet.

Using one or more decorative elements and/or support members, especially a toy and/or a game serves also to interest, distract, educate, and/or entertain at the same time as reducing the negative, and reinforcing and/or accentuating the positives.

Especially in a fright provoking hospital environment, all efforts should be made to see that all patients, most noteworthy children, are treated as normally as possible.

13. It is a further an object of the invention to address, beyond the many psychological reasons, the medical reasons as well as to why this is a very valuable medically sound invention with multiple purposes and the added advantage of the assurance that they will be taken with a metered amount of a liquid.

While there has been a great focus in relation to children, this invention no way limits itself to that marketplace. Further, in no way does the invention limit animals along with their owners, who have to use all kinds of trickery, to get the animal to co-operate. (What pet owner has not been faced with how to get a tablet into a pet?)

It is important however, that while this invention is for everyone certain considerations will be given to the various segments of a population as delineated by age. Teenagers pose one set of compliance friendly challenges and the aging population, senior citizens, "seniors" another. As related to seniors:

a. Aging seniors who do not want to take so many pills, etc, b. With aging comes the loss of one's thirst mechanism, ergo seniors may not get enough hydrating liquid.

c. Many seniors are used to packets they recognize as tea bags. So herein lay the opportunity to add all the extra benefits, regardless of form and/or number; governed under this invention to the just mentioned familiar tea and/or tea bag-like easily recognizable object. Now it is not only possible, but often desirable, to use this invention. As a psychological advantage, a patient might not feel as if they are so ill as when they have to take so many medications. Also, whereas if they were directed by a health care professional to take a pill, they would not do so and/or pretend to do so and then hide, or flush it down the toilet, etc. just like a child. While the inventor believes that information is important, many just can't absorb it and become fearful, especially the aging. To prevent confrontation and tension in this age group as well, caregivers hope for delivery systems in which there is the opportunity to mask, not just the taste, but also the active ingredient(s) so as to reduce questioning by the patient. The inventor has first hand experience with her 90 year-old Mother in relation to on going cardiovascular problems needing attention daily.

d. Further, using seniors they have problems often times with gastric upset and/or other digestive disorders whereby in the wrong form and/or too much entering the stomach too quickly and/or without adequate fluid may become problematic.

14. It is further an object of this invention to expand the possibilities, availabilities, and the like, that any one venue can offer its users.

a. It would be difficult and impractical for a hospital, or any location place where RTD drinks are available to keep in stock such a myriad of combinations, for which the present invention can make, readily available. This invention addresses that issue most efficiently not only to accommodate taste, flavor, sweetness, and/or likeable combinations but, additionally, by ingredient functionalities.

b. Further, stocking multiple RTD formulae may not be achieved even if practical, due to the sensitivity and/or stability of specific ingredients.

15. It is a further object to be able to provide a participation experience, an interactive experience, for the consumer whether in a water bottle and/or a glass/cup/goblet and/or the like.

16. Another object is to reduce the acids, preservatives, and/or any and/or all unwanted additives and/or chemicals needed to produce a typical RTD beverage.

As we know, there exist strict FDA bottling guidelines to which all companies must adhere. With the present invention, one can prepare, using water, a drink(s) that reduce and/or eliminate altogether the aforementioned that would ordinarily be included, and/or necessary, in a RTD product to offer protection from potentially harmful pathogens.

Enriching other than water beverages with nutrients is also provided without the need for added sweeteners, and/or acids, and/or the like.

Further one could reduce the caloric count as the consumer can, by this invention, control, as example, the sugar load and/or the type of sweetener used should one be desired.

Sweetening agents can be used in combination and/or in any ratio thus combining both natural and/or artificial calorie reduced agents and/or non-caloric agents as suited to individual taste, and/or intention. This ability can be most valuable to diabetics and those on weight control programs.

17. Another object of this invention is directed towards a variation of the just mentioned. This goal is for the specific purpose of providing a beverage with reduced sugar because often more sugar is needed to overcome the acids let alone sweeten the beverage.

When you deal with a RTD beverage, you're totally at the mercy of a predetermined amount of acid as well. With the invention set forth herein if a less acid beverage is desired it is under the control of the consumer, who can now make a beverage with little and/or Possibly no acid(s) because resulting beverage does not need a shelf life. The inventor strongly believes that much unnecessary acid, and/or potentially harmful acid, and/or acid combinations cause and/or provoke existing digestive disorders and/or gastric upsets.

18. An additional object is to provide freshly made/formulated drinks taking advantage of many potential combinations and formulations and delivery technologies.

19. A still further object is to overcome the traditional drawbacks of packets that are loosely filled, like sugar. Certainly, it is easily understood why there is a filtering mechanism when herbals and/or tea-like constituents are used. It may become less apparent when ready to mix ingredients are supplied in powder, granule, crystal, etc. form. All one would have to do is tear open the packet and pour the contents into liquid. While this may be an effective method in some instances, it does not come without serious drawbacks.

a. Such drawbacks are that the contents might spill and create a mess. This is especially noticeable if one is trying to pour the ingredients into a narrow neck vessel like a bottle.
b. Further, much is left to the consumer as how to open a packet. The packet can be torn and/or cut etc., and the consumer does not always make the correct choice.
c. Additionally some of the contents may remain stuck in the packet and therefore not be available to the liquid.

20. The object of this invention is to be sensitive to all those, especially children, seniors, and those who have manipulation problems, as related to hand dexterity and/or perceptual problems such as eye-hand coordination and/or the like, and even individuals with health challenges such as a paralysis and/or loss of a finger, hand, or arm.

21. Further, the inventor has many additional individual goals to accomplish with the invention, such as:
   a. Opening a packet whereby you have only one compartment does not allow for the separation of ingredients prior to aqueous mixing. This can be most critical in those formulations where the ingredients are not compatible for a myriad of reasons until they are ready to be digested.
   b. Providing separate compartments to accommodate separate ingredients is often critical because if they were in one compartment they may interact unfavorably. To provide a longer shelf life for specific ingredients which, may be in the same packet but not for as long of a time. Further, separate compartments might add to the entertainment factor. An example might be Cowboys in one, Indians in the other.
   However, the reverse may be also true, by being in the same compartment they may positively effect each other by ingredients, and/or design. They can look like zoo animals for kids.
   c. Further, having a portion of a specific amount of material enclosed within an individual compartment of an infusion packet further ensures a potentially more sanitary delivery into the liquid. This is especially valuable for children, and even adults, who do not clean their hands prior to touching many foods.

22. Any time there exists an RTD beverage and/or a beverage to be re-constituted, it is possible to add an enhancing agent by means of this invention, and in the appropriate format. It is now possible to make enriched drinks richer, and those with little nutritional value more nutritionally valuable.

While the sports drinks like Gatorade® Power Aid® etc. claim much in the way of an isotonic beverage enhanced with minerals, they can always serve as a platform for individual modifications especially since many of these types of beverages are used by athletes; who just like anyone else, may have special personal needs.

22. Another object of the invention having to do with the specific packet, is to be sensitive to all health challenges as exemplified by use of Braille for the visually impaired.

Certainly, this condition demonstrates why a general packet that could spill all over the place is not a good idea.

Then with a tag and/or a connecting member it provides that particular consumer with more feed back as to what is where and/or the like.

Later will be addressed a packet for use in water bottles and/or narrow neck bottles so this will further help someone who has no vision or limited vision.

23. The packets are perfect for travel, especially where space is restricted, and especially valuable for those who travel often and/or as part of their job:
   a. Airline; in flight personnel, also noting flight cabins are dehydrating themselves;
   b. Schools; and/or for kids for school lunchboxes along with a small bottle of safe water;
   c. Camping;
   d. Emergency sponsored venues and emergency packs especially with the presence of fiber; and
   e. All Military installations and bases;
   f. Truck stops;
   g. Train stations;
   h. Bus depots;
   i. Gas stations, mini-marts;
   j. Cruise ships;
   k. Confined resorts like Club Med®;

24. It is the object of the invention to offer a compressible delivery system, whereby a packet, much like a sponge, the packet will absorb, part or all the liquid into the system and then by using a squeezing mechanism, attached to or separated from, the resulting beverage would be formed.
   a. This would very much resemble a compressed sponge that is filled with active ingredients whereby the sponge would absorb the liquid and a support member would be used to squeeze it out.
   b. In the kitchen, we often use a dry sponge mop, which we submerge in a pail of water/cleaning fluid and then squeeze out the sponge into the pail.
   c. Only here, we are not cleaning the floor we are releasing ingredients into the liquid for drinking.

25. The object, of the invention is in relation to a sponge and/or sponge-like material; described and illustrated later; the just said will be impregnated with active ingredients and may be so constructed in such a way that the ingredients, whether encapsulated or not, release automatically, float out, into the liquid, simultaneously enlarging the sponge and/or sponge like material whereby a shape and/or a specific function presents itself. For example, if the sponge is used in a bottle it should swell, and/or otherwise*change form, so there is no danger that a child drinking from the bottle might inadvertently swallow the sponge and choke on it.

26. Flotation is always a consideration with tea bags especially.
   d. Therefore, a weighting feature can be provided when desired. Flotation has been observed often by those whose business is tea, the making of tea bags, and/or the like. It is here noted, that teatea bag, where the ingredients enveloped are very light, as is the bag, and therefore-buoyancy is probable and/or noticeable.
   e. b. This invention addresses that in several ways. First, the bag itself maybe made of a material that will prevent floatation by weight, which renders the bag heavy, and/or any other implementation mechanism as dictated by the fabric of the envelope and/or imbedded and/or implanted.
   f. The actual format of the ingredients delivered within the envelope may be delivered in a manner sensitive to the issue of floatation should it not be acceptable and/or desirable. As an example, the ingredients maybe so formed as in a big tablet and/or any other form whereby buoyancy is avoided.
   g. Further, proper fabrication can elicit a sink then float (bobbing) effect as the ingredients disperse into the liquid.
   h. If effervescence is used, and/or if the ingredients go into a liquid with gas or carbonation, various changes in buoyancy can be obtained.

27. It is the object of the invention to present various compartmentalizing concepts, methodologies, along with proven technologies by which to implement.
   i. As an example: the packets can be similarly compartmentalized to control the interaction of the active ingredients contained within.
   j. Mixing within compartments is not a new concept within certain industries such as cosmetics and/or hair care products. In the beverage business, the inventor calls attention to U.S. Pat. No. 5,772,017 to Kang titled Beverage mixing dispenser device; another U.S. Pat. No. 6,280,075 to Cadeo titled System for continuously preparing at least two different liquid foodstuff mixtures; another U.S. Pat. No. 6,263,923 to Castillo titled Device for maintaining separate ingredients in liquid food products.
   k. The packet may be equipped with one or more separate compartments for the single-unit dose per compartment regardless of form. The active and/or accessory ingredients (color, aroma, etc.) may be mixed or separated in different compartment as desired and/or required. It is possible for the components in each compartment to be delivered in a different form as dictated by the nature of the ingredient and/or the desired effect and/or result. The components may be in dried form (powder, beads, granules), liquid form, gel form, tablet form, capsule form, encapsulation form, and/or any form, which may, or may not, contain effervescence so long as it is handled properly.
   l. The packet itself may be specially sized and shaped for insertion into a water bottle or similar device. In such a case, the tag can be adhesive backed for attachment to the outside of the container.
   e. It is also possible to use a form of a gelatin capsules and/or tablets that have constituents designed for rapid dissolving. U.S. Pat. No. 4,804,542 to Fuscher (R. P. Scherer GmbH, DE) titled Gelatin capsules and methods of preparing the same. U.S. Pat. No. 6,221,832 to Casteel et al. titled Compacted granulate, process for making the same and use as disintegrating agent for presses detergent tablets, cleaning agent tablets for dishwashers, water softening tablets or scouring salt tablets.
   m. To facilitate better use and/or for fun and enjoyment it is conceived that effervescence be used. Effervescence can be defined as the evolution of bubbles of gas in a liquid. It is noted that effervescent ingredients are often extremely hygroscopic and that the packaging material must meet certain parameters. It is most important that the integrity of the effervescence would be maintained, and thus, most probably a special outside wrapper would have to be fabricated. Then and only then could effervescent powder, granules, and/or a tablet be considered. U.S. Pat. No. 6,071,539 to Robinson (Ethypharm, SA, FR) teaches effervescent granules and methods for their preparation. U.S. Pat. No. 6,279,505 issued to Plester, Horst, Rule, Pickel, Humele, (The Coca-Cola Company, Atlanta, Ga.) discloses plastic containers with an external gas barrier. The object here is to provide a container with low permeability to gases and vapors.

28. The wrapper is to be considered anything and/or out of any material that protects the infusion packet according to the guidelines of the ingredients, and/or augments the value of the infusion packet/system.
   a. The wrapper may take any form so long as it conforms to the intention.
   b. The individual wrapper may unfold in such a way as to become the tag.
   c. It also is subject to all the design and fabrication technologies as well as color, aroma, and/or the like.
   d. The wrapper can bring forth print material and actually serve as a miniature billboard having to do with the product and/or, as in a cross promotional be used to advertise and/or promote.
   e. In some instances, it is necessary that the wrapper be airtight.
   f. The inventor here believes that a clear coating be applied to either the inside, outside, and/or both sides of the wrapper to insure preservation of effervescence especially if desirous to view the enveloping material, regardless if it is transparent or opaque.

29. It is an object of the invention to better address the ubiquitous tag/tab/fob that may or may not be needed and/or present. The tag of the infusion packet is enhanced in a number of ways by the current invention.
   g. They can be made from a variety of materials, synthetic and/or non-synthetic such as papers, plastic, metal, etc.
   h. They may present in a variety of shapes and sizes and, perhaps with few modifications, generally follow much of the guidelines as set forth by the invention.
   i. They may be flat, have raised parts, and/or exist in three-dimension (3D). They may be decorative only or serve a function.
   j. Tags can be toys or favors;
   k. They can be puzzle or game pieces;
   l. They can be collectables and/or "tradeables" such as baseball cards;
   m. They can be a prize in and of themselves, and/or part of a prize that is completed when the, as an example, the entire container is finished. What an incentive to a child to drink healthy. As an example, each fob can have a part of a toy clown that snaps together.
   n. They can have a functional value, as a charm for a bracelet and/or a clip for the hair, and/or the like.
   o. They can carry forth the ability to serve as advertising and/or promotions directly for the company that produces them, or a cross promotion with a compatible entity.
   p. They can be bigger than the packet and/or smaller.
   q. There can be one or more tags, like keys on a key ring.
   r. They can be permanently attached, or easily removed with a clip or a hook on the end.
   s. One side can have an adhesive member which, when detached from the packet, can be affixed to say, a storybook. As the child goes through the container with the story/picture book, the youngster will add the picture to the appropriate space allotted. Much like a postage stamp. This can also resemble how kids like to collect and trade stickers.
   t. If the tag has a scratch and sniff modality impregnated within it and/or when the adhesive is peeled back then we add one more learning experience and/or reinforcement.
   u. The tag may be dissolvable and/or follow all the guidelines set forth by the enveloping material.

30. An additional object of the invention addresses the enveloping material; what is its fabric-synthetic and/or non-synthetic, unique properties and/or abilities, form, shape, color, functions, release abilities, and/or the like.
   v. This invention presents enveloping material of the infusion packet whereby the function of the packet(s) and/or system may be enhanced by providing soluble, or even edible, enveloping materials.
   w. Further, the appeal of the system can be enhanced by providing clear "see through" enveloping materials, either used for the packet that holds the active ingredients, and/or the protective covering for the packet. Noted is the fact that any and all materials used may display various printed designs either which may display continuously, dissolve totally and/or partially into the liquid, be revealed on the material in response to wetting, and/or react to changes in light, and/or with temperature.

31. The invention is concerned with contents of the infusion packet whereby specialized health-enhancing ingredients—in particular soluble fiber(s) of different sources—are added to the infusion packet(s) system. There are certain fibers that may be incorporated into an edible film. The reader's attention is directed to PCT/US01/05630 with a filing date of 22 Feb. 2001 to inventor Stillman along with the issued U.S. Pat. No. 6,248,390 titled FiberWater-Water Containing Soluble Fiber.

32. A new component, hereafter called a support member, is defined broadly as: anything(s) made of any material(s), and/or comprised of any amount of different materials, attached and/or unattached, which adds actual and/or perceived value to the purpose of the invention and its acceptability, attractiveness, usefulness, and/or the like.

x. One or more infusion packets and/or infusion packet systems with or without the packaging container may or may not include an additional support member that is intended to support the ease of use and, independently or simultaneously, including one or more decorative, functional, entertaining, and/or educating elements.

y. Within a container holding the infusion packets and/or infusion packet systems, with or without a support member, there may be extra items necessary to execute an extracurricular active, reactive, and/or interactive objective such as a game.

EXAMPLES

25. A support member may be a tool that holds the infusion packet for proper placement in liquid. It may be attached to the packet, and/or serve as the connecting member, and/or both.

26. A support member may also be the packet in several ways, with an example below using a wider than normal diameter straw, —follows:

a. A perforated straw, which contains the ingredients and/or serves as a stirring tool and/or a useful utensil for drinking after the beverage is prepared. It will have by necessity, a larger than normal diameter with multiple holes, more than likely, placed along the bottom portion of the shaft.

b. The inventor thus believes that the ideal vessel would be a bottle. If the straw is used for drinking as well, the following must be kept in mind. So long as the holes in the straw are below the liquid line of the beverage (most probably in a bottle) then the straw will serve its function.

c. The "straw" will contain the ingredients to be infused with particle size(s) larger than the perforations.

When placed in a liquid whereby the liquid line is above the pores the contents will eventually liquefy to infuse into the liquid.

d. Stirring with the straw will, more than likely accelerate the release of the contents of the straw into said liquid.

e. Further, the inventor draws attention to the fact that different shapes may be used, however the most likely are spheres, as the straw is usually a cylinder which contains the active ingredients. The active ingredients may dissolve totally, and/or not totally, or at different rates. It is possible to have a straw be square, triangular twisted to a shape, and/or coiled, etc. by specific design.

f. To this end it can be most pleasurable, to drink part of the drink before all the, most likely sphere shaped, ingredient(s) enriched, objects dissolve.

i. If designed as such these spheres can be both nourishing and fun to use.

ii. 2. The straws are easy to transport and/or to dispense in a vending machine that also sells bottled beverages, mainly water.

iii. 3. They can be made in designated and desired varying lengths and diameters. They can be large encapsulations that partially and/or totally break down.

27. The support member may also be used to combine one or more separate packets into a functional unit with and/or without another support member such as a toy and/or a game.

a. A toy can be used as a game, as an example; a set of packets supplied with an old fashioned, everybody knows, "Jack in the Box".

i. With a slight modification, "Jack" can have hands that are fashioned to hold a packet.

ii. Of note: Jack can come packaged with any number of packets alike in contents and/or assorted/different. (Naturally, the reordering of packets is an option).

iii. As a game to encourage children to drink and/or as a beverage packet plus a reward, which Jack will bring forth, and especially for a child who is sick and who needs nourishment and does not get enough liquids this is a God-send.

iv. Sometimes Jack can come up empty, and sometimes with a little message, and/or with the packet b. Envisioned also is to develop a character called Packet-man.

28. The support member may also be used to combine one or more separate packets into a functional unit, like cherries in a cluster and/or grapes on a vine, rungs on a ladder etc.

29. The inventor always gives much care when it comes to children. Children delight in surprises, and certainly, this invention plays to that delight. Similarly, the infusion packet and/or system itself can be incorporated, into a toy like object, and/or bring forth some other magical elements, and/or some other attractive object(s). In this situation, the packet can carry printed indicia etc. to amplify this point.

a. Children like magic and therefore here conceived that within the folds of material which would be folded, based on the Japanese art of Origami, ingredients be placed. Then when the child drops this folded shape into liquid it would release ingredients simultaneously as the transformation took place. The enveloping material will now present as a swan, bird, fish, etc. in the liquid.

b. Without being just in origami-form it is possible for an ordinary shape to, when wetted, change. When wetted and/or submerged and/or in the presence of a larger quantity of liquid as in a cup, glass, bottle etc. change to reveal a totally unique shape.

c. A folded and/or rolled enveloping member, regardless of how arranged and/or constructed, is conceived so long as the enveloping material comes in direct and/or partial contact with ingredients whose concealed identity is unknown, not revealed, until wetted, and/or submerged is illustratively described here. U.S. Pat. No. 5,284,667 to Zimmerman, et al. (General Mills, Inc. Minneapolis, Minn.) titled Rolled food item fabricating methods.

d. Just as an illustration, the inventor is using a heart. The shape can be a rainbow, star, moon, sun, and/or any recognizable object that is commonplace in our society.

i. An example here is where the inventor visions a folded enveloping member, which is red, and/or becomes red upon contact with wetness.

ii. Either by expansion technologies, and/or unfolding developing technologies, a heart is revealed. This heart may also reveal a "heart" warming message inside due to the preprinting but concealed in the folds, and/or revealed with the wetting of the material . . . much like the books one has as a child whereby you painted with water and colors and/or graphics, and/or messages (writings) which "magically" appear.

e. In any; and/or all of the above ways, clues can be revealed, answers to puzzles, horoscopes, lottery numbers, jokes, holiday wishes, etc.

f. While in the invention above one does not know until wetted what is to be revealed, a variation is that the shape be known but the message remain secret. Further the shape may be known but the color(s) be not revealed until wetted. Great enjoyment would be, if this were to be a rainbow.

g. If the shape is not clearly obvious, then there can be a writing or a poem in it giving a clue and/or clues. An example, as pertaining to a rainbow might be: "what comes after the rain and is made up of colors?"

h. Any, and all of the above can come with or without an attaching connecting member, tag, and/or any part of the wrapper, container, as support, which is covered in this invention in total and/or in part.

30. While it may seem that the above is dedicated to young children, it is not meant to be exclusive to their age group. Teens have their idols, heroes, etc. and if so licensed, as an example, a real pop up Elvis, as an example, could emerge. Young adults as well as aging seniors have things they relate to as well.

a. Alternatively, words, and/or design, and/or color may dissolve off the packet in whole or in part into the liquid and go undetected in the liquid. This can be most fun for children as they may see their favorite character slip into their drink and literally disappear; and/or the just aforesaid may slip into the water and color the water/liquid.

b. Not unlike polished stones we see today in the stores which have inspirational words, like the word "believe" carved into them and/or messages such as "an ounce of prevention is worth a pound of cure" on wooden plaques these same words/messages may wash into the beverage.

c. Additionally, in the reverse, when the infusion materials come in contact with the liquid, graphics, and/or secret messages, and/or clues can be revealed.

31. Teens can have great drinks with contest questions as related to the latest in, recording by their music idols, movie heroes. If posed in a contest and win, according to the rules set forth by the contest: they get an opportunity to win prizes as offered by the manufacturing companies and/or the like.

a. Teens can participate in designs, etc. all for reward.

b. This brings the company closer to the public and fosters bringing big business closer to the people.

c. Collecting a specific number of tags and/or a portion of the product may make one eligible for prizes and/or redemption monies. This is under the control of the FTC.

32. The inventor also conceives of a box of assorted samples, not unlike the famous Whitman's Sampler, whereby each piece is individually wrapped, and/or segregated in a container.

a. Sometimes when you look under the positioned candy, you will find printed a title (name of the piece).

b. A variation here is claimed for the ability to package an entire selection of infusion packets, which may and/or may not relate to a central theme. As an example all the characters of a Disney® movie, Star Wars®, an historical event, a city and/or a state, theme, etc.

c. The latter is an ideal product for sale in airports, which are so known for selling city/state/university and/or team (football, basketball, baseball) memorabilia.

33. While it is envisioned that each packet of the above be designed for a single portion of hydrating liquid, (mainly water) it can be so designed whereby two or more packets Will be necessary for that 8 oz. portion.

34. Attention has been given above to the possibility of mixing an intermediary product, that is, one that is not used right after drinking and/or mixed and held as with a concentrate and/or any combination whereby the drink is not consumed immediately.

35. Here is an example whereby an enriched liquid may first be made and then go into reconstitution, say a dry mix using as an example in relation to mixing the dry form of Gatorade® developed for athletes.

Another example of the just aforementioned, U.S. Pat. No. 6,214,390, issued to Weinstein, Weinstein, and Schmier, addresses an assemblage of nutrient beverages and regimen for enhancing convenience, instruction, and compliance, with exercise supplementation. Therefore, in this invention there exists a pre-exercise and a post-exercise formulation in dry form.

There are many other, powders on the market with beneficial ingredients, which call for a reconstituting liquid, water, a milk product, and/or a juice, and/or a combination of one or all of the above. Other examples are ReplenAde™ Instant energy drink by Nutraceutical Resources, Inc. Norwalk Conn.; Oxy-Nectar® and Source of Life® energy shake and Energy all by Natures Plus®, Amityville N.Y.; Super-Green Pro-96™ by Natures Life. Garden Grove Calif.;

36. It is a further conceived that this invention includes encapsulations and/or micro-encapsulations that may be uniformly released and/or timed released. They may be in the form of liposomes, and/or any other form that fits under the category of encapsulations, and/or micro encapsulations.

a. It is conceived that whether uniformly released or not, controlled release, they may be nothing more than bursts of color and/or flavoring. First, the drink can, have red release, then yellow, and resulting in a red-yellow and/or orange mix. This can be fun and/or educational. Following suit, the same can occur separately and/or in combination as related to flavor.

b. Most often timed release, or sometimes referred to as controlled release, provides none of the aforementioned, and/or any and/or all of the just aforementioned, whereby they additionally may provide the ability to suspend the release of active ingredients until they reach the designated position along the gastro-intestinal tract. This is most valuable in the delivery of pharmaceuticals, nutraceuticals, OTC Drugs, enzymes, pre-biotic and/or pro-biotic formulations and/or the like.

c. Further, the encapsulations may be used to preserve and/or better deliver the active ingredients. These encapsulations may become active when the packet is exposed to the liquid.

d. The encapsulations may be imbedded in the filtering material, and/or dissolving material, and/or partially dissolving enveloping material, and/or contained within the mixture inside of the porous packet, in one or more compartments, and/or mixed with other ingredients, and/or separately contained.

e. Upon contact with the water, and/or liquid, the encapsulations may be released into the liquid from the envelope layer and/or travel through the pores into the liquid in whole.

f. It is further contemplated that after the encapsulations contact the liquid, some and/or all of the encapsulations may open and some and/or all of the ingredients contained within may disperse in the liquid. Further, some may not release, regardless of the temperature of the liquid; thus traveling through into the drinkers mouth, intact, and be release there, activated by saliva as an example, and/or travel into the stomach for release. Further, they may and/or may not travel farther down the digestive tract to the gut for release all at one time, and/or over a predestinated period. It is therefore to be claimed that any and/or all of the just aforesaid may be included.

g. In addition, flavoring, coloring, aromatics, pharmaceutical and/or nutritionally active components can advantageously be encapsulated and/or microencapsulated to ensure stability.

h. The microcapsules can be formulated to release their contents when they are exposed to the liquid by either fracturing and/or dissolving.

i. Alternatively, the microcapsules can be formulated within the micro-beads, or other components to be released intact upon the addition of liquid. In that case the microencapsulated ingredients readily pass through the packet's covering and are ingested with the liquid. The microcapsules then release their contents, even up to several hours post ingestion, at a predetermined designated point along the digestive tract. In this way, it is possible to precisely deliver a labile component.

j. Various and assorted encapsulated ingredients can be included in one encapsulation regardless of form. This can mean that there be several granules inside of one (1) encapsulation and/or micro-encapsulations that go inside of a larger encapsulation.

k. Encapsulation controls the stability, compatibility etc. of ingredients, as well as the timing of ingredient release etc. Encapsulations might separately, and/or additionally, provide an entertainment factor, especially if packaged in a clear envelope, no envelope at all, with or without a wrapper. Sometimes we might just have one large encapsulation, most probably but not limited to gelatin, and with compliance to the aforesaid resemble, as an example a rocket ship with or without indicia. Inside this dissolvable, and/or partially dissolvable rocket ship would be space related individual components each delivering value.

l. Further, if a double membrane is used then the encapsulations may be colored, varied, and/or consistent. The "beads" locked between all or part of the walls of the double membrane may or may not be fully transparent. The inside of the packet still contains all that is mentioned. These encapsulations may follow all of the claims here for encapsulations m. It is also conceived that the shells, post fracturing, from the encapsulations may remain inside the enveloping material for reasons such as they wouldn't taste good, have acceptable mouth feel, and/or any number of the clear and obvious. Further, it may add to the enjoyment, looks, if the shells remained inside the enveloping material, especially if the enveloping material was somewhat and/or very transparent.

37. Aroma, if concentrated, especially, may not always add a desirable taste to the liquid. In fact aroma(s) may even impart an undesirable taste. It is then conceived that the other components of the infusion packet and/or supporting member which does not come in contact with the liquid be impregnated with aroma. "Aromatherapy" is a word used often. The inventor however wants to be sure she is not limited to a specific definition, and if possible, in total and/or in part, consider that the aroma emanate from the immediate vicinity of the packet(s), wrapper, tag, liquid, packet, and/or container.

a. Aroma may present in one and/or more parts of the invention; thus be released simultaneously and/or progressively.

b. As an example of a progression would be when the container is opened, then additional aroma comes when the wrapper is opened, and then the packet and/or an attachment to the packet may bring forth additional aromatics.

c. The aroma(s) used may be all the same and/or different.

d. It may, and/or may not, be necessary for the user/consumer/and/or care giver to activate aroma. If the individual has some, and/or total control of the activation of the aroma, then if it was not desired at all what is claimed herein would accommodate.

38. It is conceived that the material protecting the ingredients, whether in one or more compartments be, made of a material that is not permeable.

39. The material may be transparent and/or made of any materials determined to be safe, especially when being exposed to food/beverage.

40. An object of the invention is to provide, adjust the composition of the ingredients, so that the ingredients are dissolvable not just outside the packet inside the liquid, but also be dissolvable within the packet as well. This would mean that, by the nature of physics, the ingredients would attract, draw, the liquid into the packet in a greater than normal proportion.

a. By nature, if the packet just sat in the liquid some of the mixture would leak out. If you created agitation within the liquid more would come out and at a faster rate, and if you lifted the packet out of the water the liquid would spill out faster through the perforations/pores that are sized, shaped, and arranged accordingly.

b. These holes may be part of the design to excite children. An example would be if the perforations were shaped like the eyes of an alien (See FIGS. 2B, C, and D).

41. Entirely new packaging methods may be designed that are both ingredient and intent specific.

42. Each infusion packet contains one or more active ingredients not normally packaged together or hitherto activated by this method.

43. All ingredients may be delivered dry or in any form that will allow the transfer from inside the packet to the liquid to occur as dictated by the specifics of activity, and/or desired effects, immediately or at a predetermined, or random determined length of time.

44. The same holds true for the delivery of the ingredients throughout the G.I. Tract.

45. The infusion packets may be packaged within a separate wrapper of any material appropriate to the contents and/or appropriate to all intentions as related to all parts of this invention.

46. Just as the packet itself may present various elements the wrapper for the packet may also contain in consort, and/or individually, promotional material(s), prizes, etc.

a. U.S. Pat. No. 4,841,712 to Roou (Package Service Company, Inc. Kansas City, Mo.) titled Method of producing sealed protective pouches with premium object enclosed within;
b. U.S. Pat. No. 6,251,450 to Giacoman titled Food Packaging enclosing removable prize; U.S. Pat. No. 5,127,743 to Miller titled Method of manufacturing a package with a built in promotional piece;
c. U.S. Pat. No. 5,119,940 to Grindrod titled Package having collar enclosure;
d. U.S. Pat. No. 5,035,515 to Crossman and Lloyd titled Packaging having detachable coupon compartment;
e. U.S. Pat. No. 5,009,518 to Faltynek (Bagcraft Corporation of America Chicago Ill.) titled Window-style bag with integral coupon.

47. All the just aforesaid may also serve independently and/or in combination with the "fob" and/or the connecting piece from the packet to the fob if one, by design, should exist.

Please note that this connecting piece may be made of any material and/or shape as long as it provides the necessary function. If, for example, it is a spring coil then children may find the bouncing tethering effect fun. If it is a straw, it may be used for drinking.

48. Further, it may bring forth any and/or all of the characteristics that are on the packet and/or the tab (fob) at the end of the connecting member. The packaging of the infusion packets in a separate wrapper or stacked in boxes of a predetermined amount is in keeping with the invention, and obvious to those skilled in the art of manufacturing technology and tea packaging. In business opportunities, models, and methods this next concept will receive expanded attention. However, just touched upon here is to implant the thought of the intent of the inventor. Whenever and wherever possible the inventor is most interested in setting up job shops for the disabled/health challenged. By all invented here, this invention could provide an opportunity for them to engage in a repetitive skill, serve to reinforce self-esteem, all while "packaging healthy".

49. Much has been mentioned in the way of children, the inventor is now compelled to claim special accommodation to the elderly, seniors.

Additionally, many of the new beverages that the elderly/seniors are made aware of not only contain sugar, but these beverages may contain ingredients, which may not mix with the many different medications taken by most seniors today.

Moreover, many of these so called "new age" beverages boasting there positive effects are very expensive, and our older population does not have discretionary income.
a. As a result, the seniors are left with what the children have, plus the disadvantages which go with liquor, coffee, and even tea; a huge amount of caffeine.
b. Thus, it is the object of the invention to provide a unique delivery system for all humans and animals, but also to look towards the senior's marketplace, and treating seniors with special consideration by the design of the beverage, the artwork, etc.
c. Many seniors are afraid of hot liquids because of infirm hands and failing eyesight, yet they delight in traditional custom and would so enjoy a vehicle they recognize, like person, however when they reach their teenage years and desirous of their independence, the complexion changes.
b. Further, so many are so insecure and they seem to select and follow what the advertisers promote and/or what is considered the best, new thing. All we have to do is look to the clothing industry as example.
c. Then too the big beverage companies not only sponsor the programs that the kids watch on television, they sign and/or show up at their events, games, and the like. Additionally they hire teenage idols to represent them. Pepsi® has just hired the popular singer Britney Spears, and formerly Michael Jackson, to sell the image ergo their product to this especially vulnerable age group.
d. The inventor here draws attention to the fact that she is not against big business targeting teenagers so profoundly, just big business not selling healthier.
e. To encourage teenagers, one must design product according to the guidelines of this invention that will, "knock their socks off" with creativity, a show in a bottle, all the previously mentioned "Bells and Whistles" etc.
f. Further, to encourage by contests, which require and/or don't require participation skills, and/or let the teenagers have under appropriate guidance, the ability to participate in the marketing, selling, and ultimately in the profits made under appropriate governorship and/or sponsorship. The inventor herself is a lifetime member of Sigma Phi Epsilon, a college fraternity of marketing students on about 150 college campuses. Certainly, that is a place to start. Not only can all aspects as related to a business model and method on campus be looked at, but also the thought of bringing health, and health-related information, to this age group is important to the inventor.

BRIEF DESCRIPTION OF THE DRAWINGS

FIGS. 1A, 1B and 1C are exemplary illustrations of infusion packets designed to be used in a narrow necked bottle. FIG. 1A shows an illustrative and exemplary perspective view of an infusion packet designed to be used in a narrow neck bottle with a "sports top". FIG. 1B shows an illustrative and exemplary perspective view of an infusion packet designed to be user in a narrow neck bottle with a regular bottle top. FIG. 1C shows an infusion packet in a swelled confirmation following contact with liquid—this configuration is unable to pass accidentally into the user's mouth or plug the sports top.

FIG. 2A is taken from FIG. 1A and FIG. 2B is taken from FIG. 1C. FIG. 2C shows a detail of color streaming from a figure shaped infusion packet. FIG. 2D shows the infusion packet after all the color has left the packet to color the surrounding liquid.

FIG. 3 shows a perspective view of a support member shaped as a toy figure. This support member is attachable to a drinking straw and also alternatively holds or contains the infusion packet.

FIG. 11 illustrates a support member that is used to connect diverse infusion packets. FIG. 11A shows a surface view, and FIG. 11B shows a sectional view to expose the diverse contents of the infusion packets.

DETAILED DESCRIPTION OF THE INVENTION

Figure 1C:
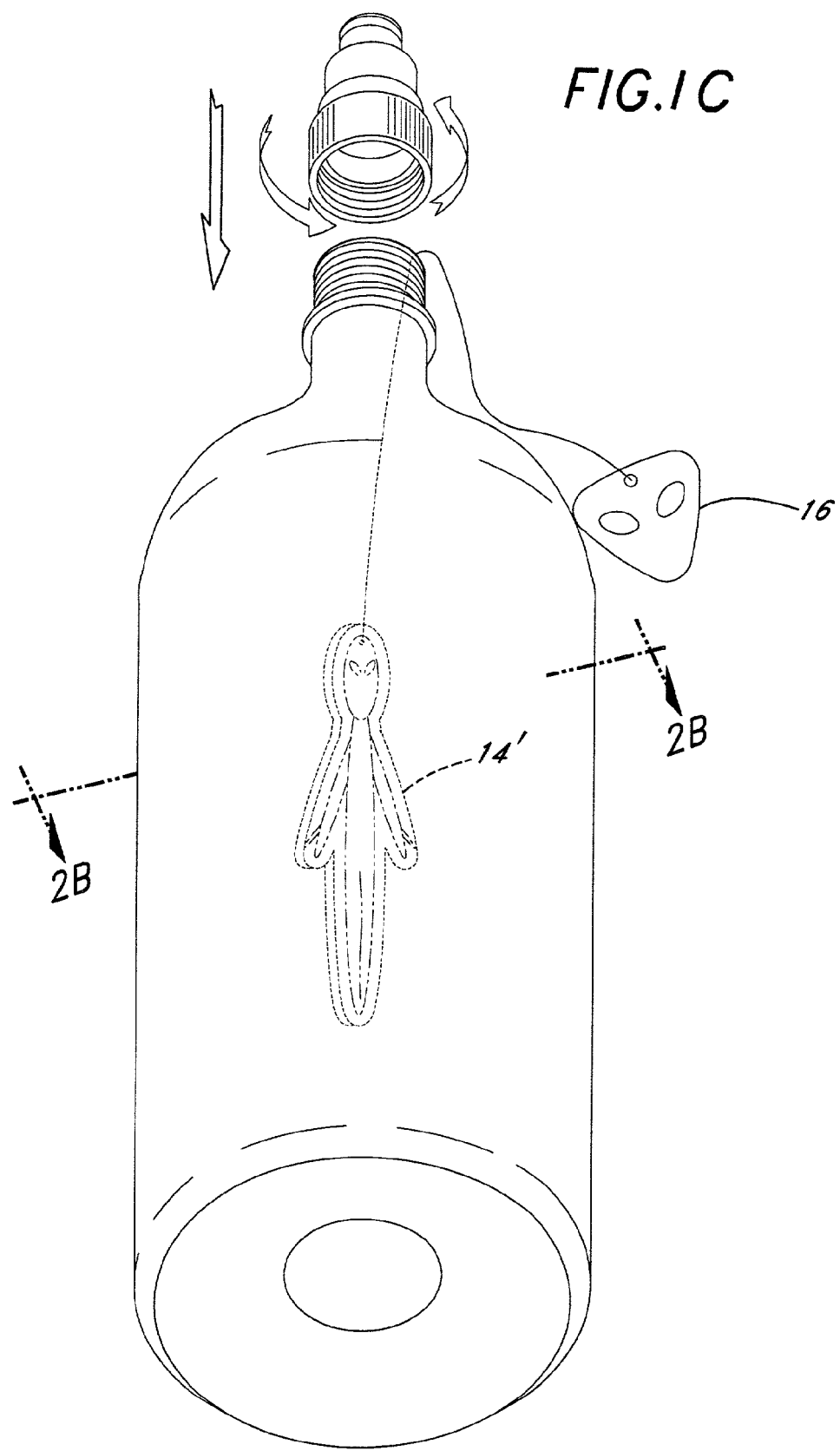

For interpretation and clarity the inventor has chosen to use the word "infusion delivery system", the most common would be the "infusion packet" to included other common terminology such as tea bags and/or sachets. The inventor feels that the term, "tea bag" may prejudice the reader towards a belief that only an aliquot of herbal materials are enclosed within and, perhaps more specifically, used for drinking. While the term "sachet" also refers to a small bag, it is most commonly used when referring to a small bag containing a fragrance, and whereby the sachet device is used to dispense fragrance.

For clarity the inventor will refer to liquids mainly beverages as to include anything, regardless of a food qualification category, that will be brewed and/or dissolvable in total or in part and pass through perforations/pores/holes, a permeable membrane or mesh, regardless of the materials used into liquid.

Encompassed herein would be a category commonly known as soups and broths, stock, teas (preferably non-caffeinated), coffee (preferably non-caffeinated).

It is however conceivable that an infusion system of the just described be used to enhance the water and/or liquid used for making Jell-O®, rice, and/or the like, either before the liquid is heated or after heating but before the solids are added so as to give an even disbursement.

For clarity again, the inventor has chosen the terminology "support member" to mean any device, regardless of the material, that is used in conjunction with an individual infusion system/packet and/or group of packets to support the packet or packets. By support member, again for clarity, the inventor means, any and all additions to the delivery of the consumable regardless of it being purely artistic and/or functional in whole and/or in part. For example, as a tool to handle the packets, a clever means to join them together, a straw for drinking, promotional materials, a game piece, or an after the experience reward/toy to collect and/or to play with.

The present invention is targeted at, humans of all ages, and even to animals because many pharmaceuticals, nutraceuticals, and/or dietary active additives only demonstrate activity, and/or, show better stability when administered in a freshly dissolved state.

The present invention is geared towards preserving the integrity and the activity, of the ingredient(s); both in terms of how the individual packets are packaged and, additionally, how the ingredients within the packets are stabilized until the packets are used.

The primary interest of the inventor is to provide a safe, easy, efficient product which is convenient and fun to use, while at the same time providing opportunities for beverage development with more natural and healthful ingredients and reduced sugar loads, to target specific needs and/or ages of consumers.

Ensuring Hydration is a Very Important Part of the Inventive Goal.

A portion of the infusion packet invention is directed primarily to an adult population, who has mainly used hot liquids (mainly water) for activation, extraction, or dissolution of the active components. However, it is noted that this adult population are now consuming a tremendous amount of ready to drink teas, coffees, sodas, new age beverages, and energy drinks sold today. Some of these claim one or more health benefits and are labeled as such, but with those purported benefits comes a serious amount of sugar and also often caffeine, a stimulant which is also dehydrating, and further complications if certain herbals/botanicals interact with prescription medications.

Business Models and Methods

The invention brings forth the ability to conduct test market research and focus studies, while providing hydration and "good for you" components for sale and/or for free/sampling.

A new dispensing venue is conceived whereby new concepts of vending, and therefore new types of vending machine(s), can offer dual products. As an example, a bottle of water and a selection of product for the same price, or at an additional cost, may present.

While a new vending machine, and/or the retrofitting of an existing machine, can be developed, it would take considerable time and cost to bring it to the marketplace, ergo the consumer. Further, it might not always be desired for reasons to be discussed later.

Therefore, at this time it would be far better to present a separate vending/dispensing machine, dedicated by design and/or construction, to deliver the infusion packets, and/or infusion packet systems, with and/or without a support member.

It is envisioned that this machine be positioned in close proximity to, and/or along side, and/or attached to, an already existing vending machine and, most probably one that delivers bottles, including but not limited to water. Further, the new machine may stand alone, and/or be attached to any existing object for safety, ease of use, etc.

It is also conceived that there be a way whereby a possible cost of the dispensed packet be absorbed into the cost of the bottled drink, other than reducing the cost of the bottled drink, and/or by design, whereby permitting the buyer to acquire a packet. Upon paying the cost for the bottled drink, most probably water; one would receive also a pre-selected, by the company, packet or be allowed to make a personal selection. In this instance, the two products would be dispensed together and/or in immediate succession.

Another option covered by this invention, is when an individual for an additional price, may decide to buy a packet. This purchase provides feedback in and of itself as related to consumer preference.

Another way is where, when the liquid is purchased the vending machines literally signal each other and/or send a one way signal that automatically allows one packet selection per purchase of a portion of liquid be made available, without adding any additional currencies.

It is also possible for an existing primary vending machine of liquid to dispense a token, and/or token like object. Further, like in a gambling machine display a credit. This credit then permits a packet to be dispensed regardless from where.

That is, the primary machine is so designed and/or re-engineered to dispense, simultaneously and/or in a rapid succession, this "token" which will be used to activate the infusion packet system's vending machine. It then delivers, according to presentation, (menu written/pictured/displayed), a packet with and/or without a support member.

It is probably that in reengineered machines the token will be dispensed, using the change delivery system already present.

It will be a business decision, and/or a technology decision, whereby the "ideal" might be to have a removable and/or "scannable" part of the container of the liquid be used to activate the infusion packet portion of the system, and/or a separate infusion packet vending machine.

That is, besides a token, a portion of the normally dispensed bottle would act as a token (through a bar code, etc,), which could be used to obtain an infusion packet from another machine. This would allow a system wherein the infusion packet machine would not have to directly accept currency, with the attendant complexities and vulnerability to burglary.

It might be advisable that the secondary machine perhaps only be active for a predetermined period, so as to prevent consumers from taking home the "token" for future use, and/or to prevent the scanning of a bottle more than once, and/or scanning discarded empty bottles. With a scannable operation, a consideration should be whereby the device must be constructed for a one-time use only.

The aforesaid will also give immediate feedback to a company who, let's say, provides bottled water. They will quickly obtain market data showing decisions as related to those that decided to take advantage of this situation. In addition, with timing technologies, how long it took a consumer to decide, along with their preference if offered one.

Just as movies are rated, so can drink packets be differentiated, especially when it comes to segmenting the market, and especially considering children. Often graphics, and/or name used will do this. Parents and/or caregivers must also take responsibility.

In the case of herbal and related packages it would be prudent to list on the vending machine, and/or on the infusion packets, wrapper, and/or the like, to make visible any known contraindications, warnings, drug interactions, and/or the like.

Perhaps not so obvious is that if the company who owns both machines, designs the system so that the packet system vending could also accept the currency of the country.

These machines can be placed next to and/or near the machines (and therefore products) of a rival company. This obviates many marketing, selling, testing, advantages.

In addition to the business model set forth as related to convenience machines, vending machines, and/or the like as a venue(s) for selling and/or giving for free infusion packets while simultaneously providing a forum for the ability to elicit a broad test marketing opportunity as the inventor described.

Further, it is to be the objective that while exploring, and/or conducting and/or the like, those participants will be receiving product with enriched value, active and/or non-active ingredients along with hydration.

Further, not just by the ingredients themselves the test marketing will serve a function but also will be affording the opportunity to evaluate the validity of specific ingredients assuming they are used according to directions, and for a specific period, regardless of the venue henceforth mentioned. As an example, one might note soluble fiber. If looking to test market, as in the just mentioned ingredient category, regardless of specifics, then various combinations of fibers might be offered, with various flavors and/or other constituents.

While these models and methods, which were originally conceived for, and basically designed to go with a bottled water product for safety they can be designed around any municipality water dispensing machine and/or the like.

Further, by one and/or more of these business models many other testing options present. One thing that must occur is the goal of the testing. By this the inventor means for example: is it to test color and/or product preference based on, but not limited to; presentation, preference, function, ease of use, shape/design/decorative elements, even the preferential support member(s) etc.

Additionally, to know the specific and/or general intent such as, whether it is to be always sold in packet form, under the guidelines set forth by this invention, and/or on the other extreme, is the testing purpose just for the sake of taste/color and/or whatever would be considered valuable in the way of testing for a RTD beverage which will eventually be a mass marketed product.

As an example:

It is possible to present the same product in several different forms, flavors, textures, etc.

The wrapper can change.

If licensing is a consideration, then the popularity of a character and/or the like can be tested.

The just aforesaid may change, with geographics, and/or demographics, as well as many other factors. Certainly, when one thinks international this becomes more of a consideration.

Business Opportunity, Model, and Method as Related to Eating Venue

What has marveled and astonished the inventor is that when one goes out to eat, room temperature or more often ice water is given for free; but you have to pay for a cup of warm-hot water even if it is, most probably, the same water. WHY?

It surely is not the glass as often times hot water can be served in a glass. It is because the hot water is not ordered as hot water, it is ordered as the fluid necessary for tea.

A while back, there were only one or a few kinds of tea offered (covered under the background of the invention). Then in the last decade, herbal teas and botanicals in tea bags became very popular. Additionally, teas with a purpose such as mentioned in relation to the company, Traditional Medicinals® and others such as Celestial Seasonings® and Tao Tea® brought forth not just new blends, but new blends with a cause/function.

While tea is not common for children, the inventor notes Fennel Tea for Children, a product by Sidroga Inc., West Palm Beach, Fla. The directions/instructions are as follows: 1 tea bag per serving or per cup. Pour on boiling water. Allow steeping for 2-5 minutes. Squeeze the bag gently and remove it. Drink 1-2 servings of freshly prepared tea spread throughout the day etc. The directions also say you can add sugar to taste, but with a warning that if you're desirous of preventing dental decay the recommendation is not to use sugar at all.

In restaurants, and more so in the fine dining establishments, an assortment of teas are brought to the table from which the customer may make a selection. These teas are not all listed on the menu either.

It is in light of the just described that the inventor presents, as an object of this invention, the invented presentation of packet(s). Just as so described, with any and/or all details stated herein, with and/or without a support member(s) be made present in an eating venue, thus offering the customer/consumer the opportunity of making a selection to go into liquid, (mainly water and hopefully safe water which is bottled with and/or without gas).

If as example, a box of 8 assorted packets were presented to a customer it would be easy, in a short period of time, to see which of the 8 was the most popular by reorder and/or a constant consistent new order.

Further, these packets may be given only with the purchase of a specific bottled water, (gas or no gas) by the company producing, and/or marketing/distributing the water.

Many consumers do not want to pay for bottled water in eating venues. Some don't believe in it, while others look at the price as compared to the specials in the supermarkets, and they feel taken. When a bottled tea and or a RTD new age drink costs $1.50-$2.50 in a market and/or convenience store then it is price comparable to a bottle and a packet in the eating venue. From fine dining establishments, to eating venues such as those with fast foods: Burger King®, Mac Donalds®, Taco Bell®, Wendy®, are all considered.

This method will promote the sale of bottle water in these venues, while at the same time might also give the company who provides them, along with their water, a competitive edge to get into restaurants first, and hold a profitable noticeable position. This give them exclusive brand identity in the bottled water market etc.

As to the last mentioned, consider how long a bottle may sit, with its label on, in the consumer's direct vision during a long period of time. The inventor envisions certainly far longer than a blurb on. Super-bowl Sunday. Further, while at the same time, give feed back as to what new beverage to consider for mass market. By the nature of the just described this will obviate that colors can be tested also, and/or the like.

This is of special importance to the inventor in relation to kids' drinks, which now may be custom built off a bottled water, safe water, purchase in a restaurant. Very rarely, do caregivers order bottled water for a youngster. Certainly, this is a giant step to reduce the volume of soft drinks and sugar consumed by this population. If the kids' version drinks, which can come in a separate box with all the "bells and whistles", referred to in the context of this application, then we just might make that important difference so sought by this inventor. As an example, Mac Donalds® offers a Happy Meal, why not a Happy Meal with a Happy Drink and/or a Happy drink alone?

Now new superheroes can be launched via the beverage industry, and not by violence on television, and/or in a video game, and/or in feature films . . . but the kind of superhero that stands for the positive, and promotes good healthy eating and drinking. (A Far Champion, but one that can surely come to life.)

Home and Office Delivery: New Venue Business Opportunity, Model and Method

Home Delivery

Not often does the U.S. Government have access to your home, nor usually, does the milkman, but the water deliver boy does. Home and office delivery of bottled water is a big business in the US, and gaining much popularity abroad.

In the beginning, over 50 years ago, all that was delivered was the 5-gallon (20 L) bottles. Through the more recent years smaller sizes became available mainly for those who lacked room, space, didn't want to store large bottles, and/or who live alone and cannot lift that heavy bottle, invert it, and place it properly on the canister with ease.

In addition with the plethora of new home filtering units for water, along with the all the new beverages, many have given up water as a separate entity.

Bottled water sales have increased dramatically whereby much of this increase is due to the sale of smaller, single-serving, oriented and proportioned sizes, it is noted that many even come with sports tops for ease of drinking. Just recently are the home delivery water companies taking note of this growing fraction of the business. However it is fiercely competitive and, other than different types of coolers canisters and/or the like, no new product relating to the enhancement of home delivered water is available.

Yet this is a perfect opportunity, through this invention to duplicate what the inventor has presented for eating venues. Naturally this venue might obviate minor adjustments and/or changes, but the basic infrastructure is there.

Now the home delivery companies can offer an opportunity for in home beverage testing as well as development unilaterally, and/or in consort, with another company. After all, the goal is to sell more water. More water makes you more hydrated ergo healthier.

Kids like to make mix and concoct things, and with a home beverage development kit they can do as such. Therefore, a new beverage developer might just be in the making. Further, sponsored contests, by companies, schools, organizations, and/or regions, just as with new healthy attitudes towards cooking, might bring forth new and healthy hydrating drinks.

At least all of this is thus designed so that the public can positively influence industry and hopefully, participate with those that have the power, money, and distribution to make good things happen for people of all ages.

Office Delivery

With water and/or companies supplying water purifying machines, popular at, home and office, this gives not just the water supplying companies the above, but those companies who are desirous of getting their machines in the home, perhaps also more of a bent towards providing an office.

Often in an office environment due to air conditioning, etc. the environment may be dehydrating. Further workers are not always able and/or allowed to get up to mix a drink. Many bring hot drinks to their workstation but they may be dehydrating. Many bring water, but some don't like water. They want something more. In large offices soda machines are available (vending mostly) but filled with the not especially good for you type of drinks. Sometime in large office buildings there are little shack shops with limited space ergo the RTD beverages sold are limited.

Now be it in the office and/or the little snack shop in the building and/or any venue in the office building one can supplement, mainly bottled water, with a myriad of choices emanating from a small container easily stored and held. If a little support member is also present, it could be a small token gift brought home to a little child and/or the like.

Street Carts and the Like

Another venue of potential introduction and sale of product, along with test marketing, are the street carts. Especially popular in large cities, and especially in downtown areas, we find street carts offering cold drinks.

Again, what is sold in these little venues are the products of the big companies, mostly sodas, and not especially healthy . . . but when you are the only game in town what choice does the consumer have?

The alternative is that some companies put on the streets their own carts which is an expensive proposition, but some can afford to, especially if they are under the umbrella of a large conglomerate with the funds to do so. An example would be, the So Be New Age sugar loaded drinks which are owned by Pepsi®. This inventor feels that those individuals hurrying about, who are thirsty, have no choice but to take what is offered.

Sports Arenas, Movie Theaters, Stadiums, Concert, and the Like Venues

Anywhere large groups of people attend a function lasting for multiple hours they often want to drink, and are at the mercy of what is offered by the venue. These venues do not like you to bring your own beverage even water, to their establishment, and often will have you throw it away before entering, or if caught.

In venues like this where lines need to move fast, also in fast food venues, if many choices are offered it can slow up the line. It is therefore conceived that if it is impractical for a venue to offer for free as like with salt and mustard, that a machine be made available so that when you purchased your liquid, mostly bottled water, you could go to the machine with a token, and/or the like, which would activate one selection.

"Doing Good While Doing Right" is the Operative Principle for the Use of this Invention to Help Those with Developmental Difficulties, and/or Health Challenges of any Sort, and/or of Any Specific.

There is no doubt that in society today there is even a greater emphasis on not just improving health through good nutrition and the like, but the goal of providing business, money making, opportunities along with esteem builders for those who have specific challenges.

While big companies want to hire the handicapped/disabled, they often do not have jobs for them. If they do have a position it may not be full time, and/or they might be the first to be laid off in times of budget cutting. So, the population that needs it the most may suffer first.

Hardly fair, but real the inventor tried through her promotion company, Zen & Wow!, to offer opportunities for this population in accord with an affiliation to an organization, and/or a skilled intelligent person, by which to sell unique, promotions to big companies. For many reasons this did not work. She then realized that if this was going to work she had to find something that this universe of people could sell, and that would have to be something that she controlled.

A further goal was to have something that perhaps larger companies would sponsor because they wanted to help by participating, and/or they genuinely needed it, and/or wanted it now and/or eventually. Additionally, it could become big business for them.

As timing would have it, the last final touches to this invention were started the day, Sep. 11, 2001, of the horrific NYC and Washington D.C. tragedies. Over the last ten days, this inventor has witnessed so much of this audacious atrocity. It can never be undermined, but in the wake she is also seeing how America is coming together, and truly believes that, as a nation, we will be more considerate towards those less fortunate.

Further if possible, because not everyone with a health challenge is able to sell, perhaps other skills could be employed and that might be accomplished in the fabrication, design, etc.

Also of major significance would be the ability to provide job shops, and/or work for job shops, by assembling in total and/or in part this invention. As an example while food/beverage production must be under the control of specific facilities, many of the support members are not made of a food product, and/or do not come in contact with a food and/or beverage product.

Therefore, and depending on the nature of the support member(s) etc., much in the way of little toys, and toy/like parts can provide jobs for so many.

The inventor calls attention to a little toy made by Doodletop®, for which a little spinning top had, at the end a small felt tipped marker which when spun made marks on the surface of, hopefully paper, by children. Not only was this a delightful little gift, but it was also picked up as a promotion by Mac Donalds®. Doodletop provided opportunities for a small job shop assembly line for the handicapped. Unfortunately, they were bought out and production left America. The disabled were laid off and now 4 years later, many have still not secured another job.

Certainly a little top, a universally recognized shape and toy worldwide, can be fashioned to hold a single serving packet with an after use function, and/or if presented in larger fashion, multiple servings of infusion packets and/or a large packet. When the product contained within was used up, the remaining spinning top, would still be in and of itself an operative toy.

Bottled Water and Water Bottles

With many consumers today drinking bottled water, and with the inventor being prejudiced towards hydration, and with the fact that hot water is not necessary to reconstitute many formulations, it is therefore ideal to have a shaped infusion packet that will readily slip into a bottle. While it is possible to tear open a packet attempting to pout the contents into a bottle, more often than not, much of the contents spill on the rim, the side of the bottle, and/or fall on the countertop. While it is possible to "stuff" an existing infusion packet, "tea bag", into a bottle, one risks the chance of tearing etc., thus rendering it unusable.

Further, all of the infusion packets that exist today need a very warm, even better a boiling hot, solution to activate. The polyethylene terephthalate (PET) bottles cannot be heated, as the material can't take water over 160° F. (70° C.) without undesirable shape changes, etc.

While it is possible to put one of these infusion packets into a bottle and let it sit for a length of time, it has its drawbacks, mainly the length of time to make the resulting beverage.

However, the process has been used successfully, whereby this process has been called making "sun tea", from a time when individuals would put tea bags in water and then let them brew in the sun. The inventor discovered that consumers do not want to bother setting up this process way in advance, over overnight, much less time in the sun. U.S. Pat. No. 6,235,323 to Cams, (Nestec S. A. Vevey C H), titled tea bag for iced tea makes an effort in a traditional fashion The invention set forth here easily accommodates the opening of a conventional PET bottle. The volume of liquid to be delivered is determined by the size of the bottle used. Most common today are bottles that hold 8.0 oz. (0.24 L) 16.9 oz. (0.5 L), 20 oz. (0.6 L), 23.5 oz. (0.7 L), and 50.7 oz. (1.5 L), of liquid/water. It is of note that most all have a standard opening that will also accommodate the very popular sports cap.

To overcome the aforementioned the inventor has patterned a shape that will follow the concept of a tea bag, fashioning an infusion packet whereby the entire unit may be dropped in, and if:

27. Attached to a stick like and/or a straw (which can serve for drinking); and/or,
28. In the process be held down either long enough as not to float (possibly by magnetic forces) and/or,
29. Long enough as to deposit all the enveloping contents into the liquid and/or,
30. If by attached to a firm connecting member such as a tube, straw, stick, and/or the like, with or without a magnetic capability on the packet itself and the mate on the outside of the bottle to hold it in place.
31. If a straw is used regardless of shape, then it can also serve the purpose of drinking, somewhat different from the straw with perforations described in detail earlier.

Depending on the volume of liquid, in relation to the nature of the contents, the weight of the product will be in the range of 0.01 grams to several hundred grams.

The larger amount would be in effect, if the user wished to make a strong concentrate to be diluted later. As an example of a circumstance whereby this would serve a purpose is, if one does not wish to take many individual bottles to a venue where bottled water is easily purchased. In that case, it is conceivable that the group purchases the small size bottles. Then they either take a drink of water and/or spill out some of the water to accommodate the inventive concentrate made from the infusion packet. The usual breakdown for a concentrate is an aliquot of the concentrate to usually 8 oz. (240 ml) of liquid.

The infusion packet may or may not have a connecting member, usually a string, and/or as described above a rigid member that may, or may not, have a tag or tag-like arrangement at the end.

While this invention is specifically designed to go into PET bottles of water, it may further go into glass bottles as well. Further it may go into glass, plastic (be it PET or any other plastic combination) regardless of the shape, and/or size of the container of water and/or liquid, and be used to add nutritive decorative flavorful, and/or aromatic stimulants, should they be so desired.

Color is also important especially when a liquid such as water is virtually colorless. U.S. Pat. No. 6,224,922 to Fonte titled "Drink Colorize" whereby the specialty beverage container has multiple colorant reservoirs built into the cap to be released singularly or in combination to create a beverage of a specific color, hue, and intensity.

The basic structure of a bottle infusion packet 14 is shown in FIG. 1A in place in a PET water bottle with a "sports top" 18. (FIG. 1B shows a regular top 22). The packet 14 is sized and shaped to fit through the neck of the bottle. A tether 13 (usually a thread or string but a chain, monofilament or other connector could be used) connects a tag 16 with the packet 14. Here the tag 16 is a decorative (possibly collectable) "alien face". FIG. 1A shows the packet 14 slipping through the neck of a bottle. The tag may also be adhesive backed, as is tag 12 to ensure fixation on the bottle side.

Again it is noted by the inventor that there is a concern as to when the drinker drinks the liquid, if he has not removed the packet from the bottle, whereby swallowing can potentate a dangerous situation.

Figure 2A:
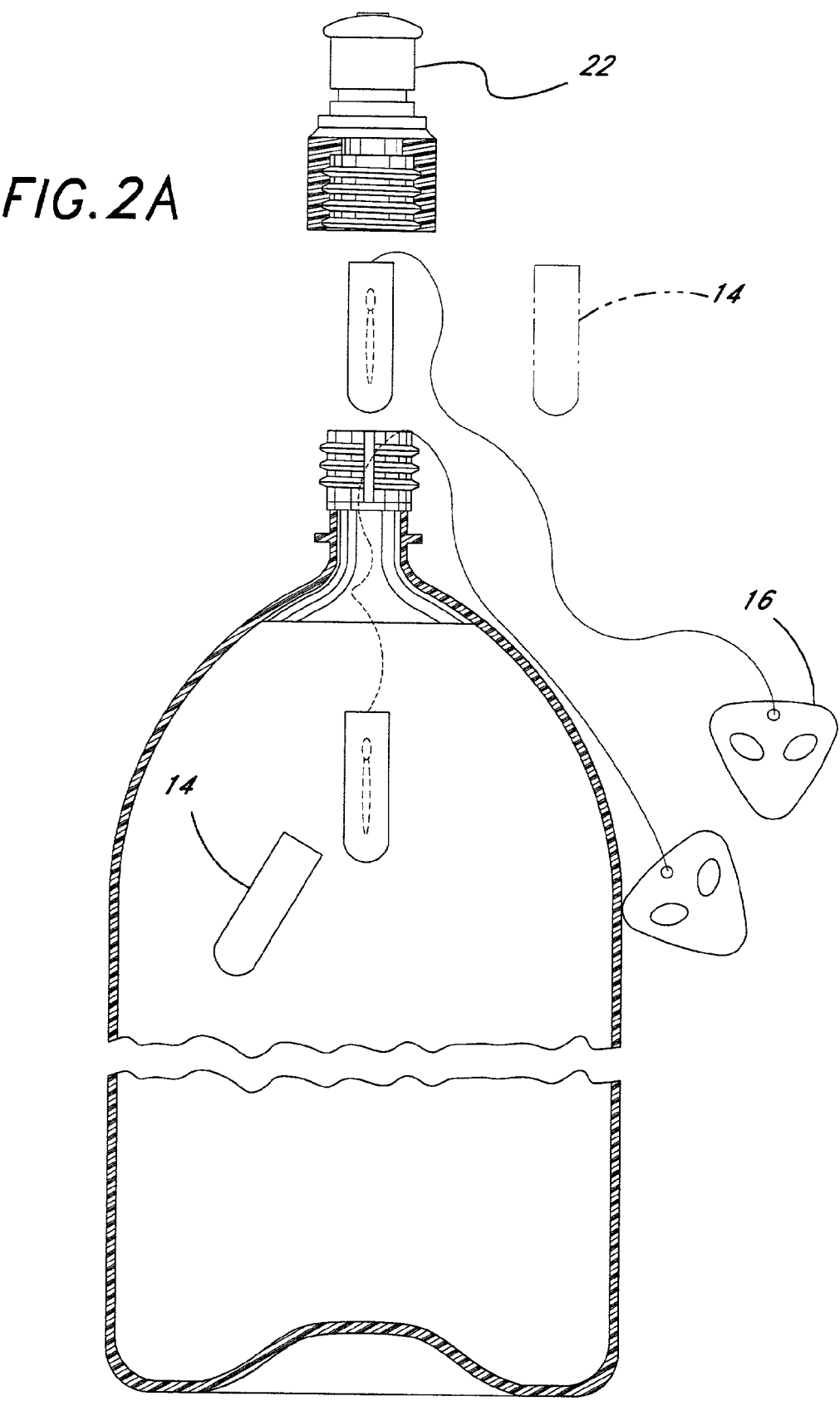
FIGS. 2A, 2B, 2C and 2D show a sectional view of the device of FIG. 1.
Figure 2B:
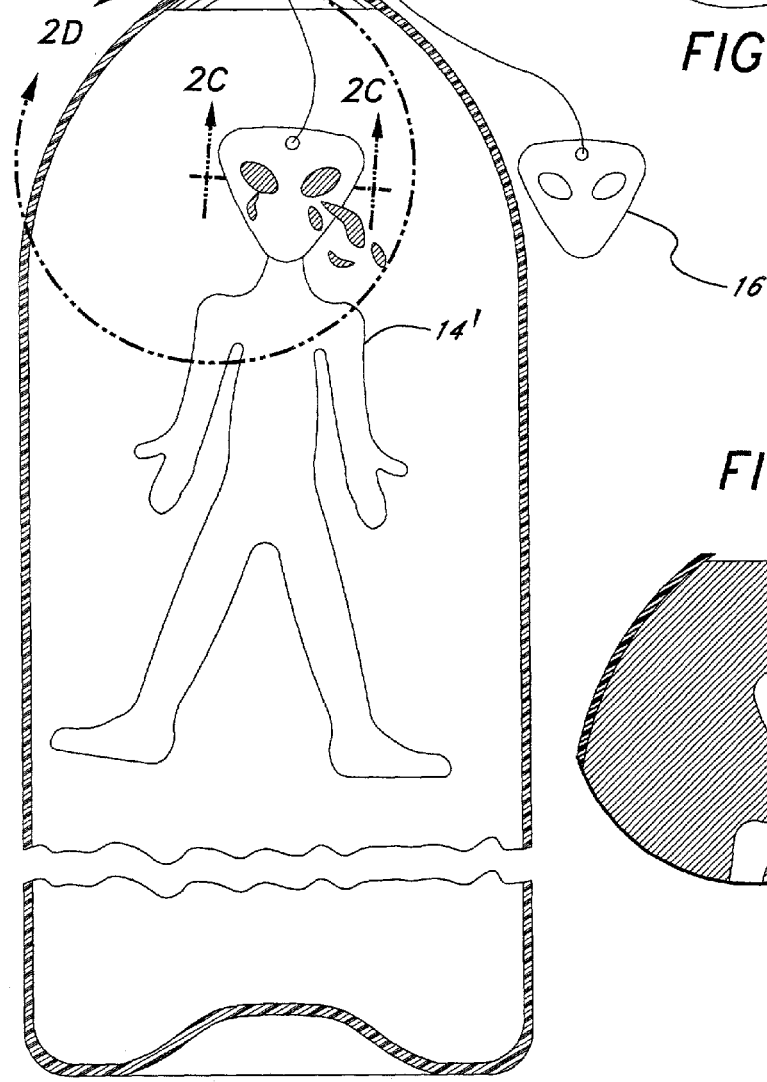
Figure 2C:
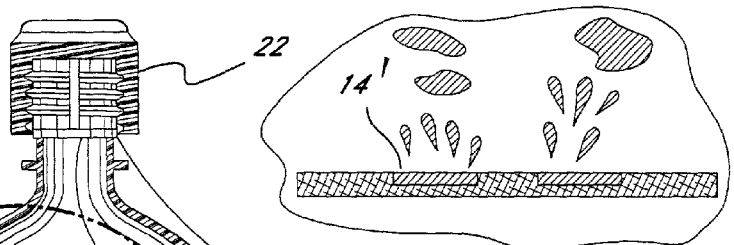
Figure 2D:
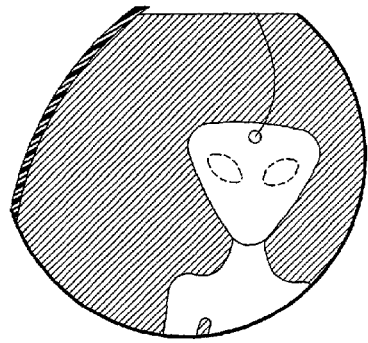

32. An edible, dissolvable film containing the active ingredients is one way to address this situation so that the packet would dissolve completely leaving no residue.
   a. It is, understood, by those in the art, that if the film containing the active ingredients is dissolvable then the ingredients inside must be as well
33. Using a sports cap 18 mm to limit the opening of liquid going into the mouth is another potential solution.
   a. However, the packet may lodge against the cap and prevent the flow of liquid out of the bottle.
   b. Further, sometimes a cap may be switched and therefore the safety thought attached to the sports cap may no longer exist.
34. The inventor is most concerned with all aspects of safety. It is then therefore the object to invent a product with a system with an enhanced safety feature.
35. This would include as an example: a compressed sponge and/or a sponge-like material, which, may and/or may not be contained within the inside of the infusion packet, which may and/or may not be attached to the packet. It would be designed using the elements of gravity in addition, as needed; to provide weight, magnetization, and/or the like, and if needed in consort with any property of the bottle and/or an additional support member.
   a. The engineering is dedicated towards safety as well as proper usage such as to avoid floating to the opening whereby blocking the opening.
   b. Therefore, when it, and/or the packet, becomes wetted it will increase in size, thus rendering it expandable, and/or "openable", in part, and/or in whole by any fashion and/or technology.
   c. This has been also described earlier under the concept of origami: when wet, be sponge like, absorbing liquid, subsequently rendering the item too big to go back through the neck opening of the bottle.
   d. It is further conceived that a sponge, and/or a sponge like material, be impregnated with active ingredients regardless of form whereby both are delivered into the bottle at the same time.
36. The form can include, but not be limited to encapsulation(s), granules, tablets, powders and the like.
37. The sponge, and/or sponge like material, would expand and release the active ingredients into the bottle.
38. This is illustrated in FIGS. 1C and 2B where the packet 14' has expanded to preclude, reverse passage through the bottleneck. Note that expansion has revealed a specific design to the packet 14 that now represents an "alien" in keeping with the alien face tag 16. FIGS. 2B-D show an additional aspect of the invention wherein the packet forming the alien head contains perforations through which color (alien tears) is emitted when the packet imbibes fluid. FIG. 2D shows all the color now in the surrounding solution.

As related to how to get these packets to the consumer using a business method, and simultaneously addressing the individual bottles here the inventor, to keep on track, includes the following as part of the invention.

That is, it is possible to use the infusion packet as related to a drinking bottle in the following manner.

39. The bottles can be made available with the addition of the infusion packet already inserted in the bottle, ready for activation, whereby the consumer can add water, and/or any other hydrating liquid to activate (e.g., release the contents of the packet into the solution).
   a. If there is to be a bottle with an effervescent packet then there must be an indicator line on the bottle to show how close to the top to fill (as effervescence will take up headspace.
40. If water supplied is with the packet, and the packet is to accommodate effervescence, then there must be the appropriate headspace provided by the manufacturer.
41. Regardless, knowing there is intent to put a packet in a bottle, then all bottles filed with this in mind should be filled so as to accommodate, while also allowing for the full appreciation and dilution of the product.
42. The alternative is to drink, and/or pour out a portion of liquid before adding the packet. If so, an indicator line is still most helpful. While it is possible to present this invention with the infusion packet inside the bottle ready to accept the liquid, it may not be practical and/or safe to do so, even with a tamper-proof system in effect.
43. Therefore, the following is a variation on the same invention. The infusion packet may be provided with the bottle, but not inside of it. Packaging technologies and blister pack technology is so advanced whereby this becomes economically practical. Additional advertising, coupons, promotions, or the like can also be added at the same time during the aforementioned packaging.
44. Additionally, as a consumer item the packets may be made and sold individually, or in sets, either as a mixed variety, and/or of the same content. This would allow the consumer to efficiently buy the drink mix of choice, purchase a bottle of water, or fill an existing bottle, cup, glass, mug, and/or the like from, as an example, a home delivered 5 gallon (20 L) jug.
  a. Suggested mixing instructions; including but not limited to a volume of liquid to be added, would be printed on the packet itself and/or accompanying literature.
  b. Along with these packets, there could be included advertising materials, coupons, samples of additional products by the company, promotional material, etc.
45. In a retail venue, it would be most appropriate to have these made available in close proximity to where bottled water, and/or beverages are sold.
  a. Another likely place, since the packets are small, would be in proximity to the cash register.

Alternatively, the design and/or color may dissolve off the packet in whole or in part into the liquid and go undetected in the liquid. This can be most fun for children as they may see their favorite character slip into their drink and literally disappear, and/or the just aforesaid may slip into the water and color the water/liquid.

Not unlike polished stones we see today in the stores, which have inspirational words like the word "believe" carved into them, and/or messages such as "an ounce of prevention is worth a pound of cure" on wooden plaques, these same words/messages may wash into the beverage.

Additionally in the reverse, when the infusion materials comes in contact with the liquid, graphics and/or secret messages can be revealed.

Another Look at Children

Of keen interest to the inventor is the development of products specifically geared towards the younger generation as well as products, aforementioned, geared towards an aging population. Seniors partake in coffee, tea, alcohol, etc., which contain stimulants, and many serve to dehydrate not hydrate.

It is believed by the inventor that children need special dietary support, along with education, educating while entertaining works best for children. For the most part, our younger generation is drinking beverages with far too much sugar clothed within Coca-Cola®, Pepsi®, Mountain Dew®, and like products. Also they contain stimulants such as caffeine, and assorted acids, (such as phosphoric and citric acid) which may play an important role in the health of their gastrointestinal tract later in life.

Children certainly like going to restaurants, parties, celebrations, and ceremonies, especially those revolving around known holidays. It is at these affairs that parents have the least control over their food and drink. However, and regardless, children need good quality nutrition everyday and good quality beverages, which hopefully will also ensure optimal hydration, which is extremely important.

Children only have beverage options within the scope of what is commonly available: milk, mostly cow, some goat, soy, rice, etc., soft drinks. There also exist fruit juices, fruit juice blends, and the like, which also carry with them a high percentage of sugar. Additionally, there are drinks like punch and lemonade which also high in sugar.

An entire segment of a recent television show, 20/20, featured data showing how bad caffeine is for children, and in fact the popular soft drink, caffeinated Mountain Dew® cannot even be sold in Canada. Fruit juices, while containing some vitamins, are very high in sugar. The popular fruit drink Hawaiian Punch® and Kool Aid® drink mixes are basically little more than sugar and flavoring. Hyperactive children, and children with attention deficit disorders (ADD), are negatively impacted by excess sugar. While some beverages, such as sodas, with artificial sweeteners contain virtually no calories, they do contain potentially hazardous chemicals for sweetening, and whereby many additionally contain caffeine.

Many of the beverages provided for children are high in calories. Many of the beverages fill children with the "empty calories" so that they do not have room for healthy foods. Literature is replete as to how overweight our younger population is today, and the potential of serious consequences later in life if this is not handled at an early age (diabetes and cardiac problems just to name a few).

Sugar is also referred to as "Liquid Candy", at least that is the name that the United States Government has used to refer to the sugar loaded, non-nutritional sodas, still popular today. In a recent article—"Liquid Candy: How, soft drinks are Harming American's Health" by Dr. Michael E. Jacobson of the Center for Science in the Public Interest (CSPI), states that "carbonated soft drinks are the single biggest source of refined sugar in the American Diet". Wire alarming is the fact that soft drinks are the fifth largest source of calories in adults. Further alarming is the fact that children start drinking soda pop at a remarkably early age.

The problems associated with these sugar laden soft drinks, and the increase of empty calories found in these sodas are as follows: obesity, decreased bone health, tooth decay, heart disease, Kidney stones. Dena Mehlberg R D of the Froedtert Memorial Lutheran Hospital in Wisconsin advises consumers to get enough fluids each day, the average person needs 8-10 cups a day, and make healthier choices when selecting a beverage.

The inventor here hopes to dissuade, especially the younger population, from "Liquid Candy" and in some instances fruit juices, which have a very high sugar content and none of the fiber benefits as compared to eating the fresh fruit itself. While milk is an important source of calcium, for those who are lactose intolerant, the lactose in milk can present digestive problems, especially in Asians, Hispanics, and Blacks.

The inventor is extremely concerned that there exist the proper nutrition for children, especially health challenged children, and those of indigent and/or lower income families. Additionally, it is important to the inventor that we look at how to help people and animals all over the world especially children.

All that has been mentioned so far is not specifically related to children, but there does exist a bent towards that group. This is probably because responsible individuals can impact children, and if done at an early age will make a considerable difference with their present and future choices. Water is considered boring to many children and really, what are the RTD options?

Therefore, the inventor is hopeful that the present invention will address many, worldwide, where healthy RTD beverages even if they exist, would have to incur the costs, etc. described earlier and/or production, if it was even possible in some countries. The inventor truly believes that this invention promotes a possible way we can help address "health through better drinking".

Again, note that there are different tastes and other culture related factors. Once in production, variations can be adjusted accordingly. Again, to be noted is the fact that in many areas of the world pills and capsules and/or the like are so foreign to the population at large. Additionally, we don't always want to give children pills and capsules in our own country. The inventor feels that this may give a negative impression of the United States. We don't want to be the country that sends drugs, and/or product in commonly recognized drug like form and/or drug-like fashion.

Additionally, and of great importance, children must be hydrated properly. Further, many of the beverages in the marketplace are not hydrating because they contain excess salts, sugars, or diuretics, (e.g., caffeine).

For an active child weighing 50 pounds, one quart of water is needed per day. Water is not the choice of children. Children, drink water from drinking fountains at school, the park, etc. They especially need hydrating beverages when they are sick, and especially even more when they have high fevers, as water is lost. Further, water helps to regulate body temperature. It is most difficult to get children to drink water at all, let alone at times of illness. Parents and/or caregivers usually give water with vitamins and necessary medications, but just like the drinking fountain situation, children usually consume this water in inadequate sips.

There are many powdered beverages in the marketplace that must be reconstituted prior to consumption. Some of these are meal replacement, or diet powders such as Slim-Fast®. Recently several similar products have come to market for the younger set. These are often of the meal replacement type—Kids Plex® by Naturade® and Animal Parade® by Natures Way®. In the reconstitution of these, as well as the earlier mentioned powder for the adult population, additional nutritive and/or specifically designated ingredients may be added by first enriching, using the present invention, the liquid to be used for the preparation.

In the past to encourage children to do things they aren't normally inclined to do, parents and/or caregivers have contrived all sorts of games and offered rewards. A drop of candy was place at the bottom of a cup, often in the case of milk, as a reward for drinking the entire beverage. The present invention includes a beverage infusion delivery system that, while it is designed for all humans and animals, is particularly appropriate to the children's marketplace.

Children like to feel grown up and love to imitate well-known grown up activities. By presenting a new and novel way for them to make, reconstitute, and/or brew their own drinks we are providing a grown up activity with good intentions.

We are an interactive society and this is a personal interactive experience, which can be done alone or shared with others. For children especially, it is most valuable to have an infusion packet that will allow the process to occur in other than potentially burning hot water. Burns are always a concern of parents. Additionally, hot liquids are usually sipped and children, unless pretending such as at a tea party, usually don't sip.

Effervescence may or may not be present, in whole and/or in part. It is an exciting technology and children often time really like it. Certainly, it has its visual place as it "bubbles up". Additionally, for those so hooked on carbonated sodas and the like it will serve to be a replacing, value and/or value added, constituent.

By adding various water-soluble functional pharmaceutical and/or nutritional supplements to an infusion packet, it is possible to provide a unique delivery system for the supplements. Each infusion system represents a precisely measured delivery device for enjoyment, entertainment, and/or additional added health benefits such as pharmaceutical and/or nutritional supplements. To the inventor's knowledge, this vehicle has not been taken advantage of hitherto.

While fiber, especially soluble fiber has been mentioned early on, it is necessary to present more information for a further qualification and description of this invention.

Up until now, one of the problems has been to provide a convenient vehicle for soluble fiber, especially if it is to be combined with one or more additional additives. The infusion system herein described can provide the ideal vehicle for soluble fiber(s). While it is know that packets of soluble fiber exist, Metamucil® as one, what is not known is if certain blends and/or combinations of fibers can be commingled without consequences. A further unknown is the ability to be combined with other fibers, as in regard to shelf life and/or the like as well as other ingredients.

Additionally, some of the fibers may be presented in very fine powder form. To package those fibers loosely within a packet is not always desirable because some of the fiber may adhere to the inside of the packet and/or lodge within the folds of the packet, especially in the corners. A further negative to the fine fiber powder being packaged loosely is that when you rip open the packet it can literally fly all over.

Therefore, in relation to the present invention, whereby a measured dose of soluble fiber can be enclosed in the infusion system is considered ideal, using this infusion packet system, one more efficiently guarantees that all the fiber will be made available, and therefore a more accurate dose administered.

The precise dose, ratio, and/or blend of fiber(s) per packet may be determined by the specific need/use of the consumer. While there may be many different choices of fibers, blends, ratios, etc. if there is a specific health condition being targeted then the amount, as well as the fiber mix, will be selected toward that direction. An example would be for diabetics. Additionally, other supportive ingredients, for general wellness, consumer acceptance, and/or condition specific situations, may be added for enhancement.

Dosages of soluble fiber falling between 0.01 and 50+ grams are readily accommodated and function well with either hot or cold liquids. Other more traditional infusion materials can be included. For example, it is relatively simple to produce a packet that provides "fiber tea." By introducing hot water to the packet, one rapidly produces a tea beverage with the added benefits of soluble fiber.

The tealeaves and the soluble fiber, depending on the fiber type, may be mixed together within the infusion packet. Alternatively, the packet can have a plurality of compartments, so that the tea (or other ingredients) can be kept separate from the soluble fiber until the actual moment of preparation. It is possible to use several different types of soluble fiber, and keep them separate in individual compartments. If any of the soluble fiber compounds, or additional additives used are hygroscopic, the entire packet can be sealed in a humidity-proof pouch.

Although traditional uses of infusion packets, more commonly known as tea bags require hot or warm water, certain soluble fiber carbohydrate materials are very soluble in room temperature and/or cold water as well. Thus, it is possible to provide a soluble fiber infusion packet that can be used in cold water.

Therefore, by adding soluble fiber to the aliquot of constituents used in the infusion packet we are able to address the over-all health benefits of fiber along with the specific, somewhat individualistic, properties of the fiber(s) selected.

Depending on the fiber(s) used it may not be appropriate to place them (one or more combined) directly in contact with the other ingredients. It is to this that the inventor looks at compartmentalizing as much as possible to protect each ingredient. It is not just the ingredients used, but also the manner as to how they are delivered which may be critical. Depending on the fiber used, it may carry with it other unique characteristics, such as serving as a pre-biotic and/or pro-biotic, an immune enhancer, a sweetening agent, and/or just used to enhance the mouth feel of the final beverage as just some examples.

The carbohydrate inulin, which occurs in over 36,000 plants, is all natural and non-digestible by the human digestive system. Inulin has been consumed for centuries by entire populations as a main staple in various food sources, such as onions, wheat, J. artichokes, asparagus, and others.

However, current consumption from natural sources is not large enough to provide an efficacious inulin dose (approximately 5 g/day minimum for improved physiological health) as a unique soluble dietary fiber and preferred food for healthy intestinal bacteria. (Good gut micro-flora such as bifidobacteria and lactobacilli).

1. In addition; inulin provides a myriad of health properties for which; under DSHEA, and further clarified by the FDA Apr. 29, 1998 in 21 CFR Part 101 Food Labeling Nutrient Content Claims, Definition of Term: Healthy, statements of structure or function may be made for mainstream inulin-containing products, e.g.
    a. "Promotes growth of beneficial bacteria such as bifidobacteria", "bifidogenic",
    b. "Helps to maintain a normal, well balanced gut micro-flora",
    c. "Helps maintain intestinal flora",
    d. "Stimulates natural Bifidus flora",
    e. "Inulin is efficiently converted to short chain fatty acid",
    f. "Helps maintain cardiovascular function and a healthy circulatory system",
    g. "Helps promote urinary tract health",
    h. "Helps maintain a healthy cholesterol level",
    i. "Helps to regulate blood glucose level",
    j. "helps maintain regularity",
    k. "Helps improve mineral bio-availability",
    l. "Supports the immune system".
2. Further impressive literature is replete with the benefits of inulin hailing its ability to:
    a. Suppress pathogenic gut microorganisms and their toxins,
    b. Prevent ulcerative colitis,
    c. and mal-absorption,
    d. Demonstrates positive influences on blood sugar regulation
    e. and also balance insulin for diabetics.
3. Further to improved
    a. Calcium absorption for osteoporosis
    b. and immune activation as related to disease prevention,
    c. Anti-tumor effects,
    d. Reduction in food allergies,
    e. and potential help for autoimmune diseases like
        i. Crohn's and
        ii. Rheumatoid arthritis.
4. In recent years, scientific evidence for reducing serum lipid levels in man, and animals, using inulin has grown (shown to lower LDL and raise HDL).

In food and/or beverage, inulin has neutral taste, odor, and color, and is ideal to be incorporated into an infusion packet blend.

The inventor has noted the following patents related to inulin as relevant; U.S. Pat. No. 5,972,415 to Brassart, et. al. (Nestec S. A. C H); U.S. Pat. No. 5,792,754 to Green et. Al. (Nutricia NL). Of most relevance is U.S. Pat. No. 5,721,345 to Roberfroid, et. al. titled "Prevention Of Mammary Carcinogenesis and Breast Cancer Treatment." U.S. Pat. No. 5,550,113 to Mann titled "Blood Sugar Regulating Composition and Methods Relating Thereto."

Also disclosed is a method for regulating blood sugar levels by administration of the composition of this invention.

The category of soluble fibers called gums has been previously mentioned. Gums are a natural addition to functional foods. Not only can they improve the appearance, stability, and the overall appeal of your finished product but they are also a valuable source of dietary fiber.

Of specific interest here, and to be included in the invention, is to use gums with known functional properties. Literature supports the following:
1. Guar gum improves:
    a. Insulin sensitivity,
    b. Blood lipids,
    c. and blood pressure; American Journal of Clinical Nutrition 56:1061-5; 1992.
    d. A study at the University of Minnesota confirmed that with the inclusion of guar gum the viscosity of the contents of the intestines was increased.
    e. Further, Benefiber®, by Novartis, is a guar gum used for the treatment of diarrhea.
2. Gum Arabic has been shown to
    a. Enhance water, electrolyte, and glucose absorption from oral re-hydration solutions in jejunal perfusion of healthy rats and in animals with theophylline-induced secretion or chronic osmotic secretory diarrhea.
    b. Gum Arabic while having perhaps a little effect on glucose tolerance and stool weight has been shown to have a positive effect on decreasing serum cholesterol.

Additional water-soluble flavoring agents, and/or sweetening agents, can be included to provide a tasty fiber beverage that is produced by dropping the infusion packet into other than hot water.

Again, the various components may be mixed together in the packet, or can be compartmentalized. Regardless of water temperature, some of the soluble ingredients inside the infusion packet can advantageously be provided in the form of tablets, pellets, capsules, granules, and/or breads, etc. as opposed to just powdered ingredients. This militates against the ingredients sifting through the pores of the covering material. As is known in the art, certain micro-bead configurations can be formulated with extremely rapid solubility properties.

Then too, it may rest in part and/or in whole, as it is also a matter of design and choice. In an infusion system, thus described, as to how one may build a beverage.
    a. The user is provided a container holding, by name and function, multiple choices as to color, flavor, and supplemental ingredients.
    b. Then Within the confines of a "create your own packet and/or system", and just as if stacking blocks, these individual units may be affixed, hooked, strung etc., on a support member,
    c. and/or placed in a larger porous sack
    d. and then dunked into the receiving liquid, regardless of temperature.
    e. This can be fun for children, and can serve as a learning experience as well in multiple ways.
    f. Perhaps via this invention, we just might bring up the next generation of beverage developers.

The inventor does not ignore the vast number of botanical products that exist in the form of a tea bag that are placed in hot water, to imbibe the water with the active constituents. In fact it is almost commonplace to go into a restaurant and note that one can order a cup of tea whereby the patron is brought a cup of hot water along with a container, many times a humidor, of an assortment of teas to choose between.

However, and a claim of this invention is a system whereby the patron can order a bottle of safe water, with or without gas, and be brought a similar container filled with infusion packets specifically designed to go in to, other than hot water.

Conceived also may be packets specifically designed for waters with gas as opposed to waters which are flat. It is of major importance here to note that one or any number, and/or description, of the components of this invention with or without a support member is implied. This has been covered extensively in detail under Business models and methods.

Other Active Ingredients

The invention set forth here includes, one or more functional and/or active ingredients which functions independently and/or in combination with true tea, tea solids, the like, and/or one or more herbal constituents, and/or any combination of the aforesaid.

As example the inventor is most focused on dietary fiber, antioxidants, diagnostics, pro-biotics, pre-biotics, digestive and systemic enzymes, yet still remains conscious of the need for vitamins and minerals, especially those which are most difficult to find in preferred food choices, and/or in a combination which plays to greater absorption.

Additionally some individuals, for a multitude of reasons, do not break down foods properly, and/or absorb their nutrients properly. Further, due to some health conditions certain foods are not advised, and yet those very foods may carry with them the nutrients that can be of value to the consumer. It is for these reasons, and more, that the inventor is aware and attempts, through this invention, to address and make possible the delivery of ingredients, with integrity, in the most bio-available manner, while at the same time making the experience a pleasurable one.

Other than soluble fiber, the inventor specifically favors active ingredients, which permit the creation of a beverage containing those active ingredients for which there exists sound science. U.S. Pat. No. 5,981,498 to Fukuda, Miyake (KKHSKK Okayama, JP) titled "Agent for improving blood circulation." U.S. Pat. No. 6,008,252 to Beale titled "Method for increasing muscle mass." U.S. Pat. No. 5,888,514 to Weisman titled "Natural composition for treating bone or joint inflammation." U.S. Pat. No. 5,716,976 to Bernstein titled "Method of treatment for carbohydrate addiction." U.S. Pat. No. 5,820,867 to Bewicke titled "General anti-depressant-composition for dietary supplement." U.S. Pat. No. 5,741,491 to Jones (Isotechnika Inc. CA) titled "Medicinal composition for diabetes. U.S. Pat. No. 6,025,363 to Giles titled Composition for suppressing appetite."

The inventor notices that more and more patents are rightfully issued in the nutritional category, thus new delivery systems are needed so that the public can take advantage of these formulations designed for specific needs. Our culture is leaning more towards functional foods and beverages and getting away, from pills, tablets, and/or capsules.

However there may be a serious drawback when incorporated into foods and beverages. The inventor is greatly concerned that due to combining, processing, handling, and/or the like of the aforesaid the active ingredients may not remain active and/or bio-available to the consumer. Any ingredient, let alone sensitive ones, may not withstand the technologies necessary to stay active in a food/liquid medium, especially, liquid, in the presence of the acids that are used to prevent microbial growth.

Some examples are as follows; which also by the way reinforce the need for the development of new delivery systems: U.S. Pat. No. 6,265,450, Jul. 24, 2001, to Asamu et al., (Suntory Osaka JP), titled "Anti-stress composition", U.S. Pat. No. 6,268,011, Jul. 31, 2001, to Hoie (Nutra Pharma (Oslo NO.), titled "Composition and its use as a food supplement for lowering lipids in serum"; U.S. Pat. No. 6,264,997, Jul. 24, 2001, to Yamakoshi, (Kikkoman Corp. (Chiba-Pref, JP), titled "Anti-arterosclerotic food"; U.S. Pat. No. 6,207,638, Mar. 27, 2001, to Portman, (Pacific Health Laboratories), titled "Nutritional intervention composition for enhancing and extending satiety"; U.S. Pat. No. 6,224,873, May 1, 2001, to Jones Zhishin LLC (South Burlington, Vt.), titled "Regulation of appetite body weight, and athletic function with materials derived from citrus varieties"; U.S. Pat. No. 6,255,341, Jun. 3, 2001, to De Michelle, et al., Abbott Laboratories (Abbott park IL.), titled "Product and method reduce stress induced immune suppression"; U.S. Pat. No. 6,261,610, Jul. 17, 2001, to Sher et al. Nestec S. A. (Vevey, C H); titled "Calcium-magnesium fortified water, juices, beverages, and other liquid food products and process of making"; U.S. Pat. No. 6,261,589, Jul. 17, 2001, to Pearson et al. titled "Dietary supplement nutrient soft drink composition with psychoactive effect".

It is critical to the invention set forth here that each packet be consistent in containing the represented amount of inactive, and/or active ingredients. It is difficult at best in production to weigh out ingredients, especially if the ingredients are of varying weights. U.S. Pat. No. 4,959,947 to Reif (Motan Verfahrungstechnik GmbH & Co. Weingarten, Del.) teaches an apparatus for the production and packaging of a compound mixture, in which extremely accurate and rapid weighing-out, proportioning and packaging of individual components are achieved.

Potency

Each infusion packet should be proportioned to correspond to a specific quantity of liquid. One added advantage of this kind of a delivery system is that the consumer may strengthen and/or weaken the solution by reducing and/or adding more liquid(s) during preparation. The only part that should not be compromised is any means of preparation, and/or consumption, that would impede any and/or all individuals from not receiving the full benefit of any or all of the beneficial agents.

Proportions/Container

The packet may be sized, amount/concentration of beneficial agents, so that it correlates with not only a specific amount of liquid, but to also fit within a specific container that holds the proper volume of liquid. This may be portioned in single or multiple servings. If used for animals, it should be proportioned accordingly.

This invention may also include a container that, not only is size appropriate to the system but, may bear any graphics, advertising, characters, theme for the consumer, for ease of use, convenience, and/or to enjoy.

As an example the inventor also envisions, for children, the very famous Alice and Wonderland Mad Hatters tea party. Not only can each participant have their own "cup" and infusion packet, but an alternative system where by the pot/pitcher carries on the theme and holds a portion that will equally fill all the cups supplied with the "set". This can give the added advantage of a giant infusion packet, with or without a support member, going into the container of liquid. Also in the case whereby it may be desirous for the children to have a warm drink, an adult can guide them more easily by supervising the mixing, and then ultimately the pouring into individual serving cups.

Delivery Rate

Another advantage of this invention is that, unlike with a uniform capsule and/or a tablet unless specifically timed released, the beneficial ingredients are most often consumed/ingested all at once.

Studies have documented that with certain medications and/or supplementations less may be needed, and/or better delivered, if given slowly, over a specific/longer period.

Usually this is accomplished using inter-venous, nasal-gastric, inter-gastric (gastrostomy) delivery systems activated by gravity with control flow regulators, and/or pumps.

With or without time-release ingredients it is a further object of this invention to control the delivery by drinking, and/or spooning, the carrier liquid at an instructive rate. This invention thus makes it possible to indicate, by personal individual instruction and/or printing on the package, the serving portion verbiage along with the ideal or close to ideal rate of consummation.

As an example, the consumer may receive instructions that indicate that the consumption rate is to be in increments, say over one (1) hour. This includes the possibility of constantly taking small sips, or a modulated amount like quarter of a cup every fifteen (15) minutes.

An example would be a liquid containing a larger than regular amount of Vitamin C. While it can be done, it is not really considered to be cost effective to time release Vitamin C, nor does Vitamin C contribute a horrible taste, and/or after taste, so as to warrant coating to by pass the taste buds. This particular vitamin, in large dose may upset the GI tract (diarrhea; etc.), and/or additionally, because it is not stored in the body, pass quickly through to be excreted in the urine. One often hears of people taking many supplements and having expensive urine.

Much of this has to do with the fact that the body cannot absorb quickly, and/or has problems with absorption.

Color, Flavoring Fragrance/Aroma

These areas are of special importance to the inventor mainly because they so affect the product, and therefore consumer compliance and acceptability.

The inventor has taken note that with all the billions of tea bags produced over time, that no one has colored and/or graphically printed on the tea bag material, including and/or not including a connecting device to a tag, and/or the tag itself, and/or colored a bag per se by using colorings with the unique nature whereby the colors may change based upon coming in contact with moisture, or in response to the temperature of liquid, and/or governed by changes in light, and/or a combination of light/heat, independently and/or simultaneously.

The colors contributing to the liquid exclusively may contain non-active and/or active ingredients, which may, when wetted, totally and/or in part contribute color, and/or color along with flavor, and/or fragrance, and/or additionally enhanced ingredients to the final ready to drink, or spoon, liquid for consumption.

It is to be understood here that the receiving liquid may already be colored, flavored, and/or contain beneficial ingredients. However, the just aforesaid is designed to further enhance, by any or all of the above, what is existing, and/or deliver other beneficial, and/or agents which may bring forth a more valued liquid, and/or create a synergic effect. Just one example would be making the active ingredients more bio-available to the intended user.

Figure 8:
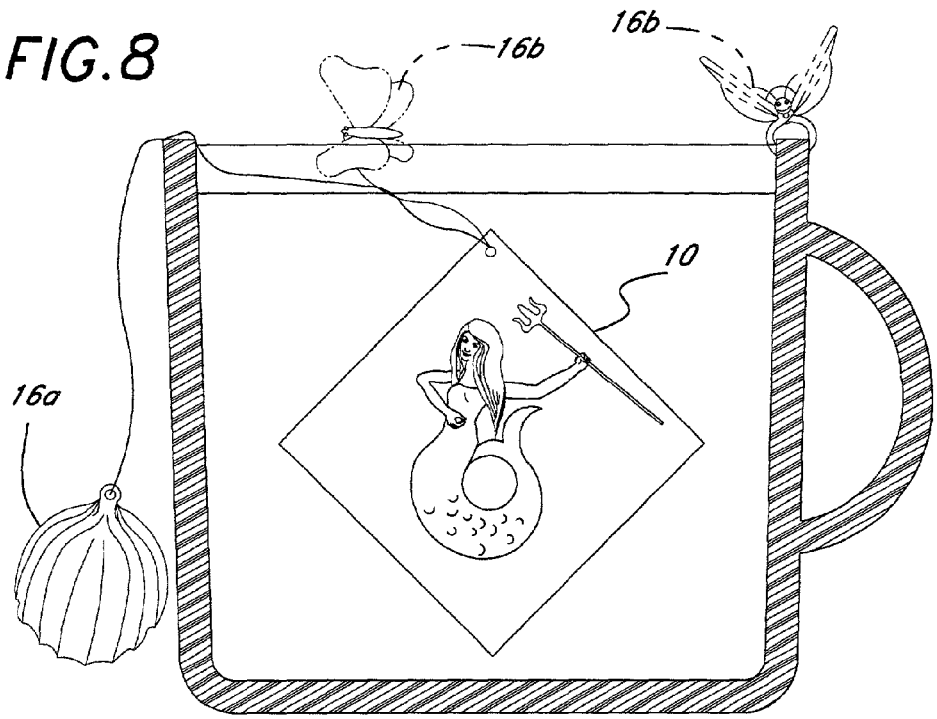
FIG. 8 shows an infusion packet with a visible printed design that is related to the tag, which is a charm bracelet charm. A clip tag is also pictured.
Figure 9:
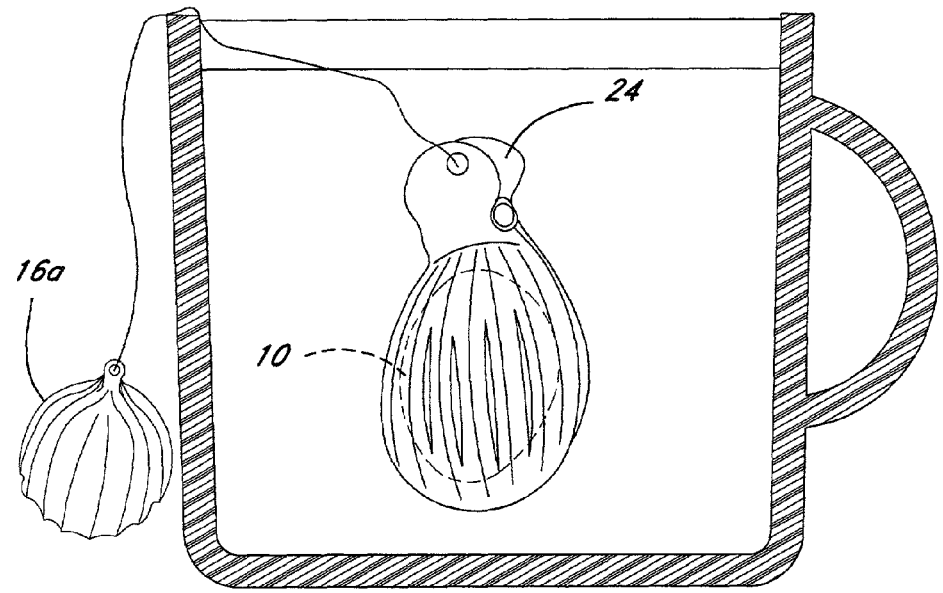
FIG. 9 shows a support member that encloses an infusion packet.

Coloring agents, as studied by the inventor include but are not limited to the following: a red and/or a red-orange pigment made from the antioxidant lycopene found in tomatoes and watermelons. U.S. Pat. No. 5,965,185 to Hartal, Raveh, Wolf, (IL), titled "Stable lycopene concentrates and process for their preparation." U.S. Pat. No. 5,993,880 to Frost & Saleeb (Kraft Foods Inc., IL), teaches a new form of green color prepared by specially treating copper chlorophyllin. The art further recognizes the use of vegetable extracts as colorants and additives to the food industry: U.S. Pat. No. 4,851,339 to Hills titled "Extraction of anti-mutagenic pigments from algae and vegetables:"; U.S. Pat. No. 5,019,405 to Sapers, titled "Process for manufacture of maraschino cherries in a dyeing process using cartenoids"; and U.S. Pat. No. 4,853,235 to Tomomatsu (The Quaker Oats Co., IL) Color changing cereals and confections." Disclosed in the later is the ability of a cereal, and/or a confection, to change color when immersed in an aqueous medium. For example, FIGS. 8 and 9 illustrate a liquid induced color change in the context of the present invention.

Refreshing sensations often feel good, and often just make the consumer feel better. An example of this might be all the breath addressors on the market, which do no more than refresh the mouth. The inventor takes note that it is possible to do this with the liquid and therefore refers to U.S. Pat. No. 6,214,788 to Velazco (Firmenich S A; Geneve C H, titled "Use of cubebol as a flavoring agent." The aforesaid patent discloses a method for imparting perfuming, flavoring, or refreshing properties to a composition, or product, for a seriously protracted period of time. (NOTE: the refreshing effect develops in the mouth after delay of approximately 1-2 minutes and, lasts for about 30 minutes).

Aroma may play a very important part of beverage delivery, especially when consumer compliance and acceptance is desired. There are many flavored waters in the market today that use, in combination with the flavoring, the same fragrance to enhance the experience.

Additionally, a compatible, different, aroma may be used to operate synergistically, whereby a blend is desired/accomplished (e.g., strawberry/banana).

Also on the market are bottle caps, made by Sentations, whereby the aroma is impregnated into the plastic cap itself. U.S. Pat. No. 6,102,224 to Sun, et al. (Pepsi Co., NC) titled "Aroma release bottle and cap" discloses a technology with a method and apparatus for delivering an aroma when a bottle is opened. They employ a scratch and sniff material to contain the aroma. The material is scratched when the cap is removed, thus releasing the aroma. More about aroma will be addressed later, and specifically to a component of this invention, carrying aroma, which is in relation to the tag when it is adhesively attached to a bottle.

Temperature Desirability/Dissolvability

In all instances, the packet is designed to allow the penetration of and into liquid, mainly water, either temperature specific or non-temperature specific as determined by the contents, and/or the intent of the product. The nature of the ingredients, as well, as how they are formulated, (e.g., powder, granules, encapsulations, etc.) may dictate/serve as a guideline(s) as to the temperature of the liquid preferred so as to activate, and/or maintain, the integrity of the ingredient(s) (temperature sensitivity).

In the case of a child, one would want to refrain from using potentially burning hot water and thus would want the ingredients to be readily dispersible in a "comfortable to the touch" liquid. This may also be most important for seniors and/or those with any difficulty handling seriously hot water, either by mouth and/or when mixing.

When mixing, in other than hot water, it may be desirable and/or necessary that the ingredients totally dissolve and dissolve rather quickly. All is with the understanding that the openings are selected so that the contents are effectively retained. An example of the just mentioned would be the products Kool Aid® and Crystal Lite®.

In some instances, especially with encapsulations, it may be undesirable to totally and/or partially dissolve into the liquid for the obvious (timed release, taste, etc.)

What must be kept in mind is that any remaining undissolved parts/particles must not interfere with one's ability to swallow the resulting liquid. However, it is possible to have a swallowable particle(s) enhance the texture of the liquid. There are beverages, and even in non visible to the eye beverages, in cans in Asia which incorporate small seeds (chia, poppy, etc.), that one swallows in conjunction with the ingested liquid.

This concept departs considerably from the usual botanical material of an infusion packet (tea bag, etc.), whereby the materials contained are leaves, flowers, petals, buds, stems, roots, etc. U.S. Pat. No. 5,965,162 to Fuisz, Cherukuri, Kota, Suresh, Stewart, (Fuisz Technologies Ltd., VA.), discloses a process for preparing comestible units which disperse quickly in the mouth using fuse and compression technology. The crystallization of ingredients, as demonstrated in U.S. Pat. No. 5,866,188 to Batist, Meyers, Fuisz, (Fuisz Technologies Ltd., VA), titled "Comestible composition having spheroidal crystal sugar", addresses this potentiality and methodology. U.S. Pat. No. 5,549,757 to Morano, (Ingredient Technology Corporation Innovative Sweeteners, NJ), titled "Process for recrystallizing sugar and product thereof" is another example.

To make product for inclusion in the infusion packets the inventor is aware of the agglomeration process, and additionally the lyophilization process: See U.S. Pat. No. 5,051,269 to Noreille, Pot Nestec S. A. (Vevey, C H), titled "Agglomeration method." U.S. Pat. No. 5,554,400 to Stipp, (The Proctor and Gamble Co., OH), titled "Infusion beverage product comprising co-agglomerater creamer and sweetener suitable for bag and filter pack brewing." U.S. Pat. No. 5,616,355 to Haast, Harrell, titled "Lyophilized health food products and methods of making same."

Candy/Confectionery Element(s) in Packet

The presentation can include an additional supplemental product, which may be considered a standalone food in and of itself, and/or by virtue of the beneficial ingredients, supplement the ingredients in the packet.

The inventor is most interested in the inclusion of active ingredients in confections (candies). U.S. Pat. No. 5,928,664 to Yang, Oh, (Fuisz Technologies Ltd., VA), titled "Consumable gummy delivery system" also teaches the inclusion of active ingredients admixed with a glycerinated gelatin matrix. U.S. Pat. No. 5,626,896 to Moore, et al. (A.E. Staley Manufacturing Co. Decatur, Ill.) titled "Method for making liquid centered jelly candies" discloses related information. While this patent deals with liquid filled jelly candies, there exists in the market, center fill co-extrusion technologies used to fill primarily hard candies with jam-like material. U.S. Pat. No. 5,578,336 to Monte, (AZ), titled "Confection carrier for vitamins, enzymes, photo-chemicals and alimentary vegetable compositions and method of making" gives an example.

It is conceived by the inventor that one and/or more of these various types of candies, which may or may not include some or all of the elements disclosed anywhere in this application, be aligned with a so classified candy/confection product. Candy certainly is a big business worldwide (about 79 billion dollars internationally and 23 billion dollars domestic U.S.A.). Candy can be messy, stick to itself, and further it is most difficult to stop, with "just on piece", or even several. Candy, with or without sugar, has proved to be addicting. Just as in anything, moderation is the best alternative. However, that is easier said than done.

Now with the abilities, and/or the technologies available, to be able to add additional elements as well as nutritive value, and further, there exists the ability whereby these types of confections can be broken down, if not just by the water then with the addition of elements to the candy(ies, itself, and/or "a break down element", be positioned anywhere on/within the packet, and/or impregnated into the packet). Therefore it is now possible to include one, and/or more pieces, of what may be considered to fall under the classification of confections to the invention set forth herein.

In other words, it is contemplated that inside the infusion packet can be placed a gummy candy and/or anything classified as a confection.

The only requirement is that it is fabricated so as dissolve totally and/or in part to add to making a beverage. If it does not totally dissolve, then it is here set forth that the enveloping material and/or any part be rendered edible and can be chewed, and/or the like by the consumer.

It is also contemplated that, with the manipulation of materials, the enveloping material may dissolve first and leave the "confection(s)" to dissolve more slowly, or remain fairly intact so that it becomes the proverbial cherry on top of the Sunday, to be consumed separately, and/or as a reward, especially by children. Again, this can work in the reverse and the inside confection disappear leaving the exterior as the reward. Further, if more than one confection, and/or confection-like, object is enveloped then one and/or more can disappear, and/or fractionalize, to the awe and enjoyment of the consumer. Especially noteworthy is if the confection is recognizable to the child. This added character/object representation will serve not only to have the child participate in the making of the beverage, but delight more in receiving the so called reward by getting the one or few candies. The extra few candies, as aforementioned, more than likely will carry active nutritive ingredients. Although it is not required that they do so, it is important to note that the beverage will address hydration requirements. Further, here in lies an interactive learning situation for the child, and with that comes forth-additional basic scientific understandings of how properties work, and/or interact.

Children have fiber requirements too. Many gums are fiber so that another aspect of the invention is disclosed. The candies can provide fiber, contain additional fibers, and/or additional fiber may be provided within any portion of the infusion packet. This then becomes a significant part of this part of the invention, whereby a consumable delivery system for active ingredients, comprising of a plurality of candy composition carriers comprising a plurality of active ingredients, whereby the composition is enclosed in an infusion packet.

Taste/Flavors and Encapsulations

While it is possible to make attractive looking products, one also needs to factor in taste. The inventor is most sensitive to the fact that many ingredients, which fall under the "good for you" category, do not always taste good. This shall be addressed in more detail under encapsulations that may or may not include liposome(s). Meanwhile the inventor has taken special note of the following: U.S. Pat. No. 5,927,052 to Nippes, Klein (Teepak, Meerbusch, Del.) titled "Method and device for flavoring tea and tea-like"; U.S. Pat. No. 6,022,576 to Cirigliano, Farrell, McKenna, Thomas, Rothenberg (Lipton C., NJ), titled "Flavoring materials for use in tea containing beverages"; U.S. Pat. No. 4,851,252 to Greither, (Bruchkmuhl, Del.), titled "Composition and process for the production of a mixture for a tea drink with fruit"; and U.S. Pat. No. 5,633,027 to Cherukuri, Battist, Zamudio-Tenna (Fuisz Technologies Ltd., (VA), titled "Confectioneries containing stabilized highly odorous flavor component deliver systems."

Encapsulations

The description of encapsulations with references has been fully developed in an earlier portion of this invention: however the inventor here wishes to make a specific reference to the importance of encapsulations as related to.

Digestive Conditions

Today, 70 million Americans suffer from digestive diseases, 15 percent on a daily basis (NIDDK 1997). An even larger population, approximately 118 million, experience heartburn or are afflicted with gastro-esophageal reflux disease (GERD) at least once a month. Even more potentially alarming is the projected 35 percent increase in the number of adults, 50-64, who will be afflicted with digestive problems. It is estimated in America that 90 million people use antacids or other stomach relief Medicines (Euro Monitor, 1998). Next to headaches, stomach problems are the most self-treated ailments in the U.S. (American Pharmaceutical Assn., 1997). Further one of the strongest health links for nutraceuticals is the treatment of digestive problems.

The inventor believes that much of these problems are caused by overly acidic beverages used, and/or over-used, and/or over any period of time, (most likely years).

To produce beverages today with a long shelf, life, care must be taken to be sure that the liquid is free of microbial contamination. Therefore, the Food and Drug Administration (FDA) has set specific guidelines for the production of Ready to Drink (RTD) beverages. Because of the cost of production, and the fact that that cost would be passed on to consumers, beverage companies cannot afford expensive production technologies and/or the need to refrigerate with a very short refrigerator life, and/or shelf life.

The most widely used and accepted method is to make the drink highly acidic, (pH<4.5; the lower the pH the better). Note: most non-alcoholic drinks today fall into the 2.5-3.7 pH range including all the soft drinks, teas, coffees, botanicals, new age beverages, etc. The most commonly used acids are: citric, malic, and lactic. While precautions are a must in production, more often than not, when ingredients are delivered in dry form the guidelines differ from a moistened, rewetted, or solubilized-in-water finished product.

Further, as we age we loose our ability to produce not just quantity, but a good quality of digestive enzymes so necessary to break down foodstuffs.

It is the goal here to provide a healthy answer to the above: by using well-researched ingredients, non acidic, and/or low acid ingredients and/or methods whenever possible, along with and/or delivery vehicles such as encapsulations, whenever possible, regardless of size, color, and/or of materials, including but not limited to liposome(s), to address and support digestion, along with an increased ability of promoting a healthy digestive tract environment.

Tether/Connecting Member and/or Device

Although the packet may be simply thrown into water and later retrieved with a spoon or other appropriate tool, the packet often has an attached string 13 or similar device so that the packet can be "tethered" and readily recovered at the end of the infusion period. U.S. Pat. No. 4,609,556 to Goedert, presents a filter bag adapted to be maintained by means of an ordinary spoon in order to keep the bag from floating to the top; and/or a more desirable and easier way to remove the bag from the liquid.

The inventor has looked at other connecting devices and/or an attaching devices, that is, an extension of the packet, be it a firm straw with another function, and/or a firm stick, or twisted object, and/or the like. It is here conceived in this invention that the tethering device also may be a string.

As a string, it is conceived that the end of this string maybe positioned a loop to go around the finger, especially for a child. Said loop may be attached to a coil like member as opposed to a string. It is also conceived to attach a ring, plain and/or with decorative elements, to the end of the tethering device, that can be easily removed and kept by the child afterwards.

The inventor believes that removing the infusion system and/or packet can be especially messy as it is wet and likely to drip. Disposing of it may also be problematic, as well as inconvenient. Especially noteworthy is if the consumer is "on the go", in the car, at the gym, at a sporting or entertainment event, as just presenting a few examples. To address the just mentioned, it is the intent of this invention to provide a solution, and a solution with more than one value.

If the invention is to be used in a bottle of water, as an example it is understood by the inventor that the size, ergo height of the bottle, changes due to the volume of contents inside. To that end, a taller bottle would require a longer string, tether between the infusion packet and the external tag/fob. Therefore, a longer string would be provided so that there is ample length for the infusion packet to sit on the bottom of the bottle and, additionally, provide ample length to extend outside the bottle to at least, no less than, the midline of the bottles exterior. As an example using a 50.7 oz. (1.5 l) bottle, with a normal height of 12 inches (30 cm), one would provide a string no shorter than about 18 inches (45 cm). It may be also desired, and/or necessary, to provide a weight of some sort; and possibly, in consort with the tag/fob, a counter weight that would be safely attached.

The tag/fob is not always desired and/or necessary, but may be preferred, especially if it provides an additional major benefit. While the tag/fob of the current invention can be made to any size, shape, decorative, etc. and/or any suitable material, other than the usual paper and/or paper-like material, it now may present the additional ability, and option of, and carrying with it, an adhesive backing, most likely made of a film; plastic, paper and/or a paper-like material etc. The backing can be pealed away affording the ability of attaching the tag to the outside of the bottle. Therefore, with this aspect of the invention, and in this fashion, the consumer does not have to fiddle with a hanging string etc. While this ability is not new, in and/or of itself, the adding of aroma to the adhesive is.

Adding Aroma to the Tag

While "scratch and sniff" technology has been used for years, so has the ability to impregnate materials with ingredients by using special mechanisms of release to deliver to a specific cause/site, fragrance. Further is conceived the ability to provide an aromatic experience for the consumer.

As an example, 3M's Packaging System's division offers many options for attachment packaging. Most noteworthy; and also a 3M development, is their transdermal, and/or transmucosal, delivery systems. Based on that technology, 3M have developed a technology by which to impregnate a material with aroma. This is done by protecting the material with adhesive, or in the layering of material, and/or embedding fragrance in the adhesive material itself. The aroma is released when the protective portion of the adhesive is pealed off/removed.

The object here is to provide an aromatic experience for the consumer, other than what emanates from the beverage inside. This invention then obviates the disadvantage of not having an open beverage container, whereby the scent may more readily be apparent. Energy Brands of CT has fruit-water products in wide mouth bottles so the consumer may readily smell the essence. U.S. Pat. No. 5,885,640 to Anderson, (Nestec S. A. Vevey C H); teaches a package which provides for an aromatized headspace, by mixing the aroma with gas. In this case Nitrogen would be an excellent choice.

This aroma will serve to enhance the flavor of the beverage by mirroring the ingredients, (cherry, lemon, orange), in the packet and/or compliment the ingredients, (chocolate aroma to a cherry flavored beverage), or any combination thereof while, at the same time, securing the tag to the outside of the bottle.

By placing the aroma tag close to the consumer's nose, the tag is close to the opening, even placing it in alignment with, and/or over, the screwing groves, the more available the scent is to the nose of the consumer during consumption of the beverage.

Support Members

While the inventor has devoted much time to discussing support members, structures, materials and the like; the inventor wants to be sure that they are completely understood.

Through out history of the world, and existing in multiple cultures there are rituals centered on and/or around eating drinking, smoking, (i.e., the Indian peace pipe, marijuana, etc.). While the fork is considered by most to be a more advance eating tool than chopsticks, chopsticks are still used. Additionally, the inventor has personally seen the delight, especially with children, who attempt to eat in this fashion.

We are a paraphernalia, gadget, technology driven society, which seems to be thriving on interactive experiences of every kind. To that end the inventor, in an effort to attract consumers and direct them towards healthier drinking, chooses to set forth as part of this invention, a combination of an infusion packet and/or packets with a support member. This is of special appeal to easily impressionable children and, "me too", teenagers.

Support member(s), in whole and/or in part, should be able to use all possible interactive technologies including; any light up noise making components that might need a power source such as; a battery (regardless of size), solar energy, fiber optics, and/or the like.

As related to this invention, it is to be noted that each individual/single packet may have its own support member. Further, one support member maybe included in a container with more than one packet.

Regardless, a support member(s) can facilitate ease of use, may serve solely as entertainment, a part of a promotion, a contest, or advertising, etc. and/or any combination of the above.

There are a variety of analogs to the support member that are currently used by the confectionery industry to deliver more product to the consumer in an entertainment, and/or and "edutainment" like fashion.

Earlier the inventor set forth the use of a confection itself as a delivery system combined with, and/or within, the infusion system.

Here forward there exists a focus, and should be of great interest to note, on how the confectionery industry has incorporated the use of toy, and/or toy-like, components as part of a dispensing mechanism.

Over time, one of the most easily recognized candy dispensers was the PEZ® container. This is a little pocket container that contains small rectangular sugared candies, that when activated brings forth one candy at a time. Bondi®, a Japanese toy company, has used a variation of the PEZ® theme using Pokemon® in the same fashion.

Today, there a numerous and quite elaborate candy and gumball dispensing machines. The very large candy companies, such as Mars®, mainly manufacture these for use These machines deliver candies such as the ever so popular M&M's®. Many of these machines have licensed characters on them. Additionally, battery operated lollypop holders are most popular. The handle turns the lollypop. Further the handles are often fashioned after popular animated characters. See U.S. Pat. No. 5,690,535 to Coleman, T.; Schlotter, W.; Coleman, P. A.; Schlotter, A.; entitled" Twin Spins Spin Pop." Also to the same inventors U.S. Pat. No. 5,676,988 entitled "U.F.O. Pop;" and U.S. Pat. No. 5,820,437 titled "Wacky Pop Noise Maker." U.S. Pat. No. 5,542,570 to Nottingham (Cap Toys Inc.) titled "Toy Dispenser with Feed Means" is also an example. U.S. Pat. No. 5,862,997 to Coleman titled "Pop-eye Pen and Candy Holder" should be included here. U.S. Pat. No. 5,897,022 to Mann titled Activity Gumball Dispensing Device" is also germane. The object of all of these patents is to capture the consumer combining entertainment with the treat.

Thus, it is within the scope of the concept of the infusion system's support member(s) of this invention, to have a support member with, not only moveable part, but manually operated, solar energized, and/or with multiple fiber optic and/or battery options, and/or other power sources, to provide movement, light, or sound: but a variety of other interactive and experiential aspects such as, "glow in the dark" capabilities, and/or glitter, edible and/or non edible, etc.

Interrelation of Support Member(s) and Infusion Packets

Figure 4:
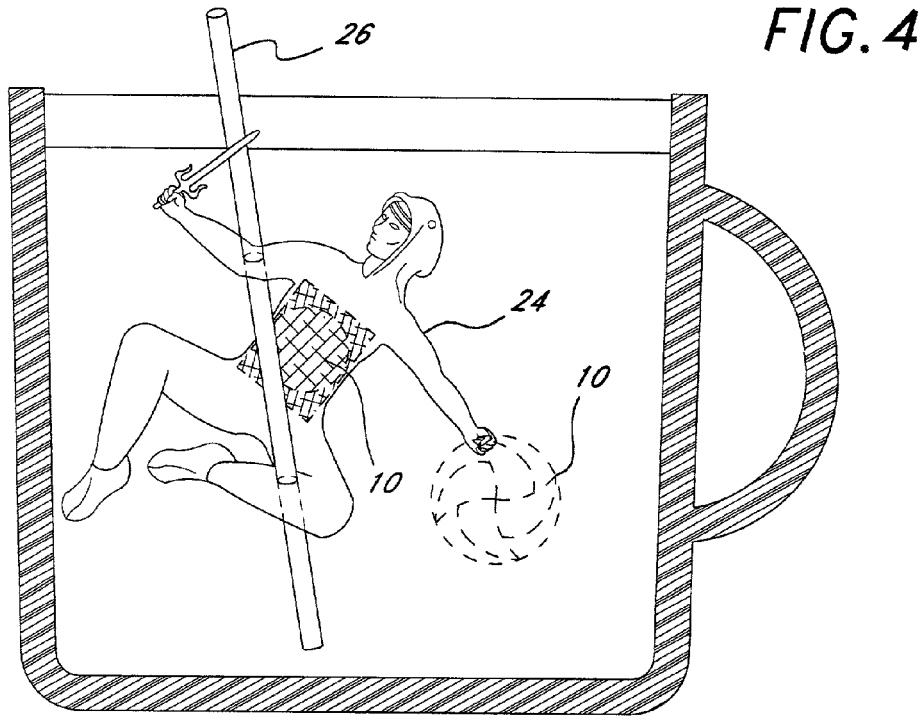
FIG. 4 is a sectional view of the support member of FIG. 3 to show one placement of the infusion packet.
Figure 5:
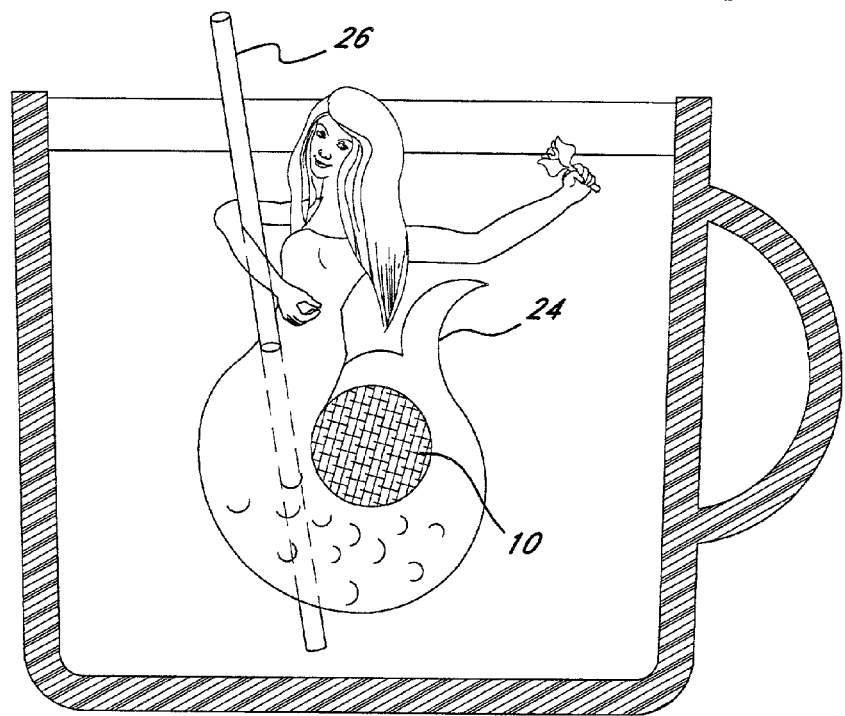
FIG. 5 shows an alternative design for a toy-like support member.

The infusion packet 10 may or may not be attached to the support member 14. If it is attached then there could be one support member for each packet. That is the support member may surround the packet as in FIG. 3 (also FIGS. 4 and 5). In addition, as shown in the figures, the support member can also serve to, support, a drinking straw 26. FIG. 11 shows an alternate embodiment where the support member is used to join individual infusion packets.

If it is not attached, then one or more support members may be in the container and be used interchangeably. That is, a support member may act as a tool to handle or immerse the diffusion packets. Such a tool may in itself be ornamental and function as jewelry, etc.

Designing Drinks

Further, it is possible to offer many individual packets with different, and/or varied, ingredients thus enabling the consumer use more than one, with and/or without a support member to, in effect, create unique drinks by personal design. While there are many ways to do this, one way would resemble an assemblage of grapes, (individual packets) on a singular vine which can be carried out by hooking, threading, and/or the like.

Further, it is conceived that individual packets be shaped like and/or printed on resembling (example) various looking fish and their forms. The container could even resemble a pond, ocean, aquarium and/or the like. Our junior fisherman can select the fish he, and/or she, wish to include in his/her container from the selection. One can offer fishes that bring color; while others bring healthy agents, etc.

Marketing

It is further noted here that consumers may send into the company their unique combinations so as there in lies conceptual, and/or actual, beverage design for ready to drink potential. Just like the chili cook offs, or the contests that Pillsbury® holds it is now possible to hold beverage competitions, and preferably by category.

The just aforesaid offers a marketing advantage not exact, but could closely resemble the marketing concept now set forth. The inventor brings forth the offering of packets with a room temperature and/or cold bottle of water, and/or fiber-water, water containing soluble fiber, (U.S. Pat. No. 6,248,390 to the same inventor, Stillman), in a dining, and/or convenience, venue whereby a consumer is offered for free, or at a nominal charge, an assortment of various packet formulations to select from; (Very common as in the case of a hot water delivery, whereby an aforementioned venue may present a tea box, usually herbal, for the consumer). By the nature of which are the most often selected formulations, a potential ready to drink (RTD) product can be test marketed, while promoting the sale of bottled safe water/Fiber-Water™ etc. for hydration purposes and nutritive advantages. The "in venue" container may contain all or any of the pre-described support member components. This is covered more completely and detailed under Business Models and Methods.

Healthier Drinking Healthier Children

In the beverage market today there exist products which have recognizable characters, and/or strong brand recognizable icons; on an aseptic box, packages, the bottle, or a can, but nothing more. It has already been set forth in this invention the goal of designing beverages with a beverage delivery infusion system(s), which can include any number of components, designed for enhanced hydration and nutritional delivery, all in an effort to encourage "healthy drinking", especially in children. It is the inventor's intent, with this invention to positively impact the health of, not just children, but everyone, regardless, of the considered competitive elements of the characters, and/or the icons, by all that is inclusive in this invention.

There are many multiple vitamins in the market today especially designed for children, with consideration of contents, and/or consumer appeal. More often than not, they are chewable, and some even come in assorted flavors. Further, they are attached; usually to a well-known character. (Flintstones by the Bayer Corporation and Sesame Street by J & J) as mentioned earlier.

As with the above, and/or the nutrient supplemented confectioneries, the inventor is concerned, and notices, that if the child likes the taste (can resemble candy) and/or the character then the child is likely to want more, ergo overdose, because the product is not taken as seriously.

Further, chewables do not require water for administration, which can mean that many of the ingredients do not go directly into the stomach and many linger in the mouth, and, over time, possibly have a negative effect in general, and also on the teeth, and/or mouth tissue.

Additionally, taking these chewables does not afford any opportunity for hydration. Further, the child gets a bolus dosing, which may, or may not, be "the best way to administer".

Nutrient enhanced "Gummies": In the market place today there also exists for children gummy delivery of vitamins, minerals, phyto-nutrients and the like. The shape that the inventor has noticed most often is that of a gummy bear. The suggested dose is two (2), or three (3) daily. It is very difficult to have the child stop at just this amount. They, more often than not, perceive these as candy. The inventor has experienced this also as she has tried them.

The inventor also knows a mother whose child cries when he can only have his allotted two (2). That mother buys regular gummies, with no active ingredients, and mixes, about ten (10) regular, with the two (2) Yummi Bears™ containing active ingredients. The child is now content, but nothing has promoted the so needed hydration, and the child has gotten a significant amount of candy/sugar as well.

This sugar also promotes carries in the mouth as it sticks to, and in between, the teeth. (Yummi Bears, by Hero Nutrition {San Juan Capistrano}, has become the number one children's supplement brand in the health store channels. In July/August 1998, this company grew 214%. Now the product line is expanding rapidly to drug stores and mainstream supermarkets.

While the inventor has addressed fortified confectioneries in packets that would release beneficial agents into a liquid, it is further conceived, that then an entire RDA for individuals, most likely children, can exist in one or more packets.

It is therefore conceived, that a daily supply be packaged together, with or without a support member. Using this inventive method, the beneficial ingredients may be divided in like, and/or correlating the time of day to specific nutrients. As an example, the B vitamins may afford energy, and they might be best taken in the morning. Vitamin C, which is not retained, may be divided throughout the dosage (to be taken daily) packets regardless of the number of packets. Further, by this invention, and according to the best of knowledge of packaging together, children as an whereby a daily dose may be divided into 3 packets-and-therefore packaged accordingly.

It is also known that when one is sick, especially a child, hydration and nutritional supplementation is very important, especially hydration in case of a fever and/or the flu. Further, it is most difficult to get them to drink at all, yet alone a healthy beverage(s).

To that end, not just a single packet but that there be fashioned an entire day supply of infusion packets, especially designed to address the common ailments of school age children (colds, sore throats, colds etc.). Best method would be to make the presentation part of a toy, game, etc. whereby the child would be encouraged to drink one packet after another. Secret doors in a box may be opened one by one-revealing clues as to solving a mystery. The object would be to make a beverage, while at the same time reveal a clue. As an additional possibility, the infusion packet could have a secret message on it that doesn't become apparent until wetted/submerged in liquid/water whereby the writing only then becomes visible.

Tags/Fobs

Tea bags and other infusion bags are often provided with a tag 16, attached to the bag itself through a thread 13, to make it more convenient for the user to handle the bag. Just as there is a tag, so therein lies an art in attaching the string to the tag U.S. Pat. No. 5,580,408 to. Vernon, Goodwin, Cleall, (Thomas J. Lipton Co. NJ) titled Method for the production of tagged articles. However, the inventor has taken note that while many tags have printed material on them, none have reflected a new additional use and/or function.

As just one example it is therefore conceived by the inventor that the tea tag, regardless of construction material(s), may be of a special shape such as a puzzle piece. Thus in this instance, collecting all the tea tags from the infusion packets in one container whereby they would fit into a form for a puzzle. That form would be included in the box. These objectives are most appealing to children who enjoy the entertainment/edutainment/fun/challenge, and to their parents/care givers for the same reasons, but additionally, who also are trying to guide, and/or alter, their children's drinking choices towards a healthier and hydrating direction.

Additionally, puzzle components etc., and/or the like, may be attached to the packets, and/or included with the packet, and/or enclosed within the outer wrapper. These could be given out by a major restaurant chain such as Mac Donald's®.

Therefore, every time a liquid, mainly water, is purchased the consumer would select a packet of choice. This is much as if one were selecting a beverage. When one completes the puzzle, game, or has the lucky number, and/or piece, one would be entitled to a reward/prize. This can serve as a contest, a cross promotion, a discount towards a future purchase, etc.

This is a best effort to encourage, not just the fast food chains to endorse and supply healthy beverages without having to stock a large ready to drink inventory, but to encourage consumers, mainly children, to "drink healthy".

Figure 6:
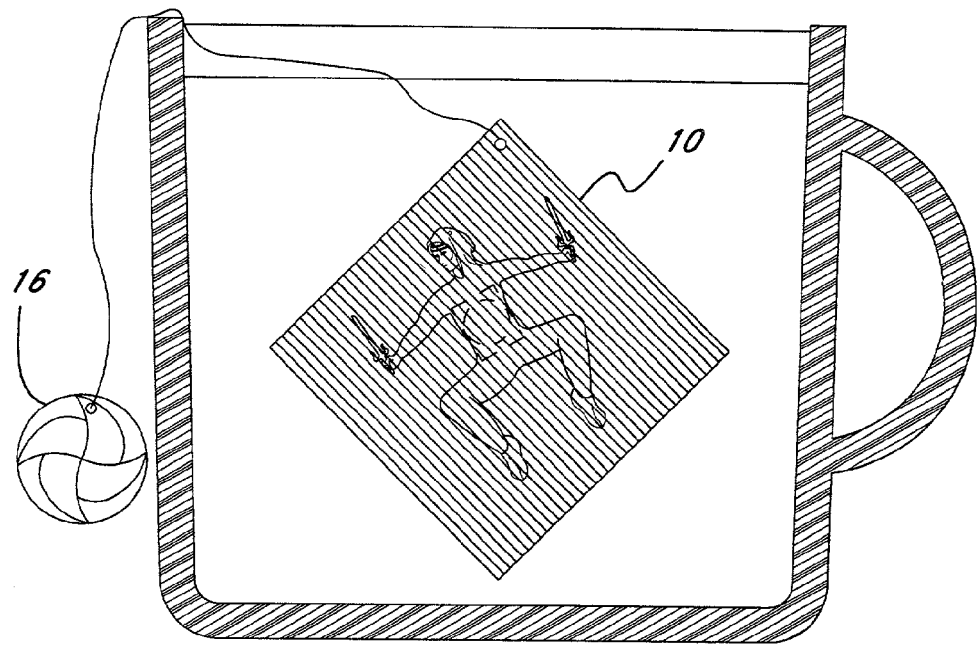
FIG. 6 shows an infusion packet with a hidden design printed on the packet.
Figure 7:
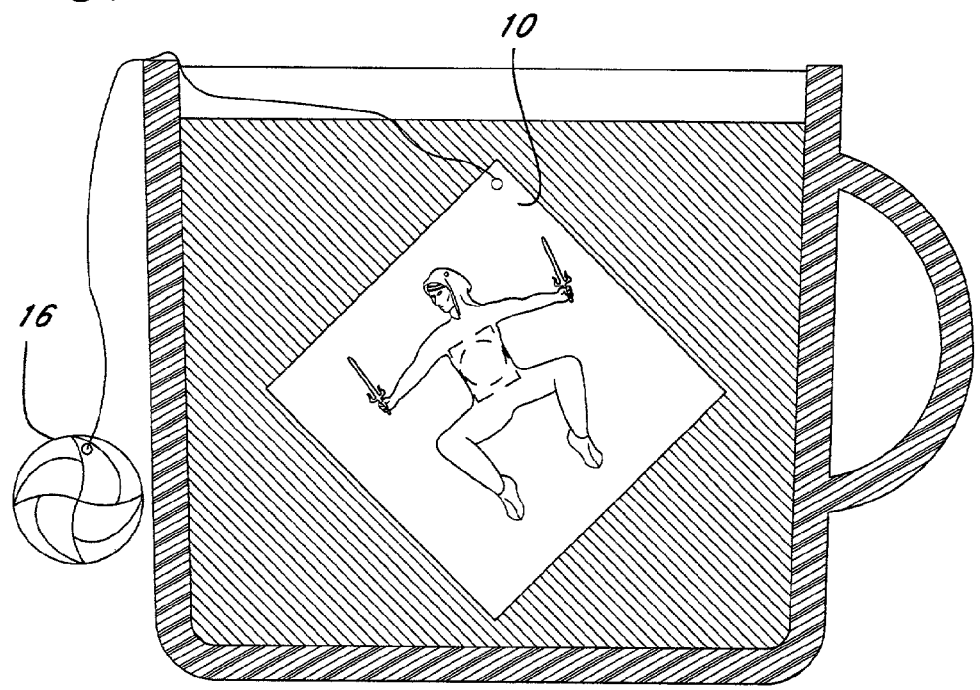
FIG. 7 shows the packet of FIG. 6 after immersion in liquid whereby the hidden design is now visible.

As shown in FIGS. 6-7 the tag 16 can forms a recognizable part of the regalia of a character (here the ninja pictured on the packet 10). As shown in FIG. 8 the tag 16a can be a charm, or the tag 16b can be a clip to fix the tether to the edge of a vessel. Of course, such a clip can also act as a piece of jewelry, hair ornament and/or the like.

Figure 14:
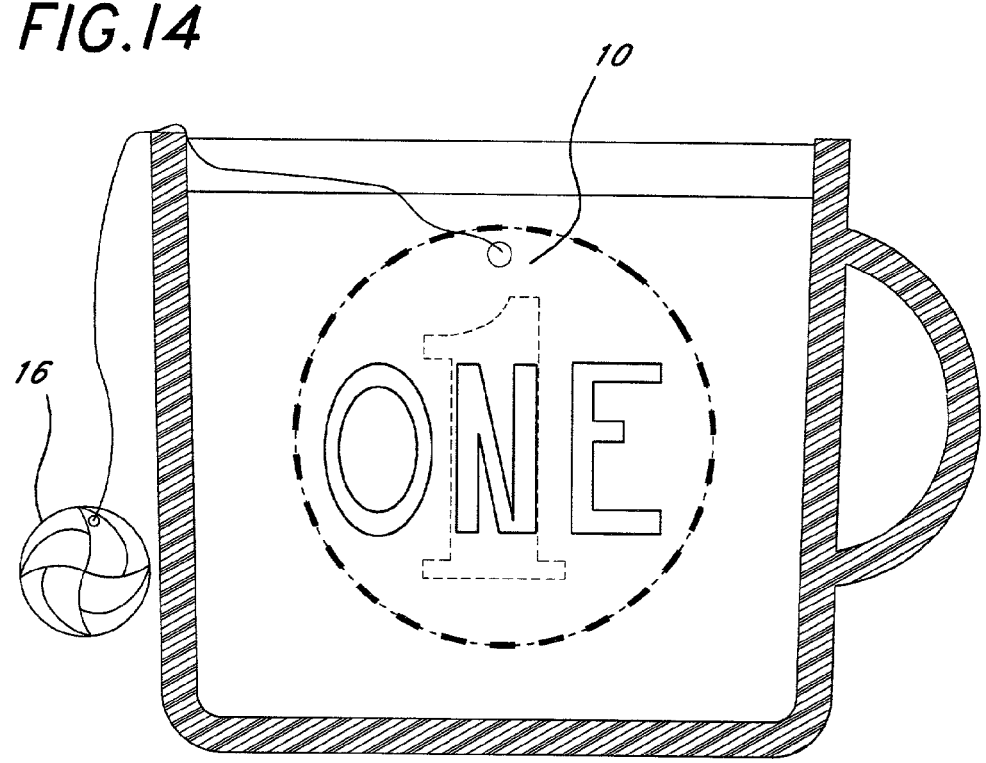
FIG. 14 illustrates another game wherein tags serve as cards with the winner finding a "preferential card".
Figure 15:
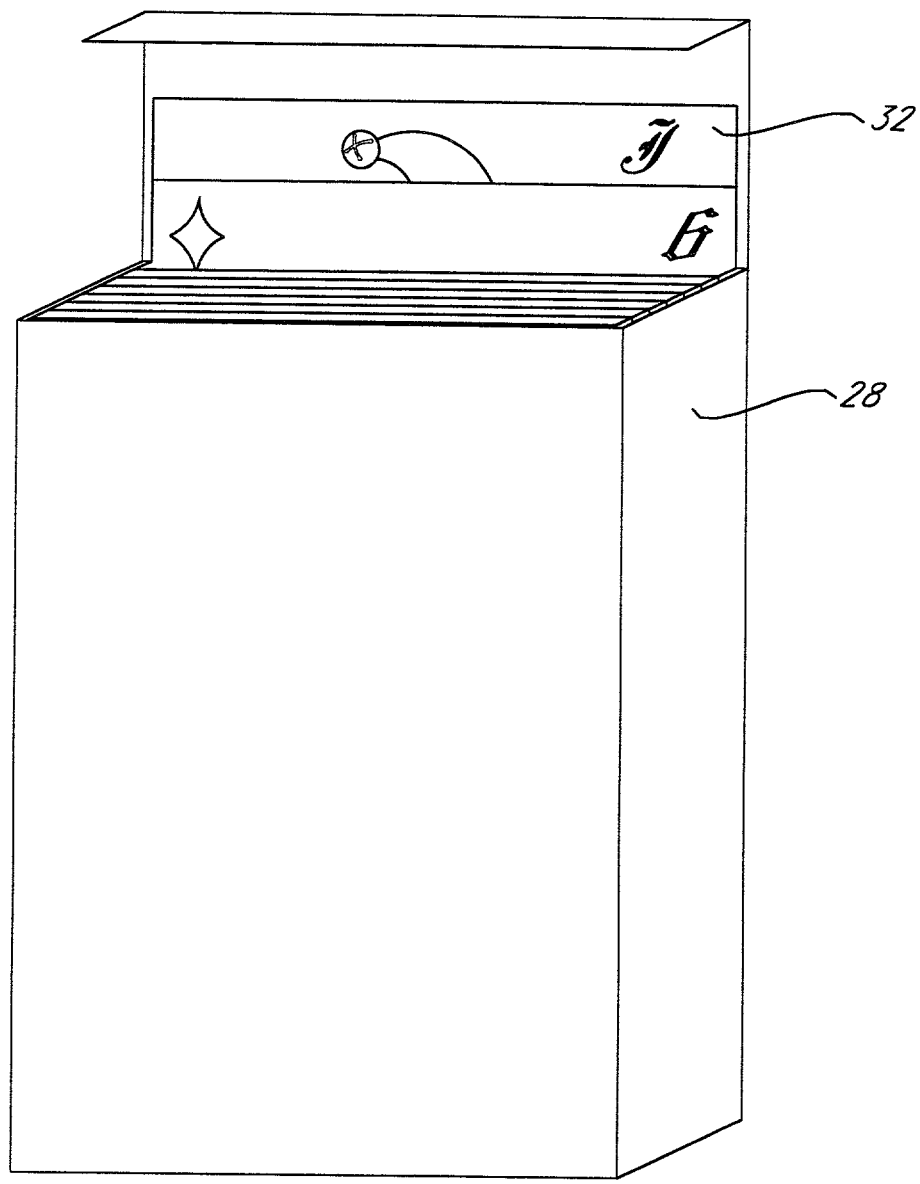

Another example of a novel use for tags would be a game such as a card game. The game would consist of a deck of cards usually 52; however, a reduced number could be used—seven of them (as example one for each day of the week). From the "cards" would be tethered an infusion packet suspended from say each. The aforesaid cards (see FIG. 14) are special to the deck as they represent a wild card, an action card, an instruction card, and/or the like. The object, and here mostly related to a child, is to collect all seven special cards by first using the infusion packet to prepare a beverage, next drink the beverage, dispose of the packet, and add the card to the deck. As more cards are added to the deck, the game becomes more interesting and challenging. These cards can, serve as trading cards too, and one child may now be able to get other children to "drink healthy" too . . . for cards sake!

Further use of space on a tag may include other elements of noteworthiness such as printed on lottery numbers, fortunes, quotations, characters, horoscopes, and/or the like. These tags may offer a clue, and when the packet is submerged, the answer will appear when the "wetting" occurs.

As a unit both the packet and/or the tag can be printed on in consort. As an example from the child's story Snow White, Snow White can be on the infusion packet and each of the other infusion packets be tagged with a dwarf, or the like. Thus, it is a central part of this invention that the tag serves a special function beyond merely indicating the contents of the attached infusion packet.

Further, the tea tag may be made from any material appropriate to serving its function, synthetic or non-synthetic. Beyond functionality would be a dual use, whereby the tag may be made of a permanent material such as plastic, and/or metal and/or metallic foil, so it can be removed from the string and kept.

Figure 13:
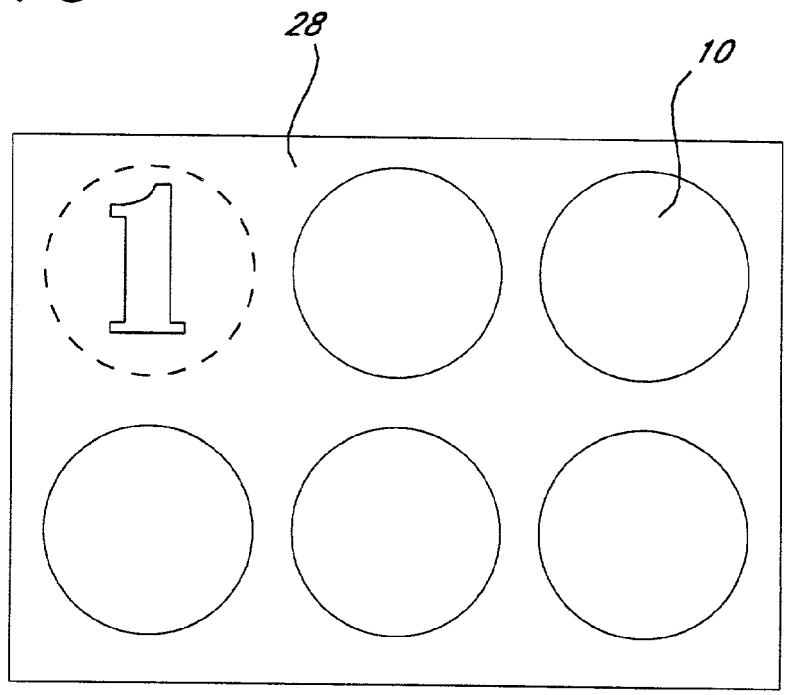
FIG. 13 illustrates a multiple package of infusion packets that form a number game wherein individual packets reveal numbers related to their tags upon immersion.

Children love collecting and trading. If well-known characters were used to embellish the tags, a "tea tag" fad could be started, whereby they would become collectable, tradable, redeemable, or serve as a game, and/or a toy piece, etc. FIG. 13 shows a number game wherein the tags 16 show numbers that correspond to numbers revealed in the package 28 when each tag 16 is removed. As an additional "fun" aspect, the packet 10 has a hidden version of the same number that is revealed upon immersion. Another game is pictured in FIG. 14. Here a card game is formed from the tags 16, each of which acts as cards. The object is to collect a particular "preferential card" 32.

Within the packet, itself there can be an assortment of ingredients. In addition, within a given container of, packets, there can be an assortment of packets, which may have not only mixed formulations, but also mixed designs of the same theme, and/or mixed themes, as reflected on either the packet, tag, and/or both. As an example, a container could be very devoted to one Disney® theme with all the characters, or a mixed assortment of Disney intellectual properties.

Figure 10:
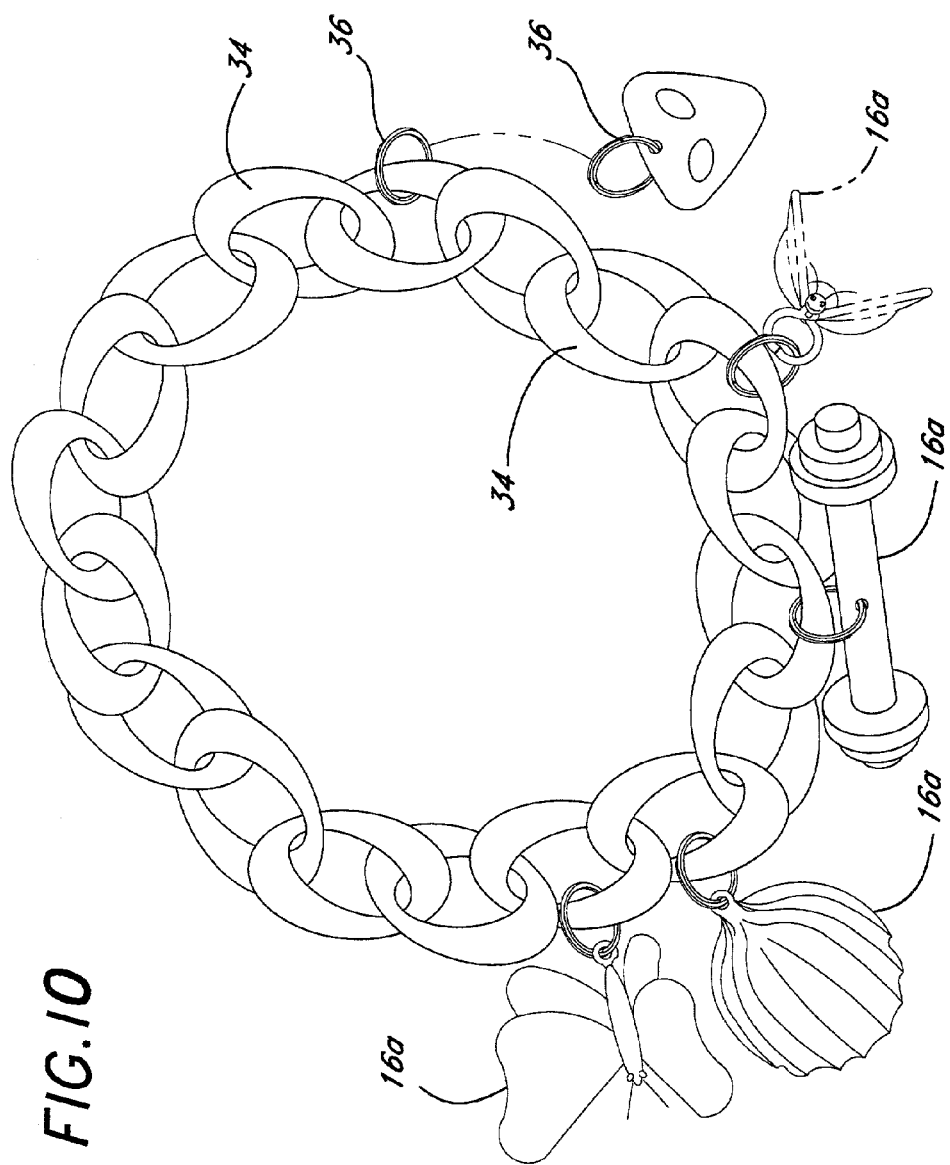
FIG. 10 illustrates a charm bracelet composed of charms that serve as infusion packet tags (as in FIG. 8).

An example of this concept would be to include, within the packaging and/or container, a plain chain link bracelet, and each tea tag function as a charm, flat or dimensional, so when the thread to the packet is removed the charm/tag maybe attached to the bracelet to make a charm bracelet. For this to happen it would necessitate an attachment device. To that end, a "jump ring" would be provided either on the bracelet, or on the tag/charm itself. FIG. 10 shows such a charm bracelet where each tag 16a acts as a charm. The charms can be readily added to a chain loop 34 by means of "jump rings" 36.

These types of situations are most useful in the encouragement of getting children especially, to drink the liquid to collect the charm. This would present as an appropriate reward to acknowledge and reinforce good drinking, as opposed to receiving a sugar-laden reward. It is also conceived that the tag may have a decorative clip on the end instead of a charm. When removed this clip, as illustrated as a butterfly here, could, when removed, be clipped to clothing and/or hair. It is further conceivable that any charm may be fashioned to operate, interchangeably, as a clip or a charm providing the necessary activating parts are present. See FIGS. 8 and 10.

Envelope

While enveloping material and design concepts with multiple design elements along with impregnating technologies, rolling and/or folding techniques, and the like, have been previously discussed the inventor here makes another important inclusion.

1. In one instance, the contents of the packet are enclosed within the folds of a porous paper, or non-woven fabric (although woven fabrics are also used), and/or additionally having a synthetic component having a plurality of openings between the constituent fibers, and/or beneficial ingredients, and/or elements.
2. In a second instance, the contents of the packet are enclosed within a structure such as paper, foil, plastic etc., opaque, or transparent (see through), totally or partially, having a plurality of openings most commonly known as holes pores, and/or perforations.
    a. The openings are proportioned so that the contents are held securely inside until submersion and/or wetted.
    b. Another option; is where the pores are covered by a covering that is tightly affixed to prevent the contained ingredients from escaping, before demand, and is sanitarily protected according to FDA regulations.
3. The third instance would be a combination of both, designed with specific intent.

It is also conceived as a part of this invention, that any or all of the just aforementioned maybe combined inside of each other. An example would be like double bagging, with room between the outer and inner bag for any and/or all of the inventiveness aforesaid, and described, in this embodiment, and/or obvious to those skilled in the art, with complete knowledge and understanding of the contents herein. Just in all the aforementioned, the sheet goods used to fabricate the bag may be colored, printed on, etc. If the specifications call forth for a material that is not porous, and thereby holes/perforations are warranted for the transfer and mixing of ingredients, then it is conceivable that these openings are made on the sheet goods first, most probably with a die cutting machine.

The material may be printed on as well as having the holes made. The holes my be made in any shape, and/or collection of shape's, planned, or randomly done, so long as they support the best use of the invention. It is also possible to have a pattern, or design, be compatible with the perforations made. An example of this would be to have an alien character that can be submerged, where by the liquid is attracted into the bag. Therefore, when one lifts the bag the liquid can pour out from the alien's features, most probably the eyes and/or nose and mouth.

Concepts like this, and others in the same category, maybe most appealing, incredibly delightful, and most welcomed by the younger population especially.

Again, there has been insufficient attention to use of the infusion packet envelope to enhance and/or be interactive with the overall product.

No one has produced a fabrication whereby the surface material is used to display graphics, including but not be limited to recognizable symbols, and other indicia, cartoon characters, text, advertising materials, representative objects, pictures, jokes, riddles, fortunes, lottery numbers, horoscopes, etc., or the like. The latter is especially of note in regard to children, and to those children who are loyal fans of popular characters such as; Mickey Mouse® (Disney), Pokemon®, and super-heroes such as Superman®.

Further, other than emptying a packet into a liquid, or dunking a tea bag there has been no new and novel interactive, especially educational, and/or informative, components attached to the just aforementioned.

Figure 12:
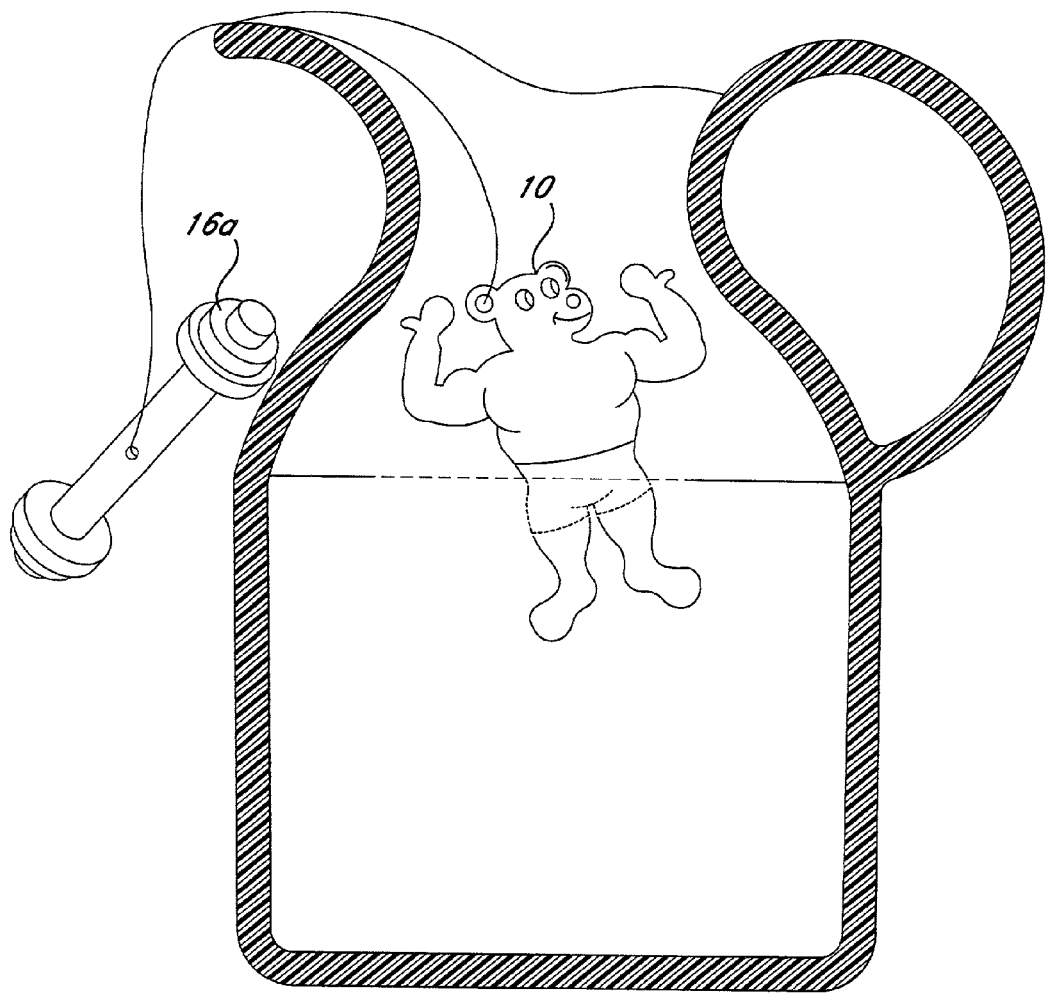
FIG. 12 illustrates an infusion packet wherein the packet is formed as a figure and the tag is a counterweight.

Examples of "figure-shaped" packets can be found in FIG. 2B showing the alien figure and matching tag and FIG. 12 showing a packet shaped as a character (bear) 38 with a matching weighted tag 42 to keep the large bear from "flopping" over in the liquid.

Effervescence

In many instances, effervescence is desirous or deemed of value. First is may mask the taste of some ingredients. Additionally, it may add a quality to the liquid that may closely resemble a soft drink for which the market is huge.

However, working with effervescence is not easy. The inventor is fully aware of the hygroscopic nature of effervescent ingredients, and therefore knows that an outer wrapper must protect it.

Upon experimentation, the inventor discovered that by having an effervescent tablet inside of a porous bag it floated to the top of the glass, regardless of the temperature of the water. While it did effervesce, it did so at a very slow rate.

Further, due to the innate properties of effervescence the porous bag would need to be contained in a moisture proof, air tight, outer package until ready to use.

However, when the tablet was put into a packet with very definite holes, larger pores, not only did it activate faster but it created, what might be called a "storm in the teacup". The release of the effervescence, and the accompanying bubbles, occurred simultaneously inside the packet as well as outside the packet into the liquid. In some experiments, it also moved around quite a bit due to the propulsion/motion of the bubbles. Again, a reminder that if the packet is presented with existing holes, then the aforesaid problem may occur. If it is desirous that the perforations made in advance, then there must be a second moisture proof, air-tight, outer wrapper that is not opened until time of use.

With the thought of protecting the effervescence, and/or any other ingredients, which are moisture and/or oxygen sensitive, a packet can be made without any openings.

It would be wise, but not necessary, to provide this kind of a packet with an instrument designed specifically for allowing one to make his own holes. This instrument may be provided attached to each individual packet, and/or be part of the tag, and/or be the tag. Another option; is to have the instrument accompany each individual packet in the same outer wrapper, or be affixed to the outer wrapper, much like the little straw goes with the aseptic juice boxes.

Further, one or more instruments may be provided in a larger container, such as a box or a tin that contains many packets. It is also possible to have a design, whereby the user would automatically be guided as to where to make the holes, like in facial features such as the eyes. At the consumer's discretion, the user may decide to make the random holes necessary for activation. With this part of the invention, the consumer, in most part, would also control the quantity of material released, and the time involved for releasing would be proportionate.

If there were a tablet inside the packet, it would not be problematic if the tablet broke upon puncturing the packet.

In all the above circumstances, the active and/or non-active ingredients may be delivered in any form, including the use of encapsulations.

Clear Films

An additional part of the invention presents the use of clear and/or opaque films, either water insoluble or water-soluble. They each have a purpose in the invention. Further, they can be used independently and/or in combination with each other.

Many infusion products are packaged in a clear outer wrapper, but the infusion packet itself, contained within, is not transparent. With this invention it is possible to have a clear outer wrapper, and a clear encompassing material for the ingredients. The packet material may be water insoluble following all the art described above as related to design, holes/perforations and/or the like.

Or the inventor presents the possibility that it may be water-soluble meaning, that it totally, or almost totally, dissolves when introduced into liquid. It is possible that it will change form and become somewhat gummy, whereby it can be chewed if so desired.

Either the water-insoluble film, or the water-soluble film may include encapsulation technologies, and/or be coated with, and/or impregnated with, encapsulated ingredients, whereby the material may remain clear, or become opaque.

University of California researchers have succeeded in developing water insoluble films by developing a novel procedure using a variety of protein sources to produce water insoluble films. U.S. Pat. No. 5,543,164 to Krochta, McHugh, (Univ. of Calif.), titled Water Insoluble Protein Based Edible Barrier Coatings and Films.

These films can be useful in protecting food products from oxidative degradation and moisture migration. Tests have shown that these protein based films are excellent oxygen barriers, having oxygen permeability very close to plasticized poly(vinylidene chloride) (PVCD) and less than polyvinyl chloride (PVC). The water vapor permeability of the protein barriers is comparable to other based edible films, as they prove to be completely insoluble in water.

It is conceivable that an infusion packet could be made of this film with the necessary holes made for the transfer of; and/or in liquid. These films are clear and would readily display, not just the ingredients, but make the activation process viewable.

It is conceived that this film be used alone and/or in combination with the same water insoluble film as the wrapper. As an example, the water insoluble film may be the clear outside covering for a soluble film product, and serve as the outside wrapper. The formation of the film is highly flexible, and when in use can protect thus improve flavor, aroma, etc. The same materials used together, would have the resemblance of being totally, and/or all most totally clear, and thus would allow for complete viewing. Further, either the wrapper and/or the packet itself maybe printed on.

Using a water-soluble film, it is further conceived whereby the entire infusion packet used to enclose the ingredients may be subject to the liquid. With this application, there is no need to consider trans-delivery through and/or across a membrane.

1. First of all, such delivery dispenses with the mess of the removal of the infusion packet from the liquid.

2. Second, the material of the edible film may add active ingredients to the liquid to enhance, sweeten, color, etc. the beverage.
3. Further, it ensures that all the contents will be used.
4. Further, it can be a source of entertainment, especially for children, along with those who like excitement and magic.

If so designed that the soluble film will dissolve in room temperature water then this would be most desirable to add to the water bottle infusion packet portion of the invention. It is also possible, but the reaction would be much slower, for the film to dissolve in colder water Compartments By providing packets of this nature—infusion packets having ingredients in separate compartments, but within the same packet, allows for incompatible ingredients when stored, but compatible and synergistic when mixed, to realize their full potential.

Ingredients, such as pro-biotics and pre-biotics, enzymes, etc., cannot be presented in a ready mixed solution without protection and be sure that the activity is stable. Presently they are very sensitive and as an example, to maintain stability, they have to be handled very carefully.

Additionally, this would apply to including encapsulations of ingredients, which do not taste good so to have a greater chance of assuring consumer compliance and appeal.

Further, less sweeteners will be necessary to mask the off taste, and/or to better address unacceptable flavor(s) that are used.

Additionally; even if previously mentioned, this potentates the probability that less chemicals will be needed also.

The inventor hopes that this will address the ability of providing a more healthy product, especially reducing the over abundance of sugar used today which is leading to obesity, and possibly diabetes, mood swings, hyperactivity, etc.

Acids

Further, this will reduce and/or eliminate the need for food acids present in all ready mixed beverages. It might additionally permit the use of different acids, which might be easier on the system and/or more acceptable in general. While small amounts of these acids may be used for flavoring their main purpose has been to create an acid medium so as to reduce the microbial growth of organisms within the product. The inventor is most concerned with microbial growths having dealt with the same issues many times.

Compartments

Further, it is important to note that extreme attention is given to the active ingredients that are contained within the infusion packet, and/or impregnated into the infusion packet.

Every effort is made to use existing and new technology to best serve the parameters of each ingredient. To best do so it may warrant the necessity of having more than one compartment. U.S. Pat. No. 5,728,681 to Kido, Kodaira, Munechika, Li, Abe, Yokoyama (The Green Cross Corp. Osaka, JP), titled Infusion preparation and two compartment container containing the preparation. Here is taught the separation of liquids whereby a separator divides the compartments. When removed the liquids in both compartments mix.

While the final result may present a packet with multiple compartments, like a quilt, it is also conceivable that single units be grouped and connected with a support member, as previously described using the grapes/cherries as the model(s).

This may be accomplished in the following ways:
1. One way is to have multiple packets suspended from one central unit, whether it be it a string, a straw, a rigid form, or a coil resembling a spring (Slinky), and/or the like.

These multiple compartments may be grouped all in one area, possibly the end, thus resembling a bunch of cherries.
2. Alternately, they may be staggered along what would resemble a vine, and look like flowers on a vine. To this end each packet could be the shape of a flower, and/or bare with it a flower print design on the packet.

While in the former, cherry-like formation, the individual bags could have thread loops on the end whereby they would slip onto the stalk portion. It is also conceivable that the support member have a clip(s) on the end by which to attach these packets. In the case of a flower model, stalk/vine, little hooks, and/or clips, would be provided going up the vertical.

Of special note is that if one chooses to use the latter, the stalk/vine, it would be recommended for a larger vessel like a pitcher for function and beauty. FIG. 11 illustrates a special support member 44 used to combine a number of disparate infusion packets. This allows a mix and match approach to beverages as well as serving as a means of keeping incompatible ingredients separate. FIG. 11A shows a "quilt" wherein the support member 44 is used to join individual packets 10. FIG. 11B shows a section through the packets 10 to emphasize the variation in internal contents.

It is also conceived that an alternative to a quilt would be a layering formation whereby it would resemble a sandwich, and/or the likes of a multi layered cake.

It is conceivable that a boxed unit of infusion packets may contain one or more central units, and then an entire selection of infusion packets labeled as: to the color (if not visible), aroma, active ingredients, etc. so that the consumer, by choice, may make individual and personal unique combinations.

Once again, the inventor reflects on all the variations and differences available in say chocolate chip cookies, donuts, and/or the like. In fact entire business have been built around the aforementioned; Mrs. Fields®, Dunkin Donuts®, etc. but none in beverages for the general population.

However, the inventor is aware of all the juice/smoothie venues that have recently opened up, like Jamba Juice®, Robecks® etc. Additionally, all the coffee houses like Starbucks® and The Coffee Bean® chains which offer numerous variations and choices of coffees, and now teas.

While the just mentioned do offer variety, and the former nutrition, and nutritional additives, these establishments have to be patronized, and additionally, come with a hefty price, more often than not affordable by only the wealthy. To enrich a fruit smoothie, which basically costs $2.00, one can purchase, for an additional fifty cents, each one, or more, of the following, fiber, protein, vitamins, minerals, and antioxidants, etc. This then becomes a very expensive proposition, and certainly does not address a more healthy population in general. The goal of the inventor is for mass marketing and distribution.

Animals

Animals, especially personal pets and additionally all the "aid dogs" (for the blind, police K9 dogs,) etc. are a major part of our society bringing help, joy, pleasure, companionship, etc., to the lives of young and old alike.

Some pets have become so much a part of the family that they even sleep in the same bed, travel with, and/or the like, with their owners. Further, now pets are even being brought into hospitals and other institutions to visit patients.

Pet health is important, and further, it is big business. As a business, and to bring to the marketplace well-studied ethical nutritional products, one is faced with many of the same problems that face the people population. Sometimes even more, because there are many categories, which compose the animal kingdom, and this invention is not limited to what is normally considered to be, just the "ordinary household pet".

While it is true that pets might have some fickle tastes, along with individual preferences when it comes to their food, they still need nutrition and care in relation to specific conditions.

To get medication, including but not limited to even some vitamin preparations, one only has to look at what it takes to get this into a pet. Pills have been buried in bits of food, more often than not. Besides, it is very difficult to offer a trip to Disneyland® to your dog.

The inventor has noticed a great sensitivity to pet nutrition by many companies especially the Iams Company® (Dayton Ohio), with reference to the following U.S. Pat. Nos. 6,039,952 to Sunvold, et al. titled Composition and method for improving clinical signs in animals with renal disease; 6,204,291 to Sunvold, et al. titled Process for promoting weight loss in overweight dogs; 6,180,131 to Sunvold titled Process for improving glucose metabolism, satiety, and nutrient absorption in companion animals; 5,776,524 to Reinhart titled Process for treating small intestine bacterial overgrowth in animals; 6,133,323 to Hayek titled Process for enhancing immune response in animals using .beta.-carotene as a dietary supplement. Additionally, U.S. Pat. No. 5,968,569 to Cavadidi (Nestec S. A., (Vevey C H), titled Pet food product containing pro-biotics; U.S. Pat. No. 5,294,458 to Fujimori (Maruha Corp. Tokyo JP), titled Pet food—where this invention contains lactosucrose to keep the intestines of the pet in order, provide a good taste and a great effect on deodorizing feces and urine discharged by the pet.

This invention for animals is to provide a liquid animal food composition, which provides, along with hydration, other active and/or non-active, ingredients.

This invention for animals relates to the ability to directly give, and/or give directly as a water enhanced product, and/or a beverage, and/or through another food product, (mixed in) species related, and/or need related, a beneficial liquid for increasing hydration, with the added feature of one or more beneficial agents to treat a specific condition, performance desire; promote general health, and/or the like.

Animals have many of the same problems as humans as far as the following: viral and/or bacterial infections, and/or inflammatory conditions, and the like. Certain animals, such as dogs, as well as humans, sometimes suffer from diabetes, or have an impaired ability to regulate blood, sugar levels. Once diagnosed, they have to be closely controlled by diet, medication and/or both.

Certain animals also have a tendency towards excess caloric intake, which increases, as in humans, the risk of the animal developing not just diabetes but other chronic diseases. It would be more than just desirable to manage caloric intake through dietary means so that the animal would become sated after meals, but without excessive caloric intake.

Animals, by and large do not eat for social purposes nor do they follow the psychological, often pathological, patterns so associated with humans and their food behaviors. Therefore, by this invention much can be offered to the animal kingdom.

The inventor is most interested that animals receive more fiber for many reasons, and ergo the reader may refer to her U.S. Pat. No. 6,248,390 Fiber-Water: Water containing soluble fiber; for an extended appreciation.

Additionally, there are numerous, and far too many well-designed examples of all sorts of additives being used for animals which are, and/or do, produce food, for humans and other animals. (e.g. chickens, cows, pigs etc.) Careful consideration must be given to those animals, which are eaten and/or produce food for eating (eggs), and/or both.

Further, there exists a special group of nutritionally engineered products for, what the inventor calls, competitive animals such as; race horses, polo ponies; greyhounds, etc. An extension would be show animals of all types, and working animals on ranges and farms. Further, would be animals specifically for breeding.

In our zoos and circuses we have in captivity many wild animals, birds, etc. for which we are responsible for their nutrition.

With a consciousness towards the best way to deliver, in all the categories of supplementation, as described for humans (people), one is reminded that animals do drink everyday. It is also noted that many times liquid is needed to wet animal food, and/or by necessity, and/or design, choose to imbibe the food with additional liquid.

More specifically, pet foods for dogs and cats, as an example, is usually classified into a dry type, a semi-moist and often called a soft dry type, and a wet type. In all these instants, liquid can be added.

1. The dry type pet foods include as an example a moisture content of below 10%-12% in forms such as kibble, biscuits; flakes, crumbles (granules).
2. Semi-moist usually have a moisture content ranging from 25%-35% and are in the form of hamburger, ground meats, fowl, and/or the like.
3. The wet type food includes food having high moisture content of 70%-85% whereby many canned foods and, those which have undergone a retort process method fall into this category. There are oatmeal type foods comprising of meat and fish as well as those that have additionally added vegetables and vitamins, and the like added additionally.

If the liquid has a flavor in it, which will mask the unappealing tastes of many of the aforementioned ingredients, and/or elements, as described for humans with and/or without encapsulation technologies, then there is a greater chance of compliance.

Further, even animals have fragrance preferences by nature and/or learned. For a cat, one could envision a fish smelling water, the inventor just doesn't know what kind of fish as of yet. Conceptually this can extend throughout the animal, bird, and even reptile communities.

It was a real learning experience for the inventor to study animal habits, preferences and pet food products for the specific goal of inventing/designing for this enormous category, good tasting nutritious healthy products/additives.

Business Opportunities, Models and Methods in Relation to Animals

The inventor feels that much of what is covered above can now, with modifications, also provide for some opportunities in the in the animal market place.

Animals, mainly pets, that may accompany their owner on a regular basis are usually on a leash and are afforded the opportunity of being present at various venues especially, vending machines.

Therefore, following all the vending machine illustrations, models and methods detailed earlier, a packet, with or without a support member, may be dispensed for an animal. This would, as an example, allow a product for a dog, cat, etc., to be dispensed even from the same machine(s) as those for humans, so long as it is labeled properly.

Also to be noted that support members, because they are also considered to be functional, useful, may be nothing more than a mixing, and/or drinking, vessel of normally recognized design and/or special design.

There exist on the market collapsible cups, which may and/or may not be "throw-aways", ergo one time use (hopefully bio-degradable).

Further, more common in other countries pets, are taken into restaurants, and other venues, ergo thus far this inventor has yet to see a pet being given a beverage option.

The inventor also makes note that there exists an opportunity for testing a potential animal product and/or testing certain additives which may, or may not, find a home, and be packaged, with animal/pet food regardless of type of product, amount of servings provided, container size, shape, and/or the like.

In addition to the equivalents of the claimed elements, obvious substitutions known to one with ordinary skill in the art are defined to be within the scope of the defined elements. The claims are thus to be understood to include what is specifically illustrated and described above, what is conceptually equivalent, what can be obviously substituted, and also what essentially incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. An infusion packet delivery system for adding a health enhancing ingredient to a beverage, wherein the beverage comprises water, the delivery system comprising:
    a packet having contents consisting of water soluble ingredients, wherein said ingredients comprise a health enhancing ingredient, and wherein the packet comprises at least one pore configured to allow all of the ingredients to dissolve and to diffuse out of said packet upon immersion of the packet in the beverage to release said water soluble health enhancing ingredient into and throughout said beverage, and wherein said packet is capable of changing upon immersion in the beverage to form a shape that is entertaining to the consumer of the beverage; and
    a detachable entertainment feature attached to said packet to encourage consumption of said beverage, wherein said feature is a toy, a charm, a game piece, a key ring, jewelry, a sticker, a clip, an ornament, or combinations thereof.

2. The system of claim 1, wherein said feature provides an aroma.

3. The system of claim 1, further comprising a connector that connects the packet to the feature.

4. The system of claim 1, wherein the health enhancing ingredient is a water soluble fiber.

5. The system of claim 1, wherein the beverage is water.

6. The system of claim 1, wherein the feature is a toy, jewelry, or a game piece.

7. The system of claim 6, wherein the feature is related to a set so that the feature may be collected to complete the set.

8. The system of claim 1, wherein said entertainment feature is capable of one or more of the following: motion, changing color, glowing in the dark, emitting light, emitting sound and revealing a message.

9. An infusion packet delivery system for adding a health enhancing ingredient to a beverage, wherein the beverage comprises water, the delivery system consisting of:
    a packet having contents consisting of water soluble ingredients, wherein said ingredients comprise a health enhancing ingredient, and wherein the packet comprises at least one pore configured to allow all of the ingredients to dissolve and to diffuse out of said packet upon immersion of the packet in the beverage to release said water soluble health enhancing ingredient into and throughout said beverage, and wherein said packet is capable of changing upon immersion in the beverage to form a shape that is entertaining to the consumer of the beverage; and
    a detachable entertainment feature attached to said packet to encourage consumption of said beverage, wherein said feature is a toy, a charm, a game piece, a key ring, jewelry, a sticker, a clip, an ornament, or combinations thereof.

10. The system of claim 9, wherein the health enhancing ingredient is a water soluble fiber.

11. The system of claim 9, wherein the beverage is water.

12. The system of claim 9, wherein the feature is a toy, jewelry, or a game piece.

13. The system of claim 12, wherein the feature is related to a set so that the feature may be collected to complete the set.

14. The system of claim 9, wherein said entertainment feature is capable of one or more of the following: motion, changing color, glowing in the dark, emitting light, emitting sound and revealing a message.

15. An infusion packet delivery system for adding a health enhancing ingredient to a beverage, wherein the beverage comprises water, the delivery system comprising:
    a packet having contents consisting of water soluble ingredients, wherein said ingredients comprise a health enhancing ingredient, and wherein the packet comprises at least one pore configured to allow at least some of the ingredients to diffuse out of said packet upon immersion of the packet in the beverage, and wherein said packet is capable of changing upon immersion in the beverage to form a shape that is entertaining to the consumer of the beverage; and
    a detachable entertainment feature attached to said packet to encourage consumption of said beverage, wherein said feature is a toy, a charm, a game piece, a key ring, jewelry, a sticker, a clip, an ornament, or combinations thereof.

16. The system of claim 15, wherein said feature provides an aroma.

17. The system of claim 15, further comprising a connector that connects the packet to the feature.

18. The system of claim 15, wherein the health enhancing ingredient is a water soluble fiber.

19. The system of claim 15, wherein the beverage is water.

20. The system of claim 15, wherein the feature is a toy, jewelry, or a game piece.

21. The system of claim 20, wherein the feature is related to a set so that the feature may be collected to complete the set.

22. The system of claim 15, wherein said entertainment feature is capable of one or more of the following: motion, changing color, glowing in the dark, emitting light, emitting sound and revealing a message.

* * * * *